US008765458B2

(12) United States Patent
Clark et al.

(10) Patent No.: US 8,765,458 B2
(45) Date of Patent: Jul. 1, 2014

(54) COATED SENSORS AND METHODS RELATED THERETO

(71) Applicants: The Charles Stark Draper Laboratory, Inc., Cambridge, MA (US); Massachusetts Institute of Technology, Cambridge, MA (US)

(72) Inventors: Heather A. Clark, Lexington, MA (US); Karen K. Gleason, Cambridge, MA (US); Salmaan Baxamusa, Cambridge, MA (US); John M. Dubach, Somerville, MA (US)

(73) Assignees: The Charles Stark Draper Laboratory, Inc., Cambridge, MA (US); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/904,348

(22) Filed: May 29, 2013

(65) Prior Publication Data
US 2013/0260014 A1 Oct. 3, 2013

Related U.S. Application Data

(62) Division of application No. 12/584,528, filed on Sep. 8, 2009, now Pat. No. 8,470,300.

(60) Provisional application No. 61/191,467, filed on Sep. 8, 2008.

(51) Int. Cl.
*C12M 1/34* (2006.01)

(52) U.S. Cl.
USPC .......................... 435/288.7; 435/7.1; 435/29

(58) Field of Classification Search
USPC ................ 424/9.6, 417, 489; 435/7.1, 14, 29, 435/288.7
See application file for complete search history.

(56) References Cited

U.S. PATENT DOCUMENTS

| | | | |
|---|---|---|---|
| 4,272,484 A | 6/1981 | Lubbers | |
| 4,272,485 A | 6/1981 | Lubbers | |
| 4,379,041 A | 4/1983 | Petranek et al. | |
| 4,945,171 A | 7/1990 | Haugland et al. | |
| 5,057,431 A | 10/1991 | Lubbers et al. | |
| 5,128,019 A | 7/1992 | Karpf et al. | |
| 5,132,095 A | 7/1992 | Koshiishi et al. | |
| 5,494,640 A | 2/1996 | Simon et al. | |
| 5,691,205 A | 11/1997 | Kawabata et al. | |
| 5,908,624 A | 6/1999 | Scott et al. | |
| 6,143,558 A | 11/2000 | Kopelman et al. | |
| 6,143,570 A | 11/2000 | Alder et al. | |
| 6,379,955 B1 | 4/2002 | Kopelman et al. | |
| 6,699,465 B2 | 3/2004 | Scott | |
| 7,704,704 B2 | 4/2010 | Ibey et al. | |
| 8,268,567 B2 | 9/2012 | Clark | |
| 2002/0155600 A1 | 10/2002 | Kopelman et al. | |
| 2003/0157535 A1 | 8/2003 | Berkovic | |
| 2003/0213691 A1 | 11/2003 | Peper et al. | |
| 2003/0217920 A1 | 11/2003 | Peper et al. | |
| 2004/0048390 A1 | 3/2004 | Wang et al. | |
| 2004/0058384 A1 | 3/2004 | Bakker et al. | |
| 2004/0058458 A1 | 3/2004 | Anker et al. | |
| 2004/0146944 A1 | 7/2004 | Fang et al. | |
| 2005/0011760 A1 | 1/2005 | Bakker et al. | |
| 2006/0008924 A1 | 1/2006 | Anker et al. | |
| 2006/0083688 A1 | 4/2006 | Singaram et al. | |
| 2006/0148104 A1 | 7/2006 | Marini et al. | |
| 2007/0105176 A1 | 5/2007 | Ibey et al. | |
| 2007/0107625 A1 | 5/2007 | Anderson et al. | |
| 2008/0131909 A1 | 6/2008 | Clark et al. | |
| 2009/0142274 A1 | 6/2009 | Clark et al. | |
| 2009/0155183 A1 | 6/2009 | Clark | |
| 2010/0221188 A1 | 9/2010 | Clark et al. | |
| 2010/0227334 A1 | 9/2010 | Clark | |

FOREIGN PATENT DOCUMENTS

| | | |
|---|---|---|
| WO | WO-99/45357 | 9/1999 |
| WO | WO-01/08660 | 2/2001 |
| WO | WO-2004/083902 | 9/2004 |
| WO | WO-2006/050257 | 5/2006 |
| WO | WO-2007/054689 A1 | 5/2007 |
| WO | WO-2007/057743 | 6/2007 |
| WO | WO-2007/067733 | 6/2007 |

(Continued)

OTHER PUBLICATIONS

Barker et al., "Radiometric and Flourescense-Lifetime-Based Biosensors IncorporatingCytochrome C' and the Detection of Extra- and Intracellular Macrophage Nitric Oxide," AnalChem, vol. 71, No. 9, May 1, 1999, pp. 1767-1772.

(Continued)

*Primary Examiner* — Michael G Hartley
*Assistant Examiner* — Jagadishwar Samala
(74) *Attorney, Agent, or Firm* — Edward A. Gordon; Foley & Lardner LLP

(57) ABSTRACT

The invention provides coated sensors for detecting the presence of analytes. The sensor comprises one or more fluorescent sources, such as one or more quantum dots or one or more fluorescent dyes, a polymeric matrix, a surface coating, and one or more analyte sensing components. The surface coating may be a conformal polymeric film, permeable to the analyte, which may be deposited via a solventless process such as initiated chemical vapor deposition or photoinitiated chemical vapor deposition. The surface coating may increase the biocompatibility of the sensor, reduce nonspecific protein adsorption, and/or sequester functional sensor components within the sensor. The invention also provides methods for detecting the presence of an analyte with coated sensors of the invention.

20 Claims, 15 Drawing Sheets

(56) References Cited

FOREIGN PATENT DOCUMENTS

| WO | WO-2007/067743 A2 | 6/2007 |
| WO | WO-2008/016646 A2 | 2/2008 |
| WO | WO2008016646 * | 2/2008 |
| WO | WO-2008/063151 | 5/2008 |
| WO | WO-2008/153930 | 12/2008 |
| WO | WO-2009/051703 | 4/2009 |

OTHER PUBLICATIONS

Brasuel et al. Fluorescent Nanosensors for Intracellular Chemical Analysis: Decyl Methacrylate Liquid Polymer Matrix and Ion-Exchange-Based Potassium PEBBLE Sensors with Real-Time Application to Viable Rat C6 Glioma Cells, Anal Chem 2001 vol. 73, pp. 2221-2228.
Bruchez, M. et al. "Semiconductor Nanocrystals as Fluorescent Biological Labels", Science, Sep. 25, 1998, vol. 281, pp. 2013-2015.
Buck et al., "Nanoscale Probes Encapsulated by Biologically Localized Embedding (PEBBLEs) for Ion Sensina and Imaaina in Live Cells," Talanta, vol. 63, No. 1, May 10, 2004, pp. 41-59.
Buehlmann et al., "Carrier-Based Ion-Selective Electrodes and Bulk Optodes. 2. Ionophores for Potentiometric and Optical Sensors," Chem Rev, vol. 98, Jan. 1, 1998, pp. 1593-1687.
Clapp, A. et al. "Quantum Dot-Based Multiplexed Fluorescence Reasonance Energy Transfer", J. Am. Chem. Soc., 2005, vol. 127, pp. 18212-18221.
Clark, H. A., et al. "Optochemical Nanosensors and Subcellar Applications in Living Cells" Mikrochimica Acta, 131(1/02) 121-128 (1999).
Dubach, J. M. et al., "Fluorescent Ion-Selective Nanosensors for Intracellular Analvsis with Improved Lifetime and Size" Nano Letters, 7(6):1827-1831 (2007).
European Search Report for EP Appln No. 06851882.8, mailed Mar. 31, 2009.
Examination Report mailed Mar. 11, 2010 in EP Appln No. 06851882.8.
Final Office Action in U.S. Appl. No. 12/156,959 dated Oct. 1, 2013.
Garg, G. et al. "Micropigmentation: Tattooing for Medical Purposes", Dermatol Surgery, 2005, vol. 31, pp. 928-931.
Goldman, E. et al. "Multiplexed Toxin Analysis Using Four Colors of Quantum Dot Fluororeagents", Anal. Chem., 2004, vol. 76, pp. 684-688.
International Search Report for PCT Application No. PCT/US2006/036040, mailed Aug. 29, 2008, 4 paqes.
International Search Report in PCT/US2008/007108 dated Sep. 25, 2008.
Kohls et al., "Setup of a Fiber Optical Oxygen Multisensor-System and its Applications in Biotechnology," Sensors Actuators B, vol. 70, No. 1-3, Nov. 1, 2000.
Kulcu, E. et al. "Physiological Differences Between Interstitial Glucose and Blood Glucose Measured in Human Subjects", Diabetes Care, Aug. 2003, vol. 26, No. 8, pp. 2405-2409.
McGraw-Hili Dictionarv of Scientific and Technical Terms, Sixth Edition, p. 1633, (2002).
Nagai, T. et al. "Circularly permuted green fluorescent proteins engineered to sense Ca2", PNAS, Mar. 13, 2001, vol. 98, No. 6, pp. 3197-3202.
Notice of Allowance in U.S. Appl. No. 11/522,169 dated May 17, 2012.
Notice of Allowance in U.S. Appl. No. 12/584,528 dated Jan. 18, 2013.
Office Action in U.S. Appl. No. 12/156,959 dated Nov. 28, 2011.
Office Action in U.S. Appl. No. 12/584,528 dated May 21, 2012.
Office Action issued Apr. 18, 2012 in European Patent Application No. 08768184.7.
Office Action issued May 2, 2013 in Australian Patent Application No. 2008262388.
Office Action issued May 24, 2013 in Japanese Patent Application No. 2010-511199.
Office Action issued Nov. 16, 2012 in Japanese Patent APplication No. 2010-511199.
PCT/US2009/005065 International Search Report dated Feb. 15, 2010.
Ruedas-Rama, M. et al. "A multi-ion particle sensor", CHEMCOMM, 2007, pp. 1544-1546.
Russell, R. et al., "A Fluorescence-Based Glucose Biosensor Using Concanavalin A and Dextran Encapsulated in a Poly(ethylene glycol) Hydrogel," Anal. Chem., vol. 71, No. 15, 1999, pp. 3126-3132.
Schmidtke, D. et al. "Measurement and modeling of the transient difference between blood and subcutaneous glucose concentrations in the rat after injection of insulin", Proc. Natl. Acad. Sci., Jan. 1998, vol. 95, pp. 294-299.
Sigworth et al., "Microchip Technology in Ion-Channel Research," IEEE Trans Nanobiosci, vol. 4, No. 1, Mar. 1, 2005, pp. 121-127.
Snee, P. et al. "A Ratiometric CdSe/ZnS Nanocrystal pH Sensor", J. Am. Chem. Soc., 2006, vol. 128, pp. 13320-13321.
Springsteen, G. et al. "Alizarin Red S. as a general optical reporter for studying the binding of boronic acids with carbohydrates", CHEMCOMM Communication, 2001, pp. 1608-1609.
Tamada, J. et al. "Noninvasive Glucose Monitoring", JAMA, Nov. 17, 1999, vol. 282, No. 19, pp. 1839-1844.
Written Opinion for PCT Application No. PCT/US2006/036040, mailed Aug. 29, 2008, 7 paqes.
Written Opinion issued Feb. 15, 2010 in PCT Application No. PCT/US2009/005065.
Xu, C. et al. "Multicolor Quantum Dot Encoding for Polymeric Particle-Based Optical Ion Sensors", Anal. Chem, 2007, vol. 79, pp. 3716-3723.
Chen et al., Lighting up cancer cells with "dots", The Lancet, 364: 2001-2003 (2004).
Jia et al., "A Method to Construct a Third-Generation Horseradish Peroxidase Biosensor: Self-Assembling Gold nanoparticles to Three-Dimensional Sol-Gel Network," Anal. Chem 74: 2217-2223 (2002).
Puntener et al., "Improving the lower detection limit of potentiometric sensors by covalently binding the ionophore to a polymer backbone," Analytica Chimica Acta, 503: 187-194 (2004).
Arimori, S. et al. "A D-glucose selective fluorescent assay", Tetrahedron Letters, 2002, vol. 43, pp. 303-305.
European Office Action issued Aug. 21, 2013 in European Patent Application No. 08768184.7 (4 pages).
Office Action in U.S. Appl. No. 12/156,959 dated May 12, 2011.

* cited by examiner (a) (b)

(a) (b)

(a) (b)

(a) (b)

COATED SENSORS AND METHODS RELATED THERETO

CROSS-REFERENCE TO RELATED CASES

This application is a division of U.S. patent application Ser. No. 12/584,528, filed on Sep. 8, 2009, which claims the benefit of U.S. Provisional Patent Application No. 61/191,467 entitled "Coated Sensors and Methods Related Thereto" filed on Sep. 8, 2008, both of which are hereby incorporated by reference as if set forth herein in their entirety.

BACKGROUND OF THE INVENTION

Biological sensors are very useful for monitoring and understanding biological mechanisms, both within individual cells and in more general biological environments such as the human body: For example, intra-cellular sensors offer a powerful tool for understanding the mechanisms within a cell. Such sensors can detect the presence or concentration of an analyte within the cell, and when multiple sensors are distributed within the interior of the cell, the presence of analytes in relation to different cellular organelles and the cell membrane can be better understood.

An important consideration for sensors deployed for biological applications is compatibility with the physiological environment. Sensors in the physiological environment are extremely susceptible to nonspecific adsorption of biological materials such as proteins. This nonspecific adsorption may degrade sensor performance as well as cause inflammation and thrombosis. Therefore, methods or compositions that reduce nonspecific adsorption to biological sensors would be highly desirable.

SUMMARY OF THE INVENTION

The invention discloses coated sensors, e.g., for detecting the presence of analytes in biological media. The coating may be a polymer coating, such as a biocompatible polymer coating, e.g., that is permeable to the sensor's analyte. The coating may be substantially continuous and conformal across planar and/or nonplanar surfaces of the sensor (particularly those surfaces intended to contact the analyte solution), with thicknesses preferably ranging from approximately 50 nm to 2 µm. The coating may be formed in situ with a solventless surface polymerization process; using such methods can reduce or eliminate the presence of solvent molecules within the coating, thus attenuating or eliminating biocompatibility issues that may arise from leaching of solvent trapped in the coating into a biological environment, as well as the effects of solvent tension on coating formation, which can result in agglomeration of individual sensors and/or patchiness in the coating.

In certain embodiments, sensors and sensor particles are coated with a polymer coating deposited via initiated chemical vapor deposition (iCVD) or photoinitiated chemical vapor deposition (piCVD). In certain embodiments, the sensor coating may be biocompatible.

In certain embodiments, the subject sensors are ion-selective optodes that produce an observable optical signal indicative of the concentration of a target analyte. In certain such embodiments, the subject sensors are coated ion-selective sensors comprising quantum dots and/or fluorescent dyes and capable of selectively measuring ions, e.g., $Na^+$, $K^+$, $Cl^-$, etc., in the cytosol of a single living cell. Quantum dots are attractive probes for microscopy due to their photophysical advantages over fluorescent dyes, including prolonged photostability, brightness and quantum efficiency. In certain embodiments, a sensor comprises one or more quantum dots and/or fluorescent dye or dyes, a pH-sensitive dye, and optionally an ion-selective component such as an ionophore. These elements may, for example, be disposed in a polymer matrix and/or in the surface coating. In certain embodiments, the sensors may detect ionic analytes by selective ion extraction by the polymer matrix and/or coating, thereby inducing a pH change within the sensor which in turn changes the absorbance of the pH-sensitive dye. The change of absorbance may in turn attenuate the intensity of detectable emissions, e.g., fluorescence, from the one or more quantum dots and/or fluorescent dye or dyes by directly absorbing their fluorescence emissions.

In other embodiments, the subject sensors include coated sensors and sensor particles that may detect the presence of a chelatable analyte, such as glucose, comprising a quantum dot and/or a fluorescent dye or dyes, a polymer matrix comprising a polymer including moieties that bind the chelatable analyte, a chromophore associated with the polymer matrix that binds to the moieties in the absence of the chelatable analyte, and a surface coating. In some embodiments, photons emitted by the quantum dot in an excited state are absorbed by the chromophore in an unbound state but not by the chromophore in a bound state. The moieties may bind the chelatable analyte and chromophore reversibly and competitively. In certain embodiments, the moieties are boronic acids or boronic esters. In some embodiments, one or more components of the sensor, such as the moieties and/or chromophore, are covalently bound to or associated with the polymer matrix.

In certain aspects, the invention comprises methods for detecting the presence of an analyte in a medium using the sensors and sensor particles of the invention. In certain such embodiments, the analyte is an ion, while in other embodiments, the analyte is a chelatable analyte, such as glucose. In certain embodiments, the medium is selected from air, water, blood, plasma, urine, and cytoplasm. In certain embodiments, the invention comprises a method for detecting the presence of an analyte in a plant or animal. In certain such embodiments, the sensor particle is placed in contact with cells in biological samples such as tissues outside of the host specimen. In certain such embodiments, the sensors are introduced to cells within a host specimen. In certain such embodiments, the sensor particle is implanted in the dermis or epidermis of an animal and an analyte, such as glucose, is monitored.

In certain embodiments, the polymer matrix and/or surface coating may comprise an internalizing moiety which assists the sensor in localizing within the cytosol of a cell. In certain embodiments, the internalizing moiety comprises a small molecule or peptide, such as an amine, that reacts, e.g., under acidic conditions, to release a sensor from the confines of an endosome.

DETAILED DESCRIPTION OF THE INVENTION

Figure 1:
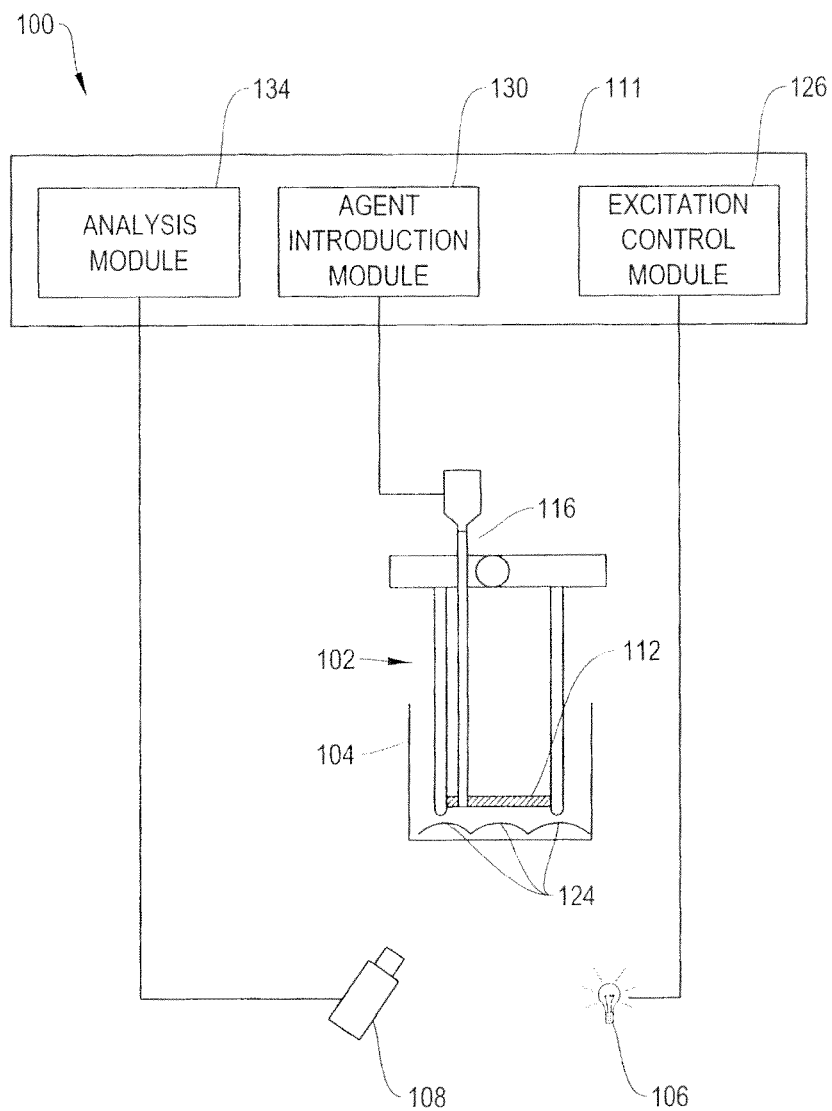
FIG. 1. A schematic diagram of a cell assay system according to an illustrative embodiment of the invention.

In brief overview, embodiments of the present invention provide coated sensors and related systems, methods, and devices for measuring ionic and/or chelatable analytes. Suitable coatings are preferably permeable to the analyte of interest. In certain embodiments, the coating acts as a barrier. Such coatings serve to protect and/or contain the functional components within the sensor, and thus may be substantially impermeable to one or more of: 1) functional components of the sensor (such as dyes, chromionophores, and other components disclosed herein), thereby inhibiting leaching of the functional components from the sensor and thereby extending the useful lifetime of the sensor; and 2) components of the analyte solution that could degrade the sensor or any of its components. In certain embodiments, the coating acts as a biocompatible coating. In certain embodiments, the coating acts both as a barrier and as a biocompatible coating.

In certain embodiments, initiated chemical vapor deposition (iCVD), a coating technology, may be used to deposit a layer that protects the sensors from the surrounding medium. The solventless nature of iCVD particle coating may offer an advantage over solution-based methods that rely on drying of a wet polymer solution. In certain embodiments, the iCVD particle coating employs a rotating bed reactor which provides conformal coating of microspheres and nanoparticles without inducing aggregation. In certain embodiments, the polymer or copolymer comprises one or more recurring monomeric units selected from

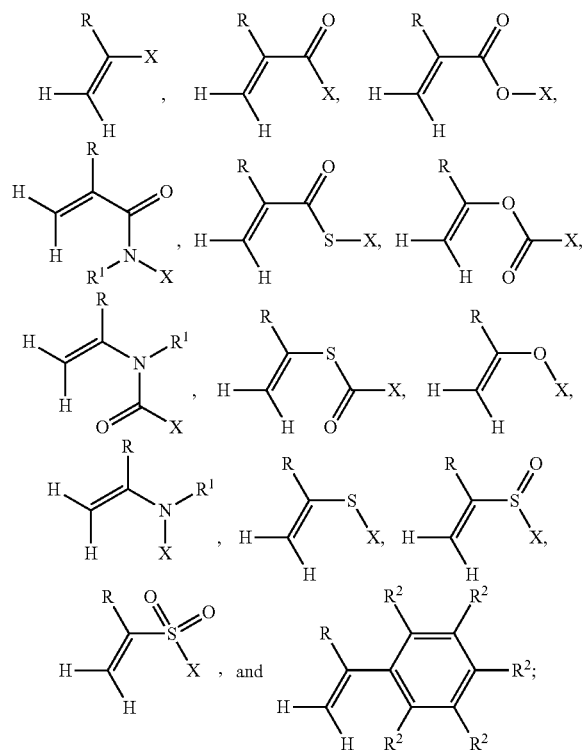

wherein, independently for each occurrence:
R is selected from hydrogen and alkyl;
$R^1$ is selected from hydrogen, alkyl, aralkyl, heteroaralkyl, and carboxyl;
$R^2$ is selected from hydrogen, methyl, bromine, and chlorine;
X is selected from hydrogen, alkyl, cycloalkyl, heterocycloalkyl, aryl, heteroaryl, aralkyl, heteroaralkyl, and —(CH$_2$)$_n$Y, wherein X is optionally substituted, e.g., by one or more of halo, alkyl, hydroxyl, and alkoxy; and
Y is selected from hydrogen, alkyl, haloalkyl such as monohaloalkyl, dihaloalkyl and perhaloalkyl, cycloalkyl, heterocycloalkyl, aryl, heteroaryl, aralkyl, heteroaralkyl, nitro, halo, hydroxyl, alkoxy, aryloxy, carboxyl, heteroaryloxy, amino, acylamino, amido, carbamoyl, sulfhydryl, sulfonate and sulfoxido; and n is 1-10 inclusive. The term "copolymer" as used herein means a polymer of two or more different monomers, including alternating, block, and random copolymers.

Unless otherwise specified, any of alkyl, cycloalkyl, heterocycloalkyl, aryl, heteroaryl, aralkyl, heteroaralkyl and any other group in which hydrogen atoms are covalently appended to carbon atoms, may optionally be substituted, i.e., substitution of hydrogen atoms, by one or more substituents such as halogen, alkyl, hydroxyl and alkoxy.

In certain embodiments, the polymer or copolymer comprises one or more recurring monomeric units selected from poly(glycidyl methacrylate), p-bromophenyl methacrylate, pentabromophenyl methacrylate, n-vinyl carbazole, p-divinyl benzene, styrene, alpha methyl styrene, 2-chlorostyrene, 3-chlorostyrene, 4-chlorostyrene, 2,3-dichlorostyrene, 2,4-dichlorostyrene, 2,5-dichlorstyrene, 2,6-dichlorostyrene, 3,4-dichlorostyrene, 3,5-dichlorostyrene, 2-bromostyrene, 3-bromostyrene, 4-bromostyrene, 2,3-dibromostyrene, 2,4-dibromostyrene, 2,5-dibromostyrene, 2,6-dibromostyrene, 3,4-dibromostyrene, 3,5-dibromostyrene, methyl acrylate, n-butyl acrylate, n-pentyl acrylate, n-hexyl acrylate, n-heptyl acrylate, n-octyl acrylate, 2-ethylhexyl acrylate, perfluorocyclohexylmethyl acrylate, perfluorodecylacrylate, pentafluorophenyl methacrylate, benzyl acrylate, 2-hydroxyethyl acrylate, dimethylaminoethyl acrylate, Et$_3$DMAA (N,N-dimethylacetoacetamide), sec-butyl acrylate, tert-butyl acrylate, isobornyl acrylate, ethylene glycol, ethylene glycol diacrylate, methyl methacrylate, ethyl methacrylate, n-propyl methacrylate, n-butyl methacrylate, isobutyl methacrylate, n-pentyl methacrylate, t-butyl methacrylate, dimethylaminoethyl methacrylate, hydroxyethyl methacrylate, cyclohexyl methacrylate, benzyl methacrylate, isobornyl methacrylate, glycidyl methacrylate, ethylene glycol dimethacrylate, methacrylic acid, styrene, alpha-methyl styrene, 2,4-dimethyl styrene, 2,5-dimethyl styrene, m-divinylbenzene, p-divinylbenzene, vinylimidazole, N-vinyl-2-pyrrolidinone, V3D3 (3901-77-7), 1,4-divinyloxybutane (3891-33-6), diethylene glycol divinyl ether (764-99-8), 1,5-hexadiene-3,4-diol DVG (1069-23-4), methyl transcinnamate, N-morpholinoethyl acrylate, 2-morpholinoethyl methacrylate, 2-isocyanatoethylmethacrylate, 2-sulfoethyl emthacrylate, 2-methoxyethyl methacrylate, 2-(tert-butylamino)ethyl methacrylate, 2-ethoxyethyl methacrylate, 2-chloroethyl methacrylate, 2-hydroxypropyl methacrylate, 2-diethylaminoethyl methacrylate, cyclopentyl methacrylate, 2-(diisopropylamino) ethyl methacrylate, 2-bromoethyl methacrylate and 2-phenylethyl methacrylate.

In certain embodiments, the polymer or copolymer comprises one or more recurring monomeric units selected from hydroxyethylmethacrylate (HEMA), perfluorodecylacrylate, ethylene glycol, and pentafluorophenyl methacrylate. In certain embodiments, the polymer or copolymer comprises one or more methacrylate monomers, e.g., HEMA and pentafluorophenyl methacrylate. In certain embodiments, the copolymer comprises HEMA and perfluorodecylacrylate, e.g. poly (HEMA-co-perfluorodecylacrylate). In certain embodiments, the copolymer comprises ethylene glycol, HEMA, and methacrylate, e.g., poly(HEMA-co-poly(ethylene glycol)ethyl ether methacrylate). In certain embodiments, the copolymer comprises HEMA and pentafluoromethacrylate, e.g., poly(HEMA-co-pentafluorophenyl methacrylate).

In certain embodiments, the polymer or copolymer comprises one or more recurring monomeric units selected from the formulas above where X is —(CR'R')$_n$Y and R' at each occurrence is selected from hydrogen or fluoro. In particular embodiments, Y is selected from haloalkyl such as perhaloalkyl such as perfluoromethyl. In particular embodiments, n is selected from 1-10, such as 9, and R' at each occurrence is fluoro. In certain embodiments, X is perfluorodecyl.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "alkyl" refers to saturated aliphatic substituents, including straight-chain alkyl groups and branched-chain alkyl groups. In preferred embodiments, a straight-chain or branched chain alkyl has 30 or fewer carbon atoms in its backbone (e.g., C1-C30 for straight chains, C3-C30 for branched chains), and more preferably 20 or fewer. Examples of straight-chain and branched alkyl groups include methyl, ethyl, n-propyl, iso-propyl, n-butyl, sec-butyl, tert-butyl, pentyl, hexyl, pentyl and octyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "Cx-y" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like.

The term "amide", as used herein, refers to a group

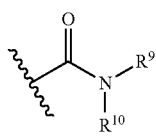

wherein $R_9$ and $R_{10}$ each independently represent a hydrogen or hydrocarbyl group, or $R_9$ and $R_{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

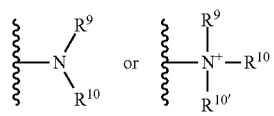

wherein $R_9$, $R_{10}$, and $R_{10}'$ each independently represent a hydrogen or a hydrocarbyl group, or $R_9$ and $R_{10}$ taken together with the N atom to which they are attached complete a heterocycle having from 4 to 8 atoms in the ring structure.

The term "aralkyl", as used herein, refers to an alkyl group substituted with an aryl group. Examples of aralkyl include benzyl, pyridinylmethyl, thiophenylbutyl, and phenethyl.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" or "carbamoyl" is art-recognized and refers to a group

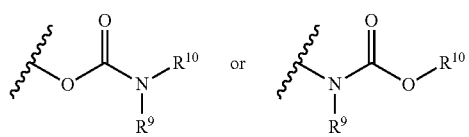

wherein $R^9$ and $R^{10}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms. Each ring of a polycicylic carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl and naphthyl.

A cycloalkyl group is a carbocycle which is completely saturated. Unless otherwise specified, cycloalkyl refers to 3-8 membered monocylic and 7-12 membered bicyclic rings. Exemplary cycloalkyl groups include cyclopentyl, cyclohexyl, bicyclo[2,2,1]heptanyl and adamantyl.

The terms "hetaralkyl" and "heteroaralkyl", as used herein, refers to an alkyl group substituted with a heteroaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a $=O$ or $=S$ substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a $=O$ substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Fluoro-substituted includes from one fluoro substituent up to per-fluoro-substitution. Exemplary fluoro-substituted $C_1$-$C_2$ alkyl includes —$CFH_2$, $CF_2H$, —$CF_3$, —$CH_2CH_2F$, —$CH_2CHF_2$, —$CHFCH_3$, —$CF_2CHF_2$. Per-fluoro-substituted $C_1$-$C_2$ alkyl, for example, includes —$CF_3$, and —$CF_2CF_3$.

The term "sulfoxide" is art-recognized and refers to the group —S(O)—$R_9$, wherein $R_9$ represents a hydrocarbyl.

The term "sulfonate" is art-recognized and refers to the group —OS(O)$_2$—$R_9$, wherein $R_9$ represents a hydrocarbyl.

In certain embodiments, photoinitiated chemical vapor deposition (piCVD), a coating technology, may be used to deposit a layer that protects the sensors from the surrounding medium. In addition to the benefits of iCVD disclosed above, piCVD has the additional advantage of not requiring a separate polymerization initiator. In certain embodiments, the piCVD particle coating employs a reactor which provides conformal coating of microspheres and nanoparticles, e.g., without inducing aggregation. In certain embodiments, the primary monomer for the piCVD coatings of sensors is hydroxyethylmethacrylate (HEMA) monomer. In certain embodiments, the piCVD coatings of sensors comprise substantially pure poly(HEMA), while in other embodiments the coatings comprise copolymers comprising HEMA and one or more of the monomers and polymers, e.g., selected from those disclosed above. In certain embodiments, the HEMA polymer or copolymer is crosslinked as a result of photodegradation of the hydroxyethyl ester.

CVD generally takes place in a reactor wherein the surface to be coated is placed on a stage in the reactor and gaseous precursor molecules are fed into the reactor. The stage may simply be the bottom of the reactor and not a separate entity. CVD provides a uniform or substantially uniform coating on rough, fibrous, and porous morphologies with high surface areas. The CVD coating process is compatible with a variety of organic and inorganic materials. Any embodiments disclosed for application with CVD may also be used with particular CVD methods such as iCVD or piCVD.

The CVD coating process can take place at a range of pressures from atmospheric pressure to low vacuum. In certain embodiments, the pressure is less than about 500 mtorr, such as less than about 400 mtorr, such as less than about 300 mtorr, such as less than about 200 mtorr, such as about 100 mtorr.

The CVD coating process can take place at a range of temperatures. In certain embodiments, the temperature is ambient temperature. In certain embodiments the temperature is about 20° C., about 25° C., about 30° C., about 35° C. or about 40° C. In certain embodiments the temperature is between about 0° C. and about 100° C., or between about 20° C. and about 50° C. In certain embodiments, the stage temperature may be varied during the coating process.

The CVD coating process can take place using a range of monomer flowrates. In certain embodiments, the properties of the resultant polymer and the speed of the deposition can be controlled by the partial pressure of a monomer, e.g., HEMA, divided by the saturation pressure of the monomer evaluated at the stage temperature, i.e. $P_M/P_M^{sat}$. In certain embodiments, $P_M/P_M^{sat}$ is between about 0.10 and about 1.0, such as about 0.2, such as about 0.3, such as about 0.4, such as about 0.5, such as about, 0.6, such as about 0.7, such as about 0.8, such as about 0.9 or in particular about 0.4.

In certain embodiments, flowrate of a monomer in the coating process may range from about 0.1 to about 3.0 standard cubic centimeters per minute (sccm) such as about 1.0, such as about 1.5, such as about 2.0, such as about 2.5 sccm. In certain embodiments, the flowrate may be varied during the coating process.

In certain embodiment, the coating process takes place at a temperature between about 20° C. and about 50° C., a pressure of about 100 mtorr, a flowrate as measured by $P_M/P_M^{sat}$ between about 0.10 and about 1.0 such as about 0.4 and ranging from about 0.5 to about 3.0 sccm such as about 2 sccm.

In certain embodiments, the coatings of the sensors or sensor particles are essentially pure polymer and little or no residual solvent is present, e.g., that may cause implant rejection, irritation, or other unwanted side effects. In certain embodiments, there may be less than 1.0%, 0.5%, 0.1%, or even less than 0.05% or 0.01% of residual solvent in the coating. The coatings may be applied at room temperature in a single step, taking only a few minutes of total time. In certain embodiments, the composition may be controlled by changing the gas feed mix and thickness may be controlled by in situ monitoring. In certain embodiments, coating film crosslinking, which affects film swelling characteristics, mesh size, and analyte permeability, may be controlled by the choice of temperature during the coating process. In certain embodiments, the coatings of the sensors are substantially conformal. In certain embodiments, the coatings of the sensors display less than 20%, 15%, 10%, 5%, or even less than 2% or 1% of thickness variation over the coated surface.

Graft density is a measure of the number of covalent bonds a polymer makes to substrate per unit contact area, and often correlates to how strongly a polymer is adhered to a substrate. In certain embodiments, the coatings of the sensors have graft densities greater than 1 chain per square millimeter, or even greater than 1 chain per square micron, e.g., ranging from 0.001 to 10 chains per square nanometer, or from 0.01 to 1 chains per square nanometer.

Free radical polymerization initiators may be used to initiate polymerization in the iCVD coating process. Free radical polymerization initiators may include halogens such as chlorine, azo compounds such as azobisisobutyronitrile (AIBN) or 1,1'-(Z)-diazene-1,2-diyldicyclohexanecarbonitrile (ABCN), or organic peroxides such as tert-butyl peroxide or benzoyl peroxide. The use of free radical polymerization initiators in a polymerization reaction may result in the formation of initiator fragments. Examples of initiator fragments may include cyanoisobutyl (from AIBN), cyanocyclohexyl (from ABCN), tert-butoxyl (from tert-butyl peroxide), or benzoyloxy (from benzoyl peroxide). In certain embodiments, coatings of sensors or sensor particles may be substantially free of initiator fragments, or may comprise less than 1.0%, 0.5%, 0.1%, or even less than 0.05% or 0.01% of initiator fragments.

In certain embodiments, the coatings are durable under usage condition, e.g., remain substantially intact after prolonged immersion in aqueous buffer solution and repeated cycling between wet and dry conditions. In certain embodiments, the coatings exhibit reversible swelling properties under repeated cycling between wet and dry states, e.g., remain substantially continuous and/or displays substantially no thickness loss between cycles, e.g., less than 40%, 30%, 20%, or even less than 10% or 1.0% thickness loss between cycles.

Varying the thickness of the coating can effect functional parameters of the sensor. Increasing the thickness will increase the transit time of an analyte through the coating into the sensor, thereby increasing the response time of the sensor. However, increasing the thickness of the coating can also enhance its protective value, potentially increasing the useful life of the sensor. Typical coating thicknesses range from 1 nm to 100 microns, e.g., 10 nm to 10 microns.

Sensor coatings may be further modified, e.g., subsequent to deposition. In certain embodiments, the sensor further comprises a surface modifier (SM). In certain embodiments, the SM comprises a molecule that promotes the delivery or localization of the sensor within a cell. SMs of the invention include molecules with a hydrophilic portion 40 and a hydrophobic portion 42, FIG. 15. In certain embodiments, the hydrophobic portion 42 of the SM anchors the SM to the hydrophobic polymer matrix 41. In certain embodiments, the SM is disposed on the surface of the sensor, e.g., covers a portion of the surface or covers the entire surface. In certain embodiments, the SM is disposed on the surface of the coated sensor, e.g., on all or a portion of the coated surface. In certain embodiments, the sensor coating may comprise the SM. Exemplary hydrophobic portions 42 of the SM include but are not limited to, lipids and hydrophobic polymers. In certain embodiments, the hydrophilic portion 40 of the SM is disposed on the surface of the sensor. An exemplary hydrophilic portion 40 includes, but is not limited to, polyethylene glycol (PEG). In certain embodiments, the hydrophilic portion (PEG) is bound to the hydrophobic portion (lipid) through a linker (e.g., phosphate, ceramide).

In certain embodiments, the sensor further comprises a targeting moiety. In certain embodiments, the targeting moiety is bound to the polymer matrix. In certain embodiments, the targeting moiety is bound to the SM on the surface of the polymer matrix. In certain embodiments, the targeting moiety is coupled to the sensor coating. In certain embodiments, the targeting moiety may be coupled to the SM, which in turn may be coupled to the surface of the polymer matrix or to the sensor coating. In certain embodiments, the sensor coating comprises the targeting moiety. The targeting moiety, which assists the sensor in localizing to a particular target area, entering a target cell(s), and/or locating proximal to an ion channel, may be selected on the basis of the particular condition or site to be monitored. The targeting moiety may comprise any of a number of different chemical entities. In one embodiment, the targeting moiety is a small molecule. Molecules which may be suitable for use as targeting moieties in the present invention include haptens, epitopes, and dsDNA fragments and analogs and derivatives thereof. Such moieties bind specifically to antibodies, fragments or analogs thereof, including mimetics (for haptens and epitopes), and zinc finger proteins (for dsDNA fragments). Nutrients believed to trigger receptor-mediated endocytosis and therefore useful targeting moieties include biotin, folate, riboflavin, carnitine, inositol, lipoic acid, niacin, pantothenic acid, thiamin, pyridoxal, ascorbic acid, and the lipid soluble vitamins A, D, E and K. Another exemplary type of small molecule targeting moiety includes steroidal lipids, such as cholesterol, and steroidal hormones, such as estradiol, testosterone, etc.

In another embodiment, the targeting moiety may comprise a protein. Particular types of proteins may be selected based on known characteristics of the target site or target cells. For example, the probe can be an antibody either monoclonal or polyclonal, where a corresponding antigen is displayed at the target site. In situations wherein a certain receptor is expressed by the target cells, the targeting moiety may comprise a protein or peptidomimetic ligand capable of binding to that receptor. Proteins ligands of known cell surface receptors include low density lipoproteins, transferrin, insulin, fibrinolytic enzymes, anti-HER2, platelet binding proteins such as annexins, and biological response modifiers (including interleukin, interferon, erythropoietin and colony-stimulating factor). A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are $F(ab')_2$, Fab', Fab, and $F_v$ fragments, which may be produced by conventional methods or by genetic or protein engineering.

Other preferred targeting moieties include sugars (e.g., glucose, fructose, galactose, mannose) that are recognized by target-specific receptors. For example, instant claimed constructs can be glycosylated with mannose residues (e.g., attached as C-glycosides to a free nitrogen) to yield targeted constructs having higher affinity binding to tumors expressing mannose receptors (e.g., glioblastomas and gangliocytomas), and bacteria, which are also known to express mannose receptors (Bertozzi, C R and M D Bednarski Carbohydrate Research 223:243 (1992); J. Am. Chem. Soc. 114:2242, 5543 (1992)), as well as potentially other infectious agents. Certain cells, such as malignant cells and blood cells (e.g., A, AB, B, etc.), display particular carbohydrates, for which a corresponding lectin may serve as a targeting moiety.

In certain embodiments, the sensor may comprise an internalizing moiety such as a polypeptide or small molecule. In certain embodiments, the sensor may comprise an internalizing polypeptide sequence, such as antepennepadia protein, mastoparan (T. Higashijima et al. (1990) J. Biol. Chem. 265: 14176), melittin, bombolittin, delta hemolysin, pardaxin, *Pseudomonas* exotoxin A, clathrin, Diphtheria toxin, C9 complement protein, or a fragment of one of the preceding proteins. In certain embodiments, the internalizing moiety is not the HIV transactivating (Tat) protein. In certain embodiments, the internalizing moiety is bound to one or more of the other elements of the sensor. In one embodiment of the invention, the internalizing moiety serves as the targeting moiety (examples of such targeting moieties included herein). An internalizing moiety is capable of crossing a cellular membrane by, e.g., transcytosis, at a relatively high rate, and thereby promotes cellular uptake or endosomal escape of molecules to which they are attached. In certain embodiments, the internalizing moiety crosses the membrane of intra- or extra-cellular vesicles such as endosomes or lysosomes. In certain such embodiments, sensors comprising internalizing moieties are able to escape endosomal vesicles while sensors that lack internalizing moieties are sequestered from the cellular medium inside such vesicles. In such embodiments, the sensor comprising an internalizing moiety can be situated to monitor analytes in the cytosol of the cell. Certain internalizing polypeptides are also known to localize to the nucleus or other cellular structures. Thus a sensor of the present invention which includes such an internalizing peptide sequence may exhibit increased uptake by target cells relative to sensors that lack such a sequence.

The internalizing polypeptide may be part of the targeting moiety or a separate element of the sensor. In one embodiment of the invention, the internalizing polypeptide serves as the targeting moiety (see examples above of such targeting moieties). In another embodiment, the internalizing polypeptide is covalently linked to one or more of the other elements of the sensor. For example, the internalizing polypeptide can be linked to any one or more of the targeting moiety, the polymer matrix, the surface coating, and the surface modifier. The preferred location of an internalizing polypeptide in a sensor can be determined, e.g., by conducting in vitro assays using target cells, and detecting the sensor signal that is incorporated into the cells or in specific regions within cells.

In one embodiment, the internalizing peptide is derived from the drosophila antepennepadia protein, or homologs thereof. The 60 amino acid long homeodomain of the homeoprotein antepennepadia has been demonstrated to translocate through biological membranes and can facilitate the translocation of heterologous polypeptides to which it is couples. See for example Derossi et al. (1994) J Biol Chem 269: 10444-10450; Perez et al. (1992) J Cell Sci 102:717-722. Recently, it has been demonstrated that fragments as small as 16 amino acids long of this protein are sufficient to drive internalization. See Derossi et al. (1996) J Biol Chem 271: 18188-18-193. The present invention contemplates a sensor comprising at least a portion of the antepennepadia protein (or homolog thereof) sufficient to increase the transmembrane transport of the sensor, relative to the sensor alone, by a statistically significant amount.

While not wishing to be bound by any particular theory, it is noted that hydrophilic polypeptides may be also be physiologically transported across the membrane barriers by coupling or conjugating a component of the sensor to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis. Preferred growth factor-derived internalizing peptides include EGF (epidermal growth factor)-derived peptides, such as CMHIESLDSYTC (SEQ ID NO: 2) and CMYIEALDKYAC (SEQ ID NO: 3); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides. Hydrophilic polypeptides can be bound to a component of the sensor, or they can constitute the targeting moiety.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of sensors, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA (EALA)4-EALEALAA-1-amide (SEQ ID NO: 4), which represents a modification of the peptide sequence of Subbarao et al. (Biochemistry 26:2964 (1987)). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention includes hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of a covalently linked sensor into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore forming proteins or peptides may be obtained or derived from, for example, C9 complement protein, cytolytic T-cell molecules or NK-cell molecules. These moieties are capable of forming ring-like structures in membranes, thereby allowing transport of attached sensors through the membrane and into the cell interior.

Mere membrane intercalation of an internalizing peptide may be sufficient for translocation of a sensor across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO: 5) (Eubanks et al. (1988) Peptides. Chemistry and Biology, Garland Marshall (ed.), ESCOM, Leiden 566-69). In this construct, an internalizing, peptide would be attached to the C-terminus of the accessory peptide, since the N-terminal glycine is critical for the accessory moiety's activity. This hybrid peptide, upon attachment to a sensor component is N-myristylated and will be translocated across the cell membrane.

In certain embodiments the internalizing moiety comprises an amine group. In certain such embodiments, an amine group is bound to any component of the sensor such as the polymer matrix, the surface coating, the surface modifier, the targeting moiety or any combination thereof. The amine group may have advantages in increasing release of nanosensors into the cytosol. One of the unique characteristics of endocytosis that previous studies and methods have exploited is the gradual decrease in compartment pH as the endosome passes from early stage to late stage and eventually forms a lysosome. The amine group is capable of exploiting this phenomenon by protonating as the pH decreases. When the pH of the endosome drops to around 5 most of the amine groups will be protonated. This charge may be sufficient enough to lyse the membrane of the endosome and release the components.

In certain embodiments, the invention comprises methods of preparing sensors or sensor particles selective for an analyte, comprising combining a fluorescence source, a polymeric matrix, and an analyte-sensitive component. In certain embodiments, the analyte-sensitive component detects ions. In certain embodiments, the analyte-sensitive component detects chelatable analytes, such as glucose. In certain embodiments, the method further comprises coating the polymer matrix with a coating layer, such as a biocompatible coating.

In certain embodiments, the subject sensors comprise a polymer matrix, e.g., as a body or substrate in which one or more functional components are disposed, e.g., within the coating layer. In certain embodiments, the polymer comprises poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly (D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, silicones, polyalkylenes such as polyethylene, polypropylene, and polytetrafluoroethylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, poly (propylene fumarate), polyoxymethylene, poloxamers, poly (ortho)esters, poly(butyric acid), poly(valeric acid), poly (lactide-co-caprolactone), trimethylene carbonate, polyvinylpyrrolidone, and the polymers described in Shieh et al., 1994, J. Biomed. Mater. Res., 28, 1465-1475, and in U.S. Pat. No. 4,757,128, Hubbell et al., U.S. Pat. Nos. 5,654,381; 5,627,233; 5,628,863; 5,567,440; and 5,567,435. Other suitable polymers include polyorthoesters (e.g. as disclosed in Heller et al., 2000, Eur. J. Pharm. Biopharm., 50:121-128), polyphosphazenes (e.g. as disclosed in Vandorpe et al., 1997, Biomaterials, 18:1147-1152), and polyphosphoesters (e.g. as disclosed in Encyclopedia of Controlled Drug Delivery, pp. 45-60, Ed. E. Mathiowitz, John Wiley & Sons, Inc. New York, 1999), as well as blends and/or block copolymers of two or more such polymers. The carboxyl termini of lactide- and glycolide-containing polymers may optionally be capped, e.g., by esterification, and the hydroxyl termini may optionally be capped, e.g., by etherification or esterification. In certain embodiments, the polymer comprises or consists essentially of polyvinyl chloride (PVC), polymethyl methacrylate (PMMA) and decyl methacrylate or copolymers or any combination thereof.

In certain embodiments, the polymer comprises a biocompatible polymer, e.g., selected from poly(caprolactone) (PCL), ethylene vinyl acetate polymer (EVA), poly(ethylene glycol) (PEG), poly(vinyl acetate) (PVA), poly(lactic acid) (PLA), poly(glycolic acid) (PGA), poly(lactic-co-glycolic acid) (PLGA), polyalkyl cyanoacrylate, polyethylenimine, dioleyltrimethyammoniumpropane/dioleyl-sn-glycerol-phosphoethanolamine, polysebacic anhydrides, polyurethane, nylons, or copolymers thereof. In polymers including lactic acid monomers, the lactic acid may be D-, L-, or any mixture of D- and L-isomers. In certain aspects, the biocompatible polymer comprises a PEG-lipid. In certain such embodiments, the lipid tail self-inserts into the lipophilic polymer matrix during fabrication, leaving the PEG headgroup on the surface of the sensor, e.g., to provide a hydrophilic, biocompatible coating that can be penetrated by the analyte. In certain embodiments, different chemical moieties, such as amines, can be put on the surface or further modified to attach antibodies or other recognition units.

The terms "biocompatible polymer" and "biocompatibility" when used in relation to polymers are art-recognized. For example, biocompatible polymers include polymers that are neither themselves toxic to the host (e.g., a cell, an animal, or a human), nor degrade (if the polymer degrades) at a rate that produces monomeric or oligomeric subunits or other byproducts at toxic concentrations in the host. Consequently, in certain embodiments, toxicology of a biodegradable polymer intended for intracellular or in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90%, 85%, 80%, 75% or even less of biocompatible polymers, e.g., including polymers and other materials and excipients described herein, and still be biocompatible.

The polymer matrix of the sensor may comprise a plasticizer, such as dioctyl sebacate (DOS), o-nitrophenyl-octylether, dimethyl phthalate, dioctylphenyl-phosphonate, dibutyl phthalate, hexamethylphosphoramide, dibutyl adipate, dioctyl phthalate, diundecyl phthalate, dioctyl adipate, dioctyl sebacate, or other suitable plasticizers. In certain embodiments, the plasticizer is poly(glycerol sebacate), PGS.

In certain embodiments, e.g., particularly where the polymer is biocompatible, a biocompatible plasticizer is used. The term "biocompatible plasticizer" is art-recognized, and includes materials which are soluble or dispersible in the relevant polymer, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyltrihexyl citrate (c. 20 weight percent or less), butyl benzyl phthalate, dibutylphthalate, dioctylphthalate, n-butyryl tri-n-hexyl citrate, diethylene glycol dibenzoate (c. 20 weight percent or less) and the like.

In certain embodiments, the sensor or sensor particle comprises a coating layer, such as a barrier layer or a biocompatible coating. In certain such embodiments, the biocompatible coating comprises a biocompatible polymer.

Sensors of the invention typically comprise a fluorescent component, such as one or more quantum dots or one or more fluorescent dyes. In various embodiments, a fluorescent dye can be used as a source of fluorescence in place of a quantum dot or vice versa. In certain embodiments, a sensor comprises at least one quantum dot and/or at least one fluorescent dye, a chromophore, and a polymer matrix. In certain embodiments, the photons emitted by the quantum dot and/or fluorescent dye in an excited state are absorbed by a chromophore in the presence of the analyte but not absorbed by a chromophore in the absence of the analyte. In certain other embodiments, the photons emitted by the quantum dot and/or fluorescent dye in an excited state are absorbed by a chromophore in the absence of the analyte but not absorbed by a chromophore in the presence of the analyte.

Quantum dots are fluorescent semiconductor nanocrystals having a characteristic spectral emission, which is tunable to a desired energy by selection of the particle size, size distribution and composition of the semiconductor nanocrystal. The emission spectra of a population of quantum dots have linewidths as narrow as 25-30 nm, depending on the size distribution heterogeneity of the sample population, and lineshapes that are symmetric, gaussian or nearly gaussian with an absence of a tailing region. Advantageously, the range of excitation wavelengths of the quantum dots is broad. Consequently, this allows the simultaneous excitation of varying populations of quantum dots in a system having distinct emission spectra with a single light source, e.g., in the ultraviolet or blue region of the spectrum. Fluorescent dyes may include any fluorescent compound, such as a dye. Preferably, the emissions of a fluorescent dye used as a fluorescence source are not substantially affected by the analyte or other components of test solutions.

In certain embodiments, quantum dots of the sensors described herein are, for example, inorganic crystallites between 1 nm and about 1000 nm in diameter, preferably between about 2 nm and about 50 nm, more preferably about 5 nm to 20 nm, such as about 6, 7, 8, 9, 10, 11, 12, 13, 14, 15, 16, 17, 18, 19, or 20 nm. Such quantum dots include a "core" of one or more first semiconductor materials, and which may be surrounded by a "shell" of a second semiconductor material. A semiconductor nanocrystal core surrounded by a semiconductor shell is referred to as a "core/shell" semiconductor nanocrystal. The surrounded "shell" will most preferably have a bandgap greater than the bandgap of the core material and can be chosen so to have an atomic spacing close to that of the "core" substrate. The core and/or the shell material can be a semiconductor material including, but not limited to, those of the group II-VI (ZnS, ZnSe, ZnTe, CdS, CdSe, CdTe, HgS, HgSe, HgTe, MgTe and the like) and III-V (GaN, GaP, GaAs, GaSb, InN, InP, InAs, InSb, AlAs, AlP, AlSb, AlS, and the like) and IV (Ge, Si, Pb and the like) materials, and an alloy thereof, or a mixture thereof.

In certain embodiments, a sensor comprises exactly one quantum dot, while in other embodiments, a sensor comprises more than one quantum dot, for example, 2, 3, 4, or 5 quantum dots. In certain embodiments wherein the sensor comprises more than one quantum dot, the sensor comprises two or more types of quantum dots, each type having a distinct emission wavelength, e.g., independently selected from, for example, 490, 520, 545, 560, 580, 620, 655 nm. The availability of two distinct wavelength emissions (e.g., one or more quantum dots of wavelength 545 nm and one or more quantum dots with emission wavelength of 655 nm) may allow improvements in recording of changes in ion concentration by using the ratio of the two distinct signals. Fluctuations in fluorescence that are common to both signals should theoretically cancel in a ratio. The detectable fluorescence emission of the quantum dot particles may fluctuate depending on variables including number of quantum dots, quantum dot location within the cell, photobleaching, and possible changes in excitation light intensity, all effects that can occur slowly and are not related to ion presence or concentration. Therefore, effects including number of quantum dots, quantum dot location within the cell, photobleaching, and possible changes in excitation light intensity may be attenuated.

The quantum dot of the sensor particle may be modified with a surface modifier, e.g., to alter one or more properties of the sensor particle, such as solubility, biocompatibility, or hydrophilicity/hydrophobicity. In certain embodiments, the surface modifier comprises one or more ligands that can bind reversibly with the quantum dot, while in other embodiments, the surface modification may be essentially irreversible. In certain embodiments, the surface modifier improves the lipophilicity of the quantum dot. In certain such embodiments, the ligand comprises an alkane such as decane-thiol.

In certain embodiments, the fluorescence signal of the quantum dot or fluorescent dye may trigger a detectable event within the cell. For example, fluorescence may in turn excite a secondary dye or quantum dot in the particle that easily generates reactive oxygen species (ROS). The ROS would then attack the cell, effectively stimulating necrosis (cell death), which may then be detected either visually or using markers sensitive to cell death. Alternatively, instead of including a secondary component within the particle, another particle may be added to the cell or cell culture. This additional particle may, for example, comprise a photo-degradable polymer membrane. When the primary sensor fluoresces, the emitted light will rupture the secondary particle, releasing its contents. The contents may, for example, be a drug that is therapeutic or apoptotic, e.g., triggering another detectable event.

In other exemplary embodiments, sensors comprise sensor particles for the detection of chelatable analytes, e.g., glucose. These sensor particles comprise a polymer matrix, a surface coating, moieties which bind a chelatable analyte, and a component that emits or absorbs photons of a particular wavelength either in the presence of absence of the chelatable analyte. In an exemplary embodiment, a chromophore absorbs photons of one wavelength when bound to the moieties of the sensor and another wavelength when unbound from the moieties. When the chromophore-bound moieties are exposed to the chelatable analyte, the chromophore is released and the chelatable analyte binds to the moieties. The free chromophore appears as a different color than the bound chromophore, a change which can be monitored visually or with spectrophotometric instrumentation. In an alternate exemplary embodiment, wherein the inner-filter effect is employed, the sensor particle of the preceding embodiment further comprises a fluorescent dye and/or quantum dot. The fluorescent dye and/or quantum dot absorbs a broad range of wavelengths and emits photons of a narrow range of wavelengths. The fluorescence emitted by the fluorescent component is either absorbed or not absorbed depending on the presence of the chelatable analyte. For example, when the chelatable analyte is bound to the moieties of the sensor, the fluorescence of the quantum dot is absorbed while no absorbance occurs in the absence of the chelatable analyte.

Figure 2:
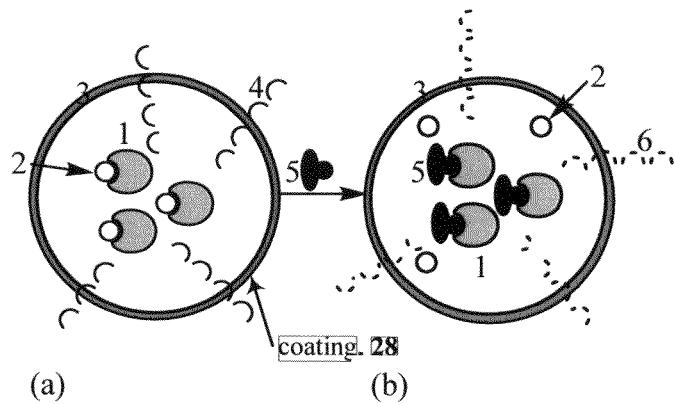
FIG. 2. Sensor particle 3, coated with a coating 28, with (a) chromophore 2 bound to moiety 1, wherein the bound chromophore emits photons 4 at one wavelength and (b) moiety 1 bound to analyte 5 wherein the unbound chromophore 2 emits photons at a second wavelength 6.

In certain embodiments, the sensor particle for detecting the presence of chelatable analytes comprises a surface coating and a polymer matrix comprising a polymer including moieties that bind the chelatable analyte and a chromophore associated with the polymer matrix that binds to the moieties in the absence of the chelatable analyte. In certain embodiments, the chelatable analyte is glucose and the moieties bind glucose and the chromophore reversibly and competitively. In an exemplary embodiment, the sensor particle 3 comprises a coating 28 and a polymer matrix with moieties 1 that can bind both a chromophore 2 and glucose 5 (FIG. 2). In a first mode, the moieties 1 are bound to a chromophore 2 and the chromophore, in its bound mode, absorbs photons at a first wavelength 4. In a second mode, when the sensor particle 3 is contacted with glucose 5, the glucose 5 binds to the moieties 1, displacing the chromophore 2 which, in its unbound state, absorbs photons at a second wavelength 6. In certain embodiments, the sensor 3 is monitored visually to determine a change in the color of the chromophore 2. In certain embodiments, the sensor 3 is monitored with spectrophotometric instrumentation to determine the emission spectra of the chromophore 2.

In certain embodiments, the sensor particle for detecting the presence of a chelatable analyte comprises a surface coating, a fluorescent component, a polymer matrix comprising a polymer including moieties that bind the chelatable analyte and a chromophore associated with the polymer matrix that binds to the moieties in the absence of the chelatable analyte. In certain embodiments, the sensor particle emits photons with an inner filter effect. The inner-filter effect has been documented as a way to increase the signal intensity and concomitant sensitivity of ion-selective optical sensors (optode). In brief, a secondary, inert fluorescent component is added to the polymer matrix of the optode. When the concentration of analyte in the optode changes, the fluorescence intensity of the inert dye itself does not respond, however the absorbance of the sensor does. Because the fluorescence emission has been carefully chosen to overlap with the absorbance spectrum of the sensor, the emission from the inert dye is then absorbed by the sensor. The attenuation of the fluorescence output of the inert dye is therefore directly related to the concentration of the ion of interest in solution.

Figure 4:
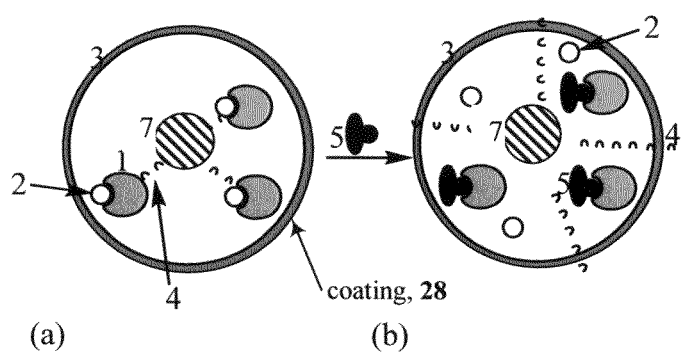
FIG. 4. Sensor particle 3, coated with a coating 28 with a. chromophore 2 bound to moiety 1, wherein the bound chromophore absorbs photons 4 emitted by the quantum dot and/ or fluorescent dye 7 and b. moiety 1 bound to analyte 5 wherein unbound chromophore 2 absorbs photons 4 emitted by quantum dot and/or fluorescent dye 7.
Figure 5:
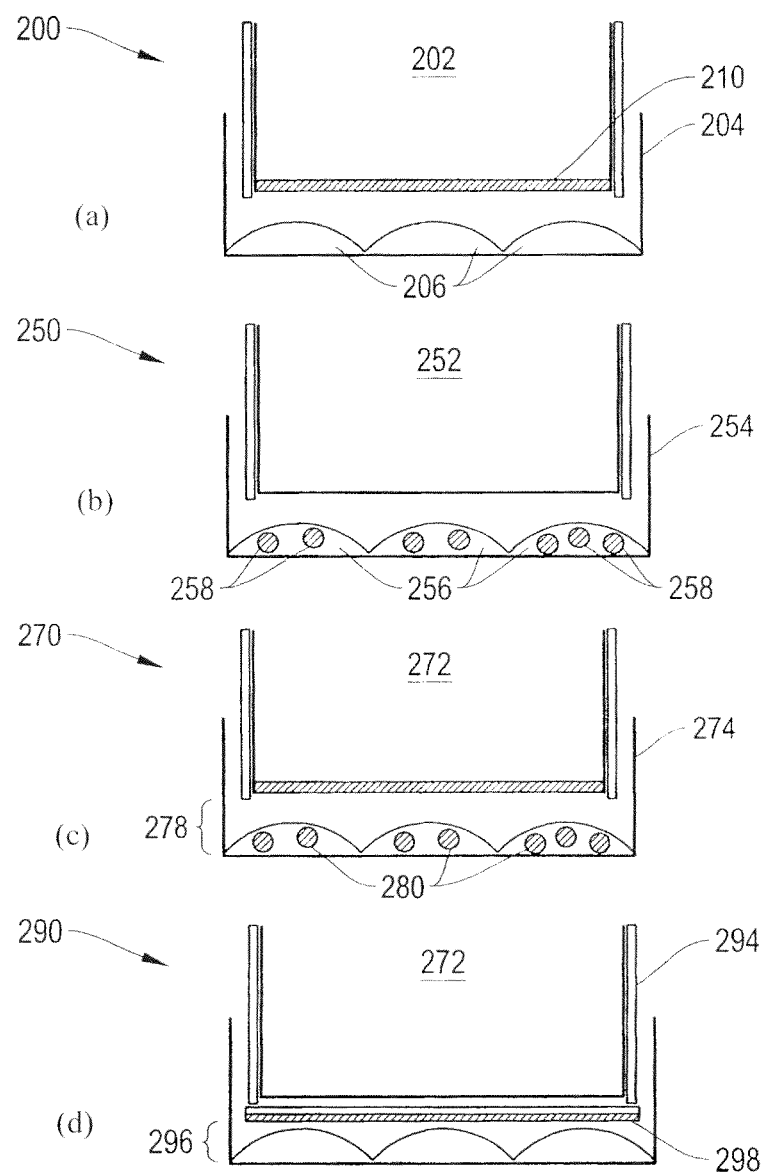
FIG. 5. Cross sections (a-d) of various optical sensor arrangements suitable for use in various implementations of a cell assay system.
Figure 6:
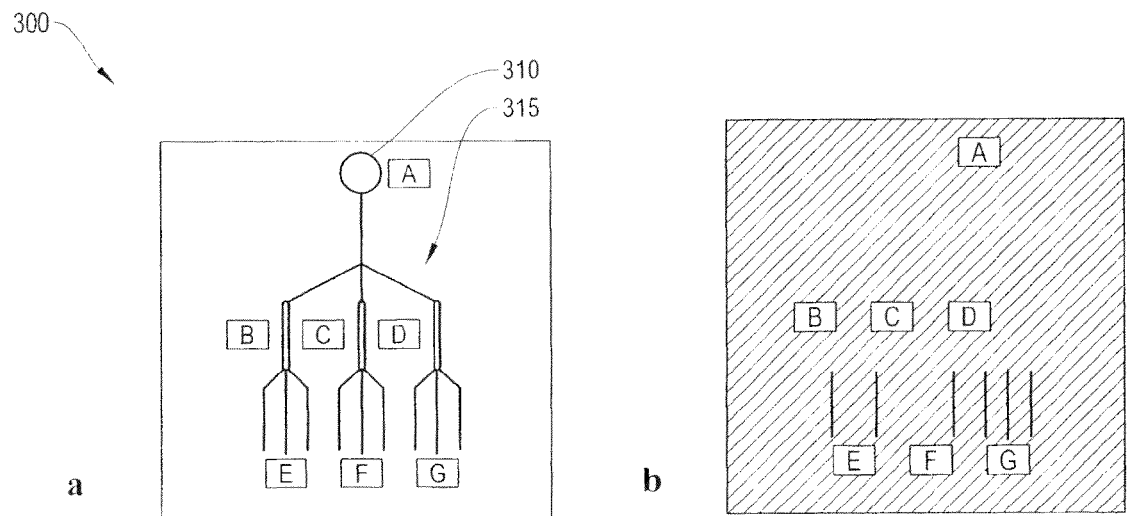
FIG. 6. An embodiment (a-b) of a microfluidic device in accord with the present invention.
Figure 7:
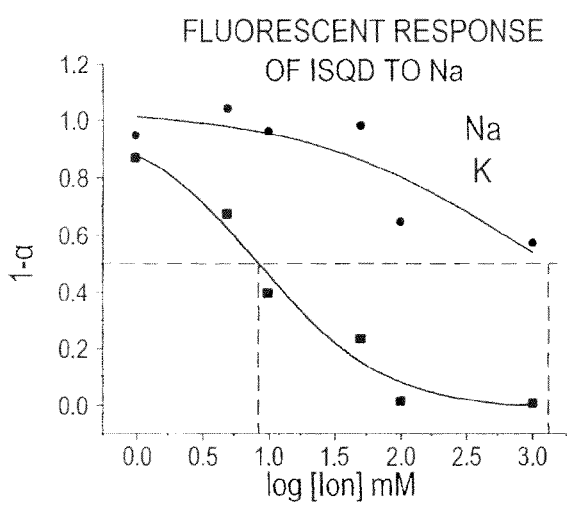
FIG. 7. Selectivity of the nanosensor of the invention for ion detection.
Figure 8:
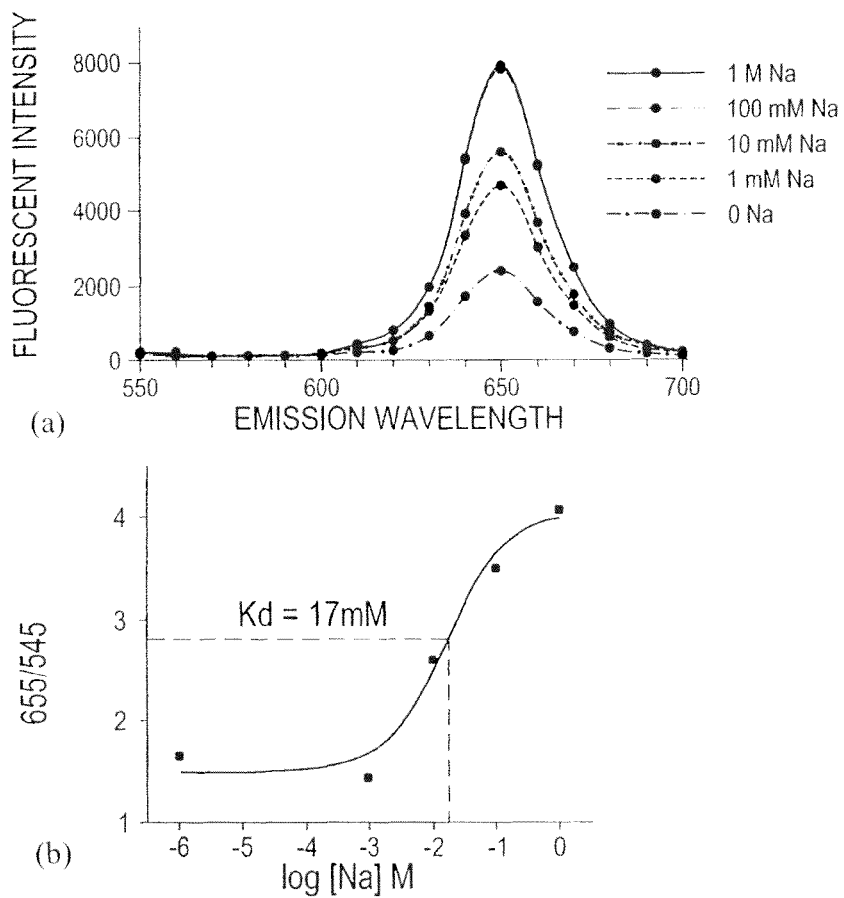
FIG. 8. Experimental response to sodium. (a) Spectral response of immobilized sensors to increasing concentrations of sodium. (b) Calibration curve of ratiometric sensors.
Figure 9:
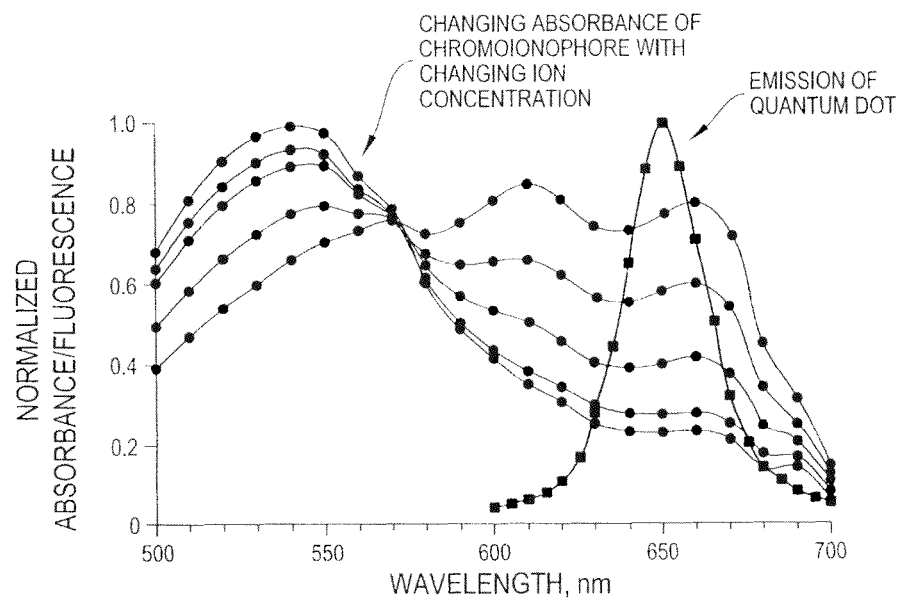
FIG. 9. Spectral overlap of a quantum dot that fluoresces at 655 nm and the absorbance of a chromoionophore at varying sodium concentrations.

In certain embodiments, the chelatable analyte is glucose and the moieties bind glucose and the chromophore reversibly and competitively. In certain embodiments, the fluorescent component is selected from one or more quantum dots and/or fluorescent dyes 7. In certain such embodiments, a sensor particle 3 comprises a coating 28 and a fluorescent component 7, and a polymer matrix with moieties 1 that can bind both a chromophore 2 and glucose 5. In certain such embodiments, the fluorescent component 7 absorbs a broad range of wavelengths of photons but emits a narrow range of wavelengths of photons. The fluorescent component 7 is activated by exciting with a light source, e.g., UV light. The fluorescence emitted from the excited fluorescent component 7 is either absorbed by a component of the sensor, e.g., the chromophore 2 or the glucose-moiety complex, or emitted from the sensor 3 without being attenuated. In certain embodiments, photons 4 of the fluorescent component 7 are absorbed when the chromophore 2 is bound to the moieties 1 (FIG. 4, left). In certain such embodiments, the absence of fluorescence emitted from the sensor particle 3 indicates an absence of glucose molecules 5, i.e. glucose molecules are not bound to the moieties of the sensor. In such embodiments, when glucose 5 is introduced, the moieties 1 bind glucose 5, releasing the chromophore 2. The photons 4 of the fluorescent component 7 are no longer absorbed by a component of the sensor, FIG. 4, right. By detecting the emitted photons, the amount of bound glucose can be calculated relative to a standard.

Figure 3:
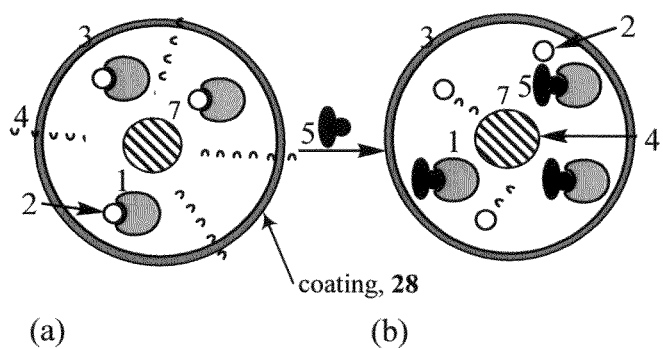
FIG. 3. Sensor particle 3, coated with a coating 28 with (a) chromophore 2 bound to moiety 1, wherein the bound chromophore 2 does not absorb photons 4 emitted by the quantum dot and/or fluorescent dye 7 and (b) moiety 1 bound to analyte 5 wherein unbound chromophore 2 absorbs photons 4 emitted by quantum dot and/or fluorescent dye 7.

In certain embodiments, a component of the sensor, e.g., the chromophore 2 or the glucose-moiety complex, absorbs photons 4 of the fluorescent component 7 when unbound from the moieties 2 (FIG. 3, right). In certain such embodiments, the detection of photons 4 from the sensor 3 indicates the absence of glucose 5, i.e., glucose molecules are not bound to the moieties of the sensor. In certain such embodiments, when the sensor 3 is contacted with glucose 5, the moieties 1 release the chromophore 2 and bind glucose 5. In such embodiments, the photons 4 of the fluorescent component 7 are not absorbed when glucose 5 is bound to the moieties 1 such that the detection of photons 4 emitted from the sensor particle 3 indicates the presence of glucose 5.

In certain embodiments, the sensors of the present invention may be used to detect and measure the presence of a wide variety of chelatable analytes, e.g., sugars and related compounds, in a solution, in vitro or in vivo. The sensor may be located within a cell, i.e., intracellular, or exterior to a cell, i.e., extracellular. In certain embodiments, the sensor is in contact with the cell membrane such as within a cell or exterior to a cell. Exemplary chelatable analytes for detection by the sensor of the present invention include sugars such as glucose, mannose, and other monosaccharides, sialic acid, lactic acids, aminosugars, such as glucosamine, disaccharides, trisaccharides, oligosaccharides, sugar-amino acids, sugar-peptides and glycoproteins. Other exemplary chelatable analytes include, but are not limited to, glycerol, dopamine, catechols, ascorbic acid, polyols, diols such as 1,4-anhydroerythritol and ethylene glycol. The concentration range of chelatable analytes which is typically of interest in biological samples is 0-25 mM, such as from 5-20 mM, such as from 5-10 mM, such as from 0-5 mM.

In certain embodiments, the moieties that bind the chelatable analytes comprise a dihydroxide component, e.g., boron and alkali earth dihydroxides. Complexation of sugars, for example, with boron and alkali earth dihydroxides has been reported in, among other sources, [S. A. Barker et al., Carbohydrate Research, 26 (1973) 33-40; N. Roy et al., Carbohydrates Research, 24 (1972) 180-183]. A variety of different boronic acids, having the structure $RB(OH)_2$ may be used to chelate the analyte. R can be, for example, an aryl or a saturated or unsaturated alkyl moiety, either of which can be substituted or unsubstituted and can contain one or more heteroatoms, e.g., N, S, O, P, B, F, Br. In certain embodiments, a boronic ester is used to chelate the analyte. Boronic esters have the molecular formula $RB(OR')_2$ wherein R' is typically an alkyl group and R can be defined as above. Under aqueous conditions, many boronic esters hydrolyze to form boronic acids. Therefore, OR' groups that hydrolyze to OH are of use in the present invention. The two R' groups of the ester may be linked to form a cyclic structure, e.g., $—CH_2CH_2—$. In certain embodiments, the moieties are selected from one ore more aromatic or aliphatic boronic esters. In certain aspects, boronic acids are appended with substituents that affect the pKa such as electron withdrawing groups or electron donating groups. In certain embodiments the $pK_a$ of the boronic acid will change the dynamic range of the sensor. In certain embodiments the dynamic range of the sensor relates to the affinity for an analyte, such as glucose. In certain embodiments, the moieties are selected from one or more aromatic or aliphatic boronic acids. Exemplary boronic acid moieties of the invention include phenyl boronic acid, butyl boronic acid, (3,5-dichlorophenyl)boronic acid, [3,5-bis(trifluoromethyl)phenyl]boronic acid, and (4-bromophenyl)boronic acid.

In certain embodiments, the moieties of the sensor which chelate the analytes comprise a metal ion. The ability of sugars, for example, and other molecules to form chelate complexes with metal ions in aqueous solution is well known (general review by: Whitfield, D. M. et al., "Metal coordination to carbohydrates. Structure and Function," *Coord. Chem. Reviews* 122, 171-225 (1993) and Angya, S. J. Complexes of Metal Cations with Carbohydrates in Solution, in "*Advances in Carbohydrate Chemistry and Biochemistry*," Academic Press, Inc. 1989, pp. 1-4). The complexation of Cu (II) with various sugar α-amino acids is described by M. Angeles Diaz-Diez et al., *Transition Met. Chem.* 20, 402-405, 1995. Sugar-α-amino acid compounds will also form complexes with Co (II), Ni (II), Zn (II) and Cd (II) (M. Angeles Diaz-Diez et al., *J. Inorg. Biochem.* 56, 243-247, 1994). Additionally, complexes of various sugars with vanadium, molybdenum, tungsten, aluminum, iron, barium, magnesium, and strontium are known (Sreedhara, A. et al., *Carbohydrate Res.* 264, 227-235, 1994; Caldeira, M. M. et al., *Inorg. Chim. Acta.* 221, 69-77, 1994; Tonkovic, M. and Bilinski, H., *Polyhedron* 14, 1025-1030, 1995; Nagy, L. et al., *Inorg. Chim. Acta.* 124, 55-59, 1986; Tajmir-Riahi, H. A., *Inorg. Chim. Acta.* 119, 227-232, 1986; and Tajmir-Riahi, H. A., *J. Inorg. Biochem.*, 24, 127-136, 1985.

In certain embodiments, the moieties that bind the chelatable analytes are covalently conjugated to the polymer matrix, the surface coating, or both, for example, through a linker molecule. In an exemplary embodiment, the moieties comprise aryl boronic acids which are covalently conjugated to the polymer matrix through ester linkages originating at an aryl atom or the aryl boronic acid. Other exemplary linkages include amides, ethers, sulfonates, thioethers, thioesters and carbonates. In certain embodiments, the moieties are covalently bound to the polymer matrix through a bond such as a single or double bond. In certain exemplary embodiments, the aryl boronic acids are covalently bound to the polymer matrix through a single bond originating from an aryl atom or the aryl boronic acid.

In certain embodiments, the chromophore of the sensor is any molecule that binds reversibly to the moieties of the sensor, e.g., the chromophore alizarin binds boronic acids, and absorbs photons of the fluorescent component in a first state and does not absorb photons of the fluorescent component in a second state. The states of the chromophore include bound to the moieties and unbound from the moieties. For example, the chromophore alizarin absorbs at a first wavelength when unbound and a second wavelength when bound to a boronic acid. The following depits an exemplary interaction between alizarin and a boronic acid:

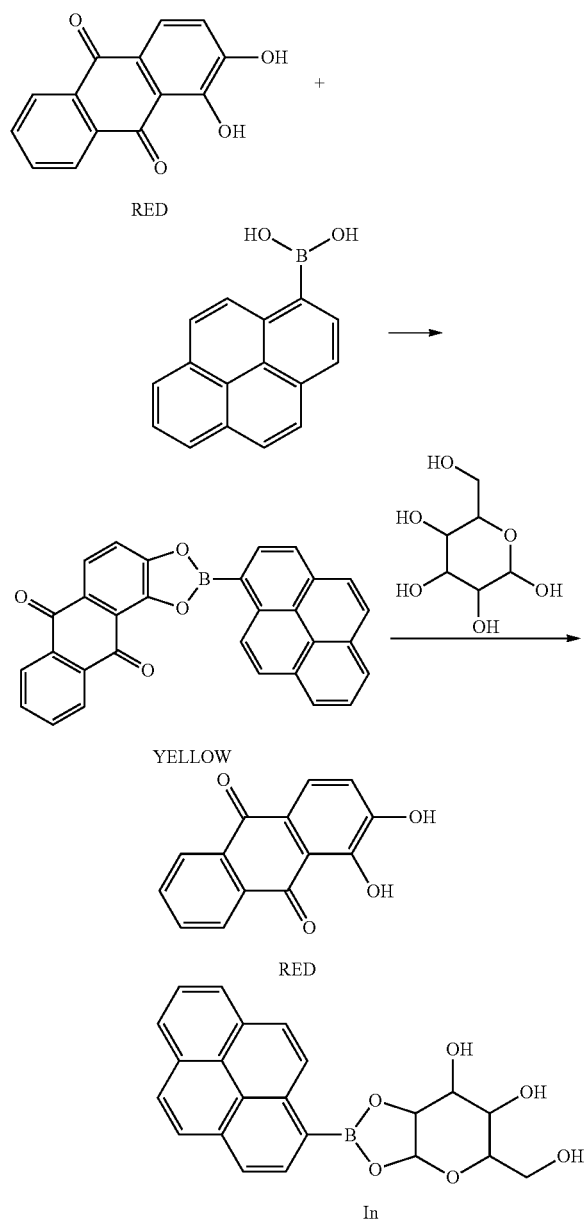

| Chromophore | CAS Reg. No. | Color | Abs. Max. |
|---|---|---|---|
| Yellow No. 5 | 1934-21-0 | yellow | 428 |
| β-carotene | 7235-40-7 | orange | 466 |
| Rifampin | 3292-46-1 | red | 475 |
| Yellow No. 6 | 2783-94-0 | yellow | 480 |
| Tetracycline | 60-54-8 | yellow | N/A |
| Red No. 40 | 25956-16-6 | red | 502 |
| Red No. 3 | 16423-68-0 | red | 524 |
| Blue No. 2 | 860-22-0 | blue | 610 |
| Evan's blue | 314-13-6 | blue | 610 |
| Green No. 3 | 2353-45-9 | green | 628 |
| Blue No. 1 | 2650-18-2 | blue | 630 |
| Methylene blue | 7220-79-3 | Blue | 668/609 |
| Indocyanine green | 3599-32-4 | Green | 800 (mostly IR) | certain embodiments, the chromophore, e.g., alizarin, is selected from any dye that binds boronic acid moieties, preferably having absorbance/fluorescence properties that differ in the bound vs. the free state. When a suitable chelatable analyte is present, the boronic acid releases the chromophore and binds the analyte. Additional FDA approved dyes and colored drugs are described in the Code of Federal Regulations (CFR) for Food and Drugs (see Title 21 of CFR chapter 1, parts 1-99). A wide variety of chromophores and fluorescence sources may be used, e.g., paired so that the absorbance wavelength of the unbound chromophore substantially matches the wavelength of the fluorescent component's photon emissions, e.g., so as to absorb the emissions in an unbound state. The table below lists a number of suitable chromophores, their Chemical Abstract Service (CAS) Registration Numbers, colors and absorption maxima. In certain embodiments, the chromophore is derivatized in such a manner that it can bind with the chelating moiety of the sensor.

In certain embodiments, the chromophore is covalently conjugated to the polymer matrix and/or the surface coating and comprises a reactive site that binds reversibly with the chelatable analyte selective moieties. In an exemplary embodiment, the chromophore is alizarin, and the alizarin is covalently bound to the polymer matrix and/or the surface coating through one or more linkers or bonds. In certain embodiments, the linker is an ester amide, ether, sulfonate, thioether, carbonate or thioester originating from an aromatic carbon of the alizarin. In certain embodiments, the chromophore is covalently conjugated through one or more bonds to the polymer matrix and/or the surface coating. In certain embodiments, the bonds or linkages between the chromophore and the polymer matrix and/or the surface coating does not interfere with the ability of the chromophore to bind to the chelatable analyte. For example, in the case of alizarin, the linkages or bonds to the polymer matrix and/or the surface coating originates from a ring of the polycyclic ring system that does not bear the hydroxy groups. In certain such embodiments, the hydroxyl groups of the alizarin are unimpeded from interacting with the chelatable analyte.

In certain embodiments, the sensor particle for detecting the presence of glucose comprises: a quantum dot, a surface coating, a polymer matrix comprising a polymer appended with moieties that selectively bind glucose, a chromophore associated with the polymer matrix that binds the moieties in the absence of glucose, and a polymer coating, such as a biocompatible coating.

In certain embodiments, additives to the polymer matrix and/or the coating make the extraction of the analyte (e.g., glucose) into the polymeric matrix more efficient. In certain embodiments, the addition of amine-based additives to the matrix lowers the effective dynamic range of the sensor particles. In certain embodiments, the addition of amines to the polymer matrix increases the affinity of the polymer matrix for the analyte, e.g., glucose.

In an exemplary embodiment, sensors are ionic sensors. Emissions from the sensor indicate the ion concentrations and fluxes from the cell. In certain aspects, the sensors comprise a polymer, a fluorescent semiconductor nanocrystal (also known as a quantum Dot™ particle) or a fluorescent dye that fluoresces at a first wavelength, and a chromoionophore that absorbs photons of the first wavelength in one state and does not absorb photons of the first wavelength in a second state. In monitoring ionic analytes, the chromoionophore changes state in response to proton concentration (i.e., the protonated chromoionophore is one state while the deprotonated chromoionophore is a second state). To monitor a specific analyte, an ionophore that selectively associates with specific ions or groups of ions is included in the sensor. Once the ionophore associates with a cationic analyte (e.g., $Na^+$ associates with a $Na^+$-selective ionophore), for example, protons are displaced from the sensor to equilibrate charge, altering the state of the chromoionophore. The fluorescence emitted from the sensor indicates the state of the chromoionophore which correlates to the presence and/or concentration of the ionic analyte. Sensors that use fluorescent dyes instead of quantum dots are disclosed in PCT Publication No. WO2008/063151A2, the disclosure of which is incorporated herein by reference.

For ion-detecting sensors, the ionophore is a compound, typically an electrically neutral compound, that associates (e.g., forms a complex, chelate, or other non-covalent association) with a target ion, and is selective for the target ion relative to other ions. The ionophore is selected to be lipid-soluble and does not emit light in the visible spectrum in either of its complexed and non-complexed states. In certain aspects, the ionophore of the mixture included herein is chosen to selectively bind an ionic analyte, for example, $K^+$, $Na^+$, $Ca^{2+}$, $H^+$, $Ba^{2+}$, $Li^+$, $Cl^+$, $NH_4^+$, or $NO_3^-$. Potassium ion ionophores include, for example, valinomycin, crown ethers, e.g., dimethyldibenzo-30-crown-10, dicyclohexyl-18-crown, dimethyldicyclohexyl-18-crown-6, tetraphenyl borate, tetrakis(chlorophenyl)borate. Sodium ion ionophores include, for example, methyl monensin, N,N',N"-triheptyl-N,N',N"-trimethyl-4,4',4"-propylidintris-(3-oxabutyramide), N,N,N',N'-tetracyclohexyl-1,2-phenylenedioxydiacetamide, 4-octadecanoyloxymethyl-N,N,N',N'-tetracyclohexyl-1,2-phenylenedioxydiacetamide, bis[(12-crown-4)methyl]dodecylmethylmalonate. Exemplary calcium ion ionophores include, for example, bis(didecylphosphate), bis(4-octylphenylphosphate), bis(4-(1,1,3,3-tetramethylbutyl)phenylphosphate tetracosamethylcyclododecasiloxane, N,N'-di(11-ethoxycarbonyl)undecyl)-N,N',4,5-tetramethyl-3,6-dioxaoctane diamide. Barium ion ionophores include, for example, calcium di(2-ethylhexyl)phosphate+decan-1-ol, barium complex of nonylphenoxypoly(ethyleneoxy)ethanol in ortho-nitrodiphenyl ether. Chloride ion ionophores include, for example, {μ-[4,5-dimethyl-3,6-bis(octyloxy)-1,2-phenylene]}bis(trifluoroacetato-O)dimercuri (ETH 9009), {μ-[4,5-dimethyl-3,6-bis(dodecyloxy)-1,2-phenylene]}bis(mercury chloride) (ETH 9033), 5,10,15,20-tetraphenyl-21H,23H-porphin manganese (III) chloride (MnTPPCl), tributyltin chloride (TBTCl) and trioctyltin chloride (TOTCl). Bicarbonate ion ionophores of the invention include, for example, quaternary ammonium ion exchanger p-octodecyloxy-meta-chlorophenyl-hydrazone-mesoxalonitrile. Ammonium ion ionophores include, for example, nonactin and monactin. Nitrate ion ionophores include, for example, tridodecylhexadecylammonium nitrate+n-octyl-ortho-nitrophenyl, 1:10 phenanthroline nickel (II) nitrate+para-nitrocymene. Lithium ion ionophores include, for example, N,N'-diheptyl-N,N',5,5-tetramethyl-3,7-dioxononanediamide), 12-crown-4,6,6-dibenzyl-14-crown-4.

A chromoionophore is an ionophore that changes its optical properties in the visible spectrum depending on the state of complexation. Chromoionophores for use in sensors are typically proton-sensitive dyes that change absorbance (and fluorescence in many cases) depending on the degree of protonation, although chromoionophores that change absorbance in response to other ions can also be used. The chromoionophores are preferably highly lipophilic to inhibit leaching from the sensor matrix. Suitable chromoionophores include Chromoionophore I (i.e., 9-(Diethylamino)-5-(octadecanoylimino)-5H-benzo[a]phenoxazine), Chromoionophore II (i.e., 9-Dimethylamino-5-[4-(16-butyl-2,14-dioxo-3,15-dioxaeicosyl)phenylimino]benzo[a]phenoxazine) and Chromoionophore III (i.e., 9-(Diethylamino)-5-[(2-octyldecyl)imino]benzo[a]phenoxazine). Chromoionophore II exhibits light absorbance peaks at 520 nm and 660 nm and a fluorescent emission peak at 660 nm. Chromoionophore III has light absorbance peaks at 500 nm and 650 nm and fluorescent emission peaks at 570 nm and 670 nm.

An ion-detecting sensor may comprise an additive, e.g., to embed charge sites within the polymer phase and/or to help enforce charge neutrality within the sensor. For sensors targeting cations, the additive can be any inert and preferably lipophilic component that has a negative charge associated with it. For sensors targeting anions, the additive is positively charged and preferably lipophilic. The additive allows the polymer phase to carry a corresponding amount of oppositely charged particles while maintaining overall charge neutrality of the sensor. The concentration ratio of additive to chromoionophore is preferably 1:1, thereby allowing the chromoionphore to become completely protonated or deprotonated. One suitable additive for sensors targeting negative ions is potassium tetrakis[3,5-bis(trifluoromethyl)phenyl]borate (KTFPB). The lipophilic, anionic component TFPB molecules are retained by the polymer phase, and the potassium ions are either complexed by the ionophore or expelled into the sample solution through diffusion. In one particular implementation, the sensor film is composed of a suspension produced from about 60 mg of DOS, 30 mg of PVC, and up to about 5 mg of additive, ionophore, and chromoionophore.

Figure 14:
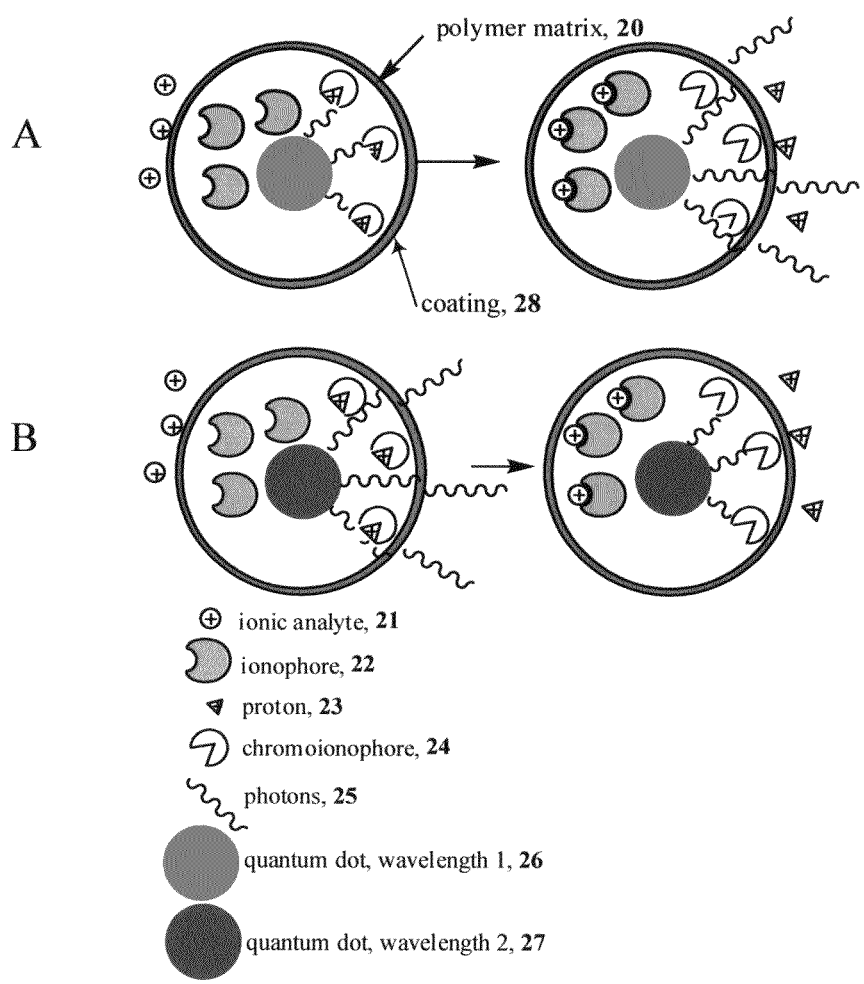
FIG. 14. A representation of two exemplary modes of operation of the quantum dot incorporated coated sensor for the detection of cationic analytes. In mode A, the sensor fluoresces in the presence of the ionic analyte. In mode B, the sensor fluoresces in the absence of ionic analyte.

In a sample solution, the sensor continuously extracts or expels, for example, analyte cations depending on ion activity in the sample solution. The ion activity of a sample solution can be monitored by observing the fluorescence of a sensor of the invention in the sample solution. As depicted in FIG. 14, the sensor with a coating 28 may fluoresce in the presence of a cationic analyte 21, and not in the absence of said analyte, Mode A. In such embodiments, the chromoionophore 24, of the sensor absorbs photons 25, of a quantum dot 26, when the cationic analyte 21 is not bound to the ionophore 22. In such embodiments, the wavelength of photons 25 emitted from the quantum dot 26 when excited with a light source such as UV or visible light fall within the absorbance range, e.g., maximum absorbance range, of the chromoionophore 24 bound to a proton 23, such that the fluorescence of the quantum dot is attenuated or completely undetectable from outside of the polymer matrix 20 (Mode A, sensor on the left). As the target ion 21 increases in concentration in solution, the ions 21 are drawn through the coating 28 into the polymer matrix 20 to bind with the ion-selective ionophore 22. To maintain charge neutrality within the polymer matrix 20, protons 23 dissociate from the chromoionophore 24 in the sensor and diffuse out of the polymer matrix 20 through the coating 28 into the sample solution, altering the absorbance properties of the chromoionophore 24. The deprotonated chromoionophore 24 has a shifted absorbance region such that the photons 25 emitted by the quantum dot 26 are no longer absorbed by the chromoionophore 24 (Mode A, sensor on the right). The sensor then emits a detectable signal indicating the presence of the analyte.

In an alternate embodiment for detecting cationic analytes, FIG. 14, Mode B, the quantum dot 27 of the sensor emits photons 25 that are not absorbed by the chromoionophore 24 in the absence of the cationic analyte 21. In certain such embodiments, the chromoionophore 24 absorbs photons 25 of the quantum dot 27 when the cationic analyte 21 is bound to the ionophore 22. In such embodiments, the wavelength of emitted photons 25 from the quantum dot 27 when excited with a light source such as UV or visible light, do not fall within the absorbance range, e.g., the maximum absorbance range, of the chromoionophore 24 when bound to a proton 23, such that the fluorescence of the quantum dot 27 is emitted from the polymer matrix 20 (Mode B, sensor on the left). As the target ion 21 increases in concentration in solution, the ions 21 are drawn through the coating 28 into the polymer matrix 20 to bind with the ion-selective ionophore 22. To maintain charge neutrality within the polymer matrix 20 of the sensor, protons 23 dissociate from the chromoionophore 24 of the sensor and diffuse out of the polymer matrix 20 through the coating 28 into the sample solution, altering the absorbance properties of the chromoionophore 24. The deprotonated chromoionophore 24 has a shifted absorbance region such that the photons 25 emitted by the quantum dot 27 are absorbed by the chromoionophore 24 (Mode B, sensor on the right). The sensor signal is attenuated or extinguished indicating the presence of the analyte.

Figure 15:
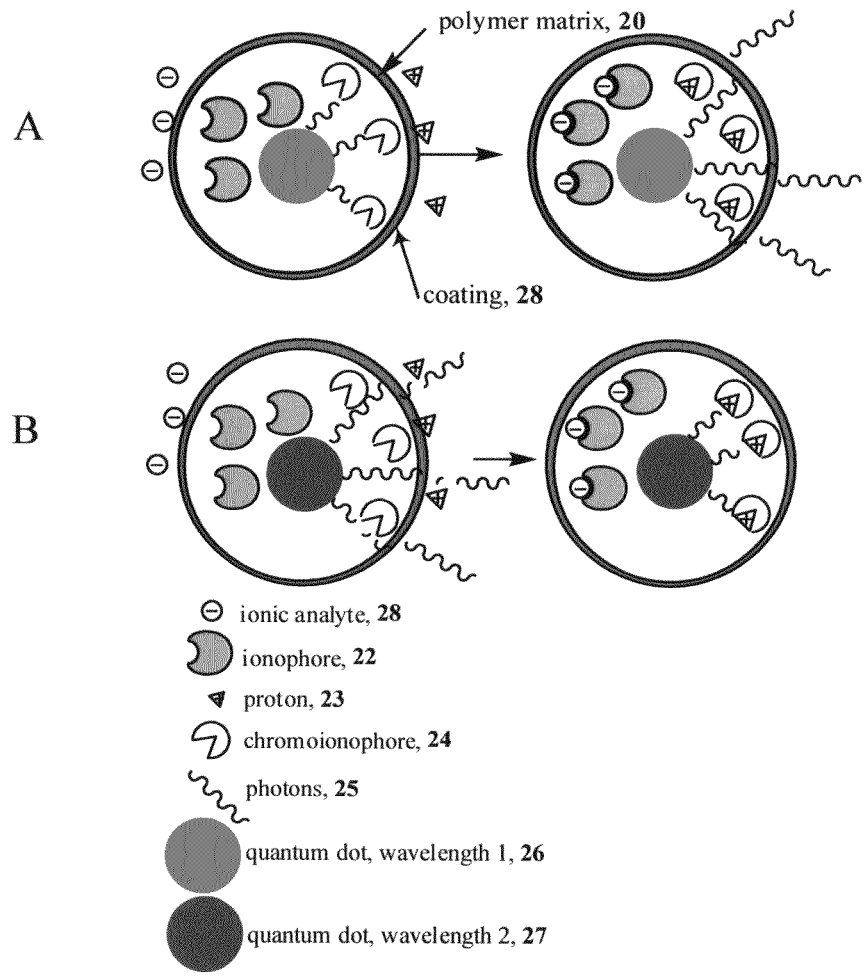
FIG. 15. A representation of two exemplary modes of operation of the quantum dot incorporated coated sensor for the detection of anionic analytes. In mode A, the sensor fluoresces in the presence of the ionic analyte. In mode B, the sensor fluoresces in the absence of ionic analyte.
Figure 16:
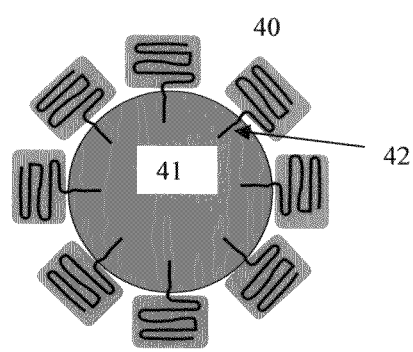
FIG. 16. A representation of a sensor coated with a surface modifier such as PEG.
Figure 17:
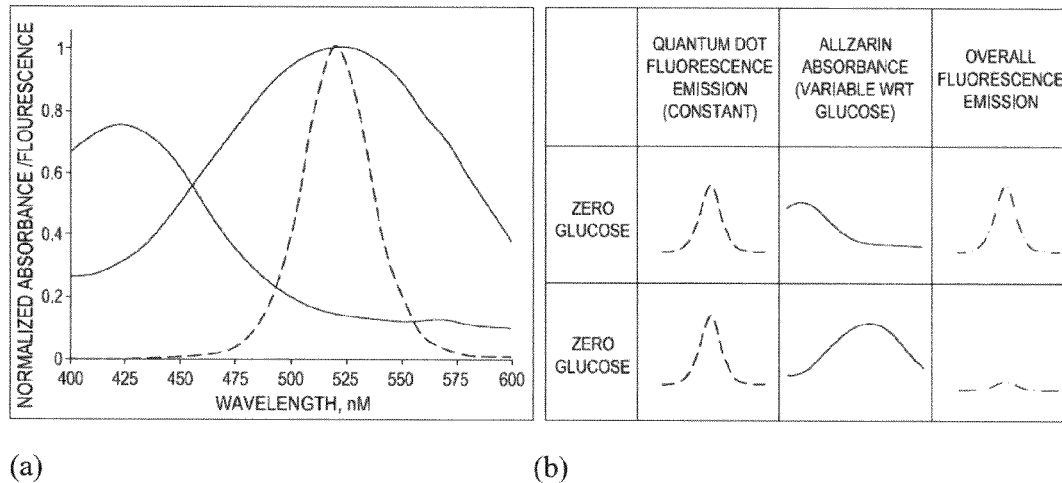
FIG. 17. Spectral signature of the components of a glucose sensitive sensor; (a) overlap of normalized alizarin absorbance and quantum dot emission, (b) individual contribution of the two components of the inner filter effect at high and low glucose concentration and the resulting overall fluorescence signal.

In an embodiment for detecting anionic analytes, depicted in FIG. 15, Mode A, the ionophore 22 of the sensor selectively binds an anionic analyte 28 or a group of anionic analytes. In certain such embodiments, the sensor comprises a chromoionophore 24 which absorbs photons 25 emitted from the quantum dot 26 upon excitation, e.g., by light such as UV or visible, when the ionic analyte 28 is not bound to the ionophore 22 of the sensor. In such a state, the wavelengths of the photons 25 emitted by the quantum dot 26 are within the absorbance range, e.g., the maximum absorbance range, of the chromoionophore 24 in a deprotonated state and the fluorescence detected outside of the polymer matrix 20 is attenuated or undetectable from outside the sensor (FIG. 14, Mode A, sensor on the left). As the target ion 28 increases in concentration in the sample solution, the anionic analyte 28 is drawn into the polymer matrix 20 through the coating 28, binding with the ion-selective ionophore 22. To maintain charge neutrality within the polymer matrix 20, protons 23 diffuse from the sample solution into the polymer matrix 20 through the coating 28, protonating the chromoionophores 24 such that the absorbance properties are altered. The protonated chromoionophore 24 has a shifted absorbance region such that the photons 25 of the quantum dot 26 are not absorbed by the chromoionophore 24 (FIG. 14, Mode A, sensor on the right). The sensor emits a detectable fluorescence signal indicating the presence of the analyte 28.

In an alternate embodiment for detecting anionic analytes, depicted in FIG. 15, Mode B, the ionophore of the sensor selectively binds an anionic analyte 28 or a group of anionic analytes. In certain such embodiments, the sensor comprises a chromoionophore 24 which does not absorb photons 25 emitted from the quantum dot 26, upon excitation, e.g., by light such as UV or visible, when the ionic analyte 28 is not bound to the ionophore 22 of the sensor. In such a state, the wavelengths of the photons 25 emitted by the quantum dot 26 are outside of the absorbance range, e.g., the maximum absorbance range, of the chromoionophore 24 in a deprotonated state and the fluorescence detected outside of the polymer matrix 20 is attenuated or absent (FIG. 14, Mode B, sensor on the left). As the target ion 28 increases in concentration in the sample solution, the anionic analyte 28 is drawn into the polymer matrix 20 through the coating 28, binding with the ion-selective ionophore 22. To maintain charge neutrality in the polymer matrix 20, protons 23 diffuse from the sample solution into the polymer matrix 20 through the coating 28, protonating the chromoionophores 24 such that the absorbance properties are altered. The protonated chromoionophore 24 has a shifted absorbance region such that the photons 25 of the quantum dot 26 are not absorbed by the chromoionophore 24 (FIG. 14, Mode B, sensor on the right). The sensor signal is attenuated or extinguished indicating the presence of the analyte 28.

The following is a non-limiting, illustrative list of target ion (21 or 28)/ionophore 22 pairings suitable for use in the sensors: potassium/Potassium Ionophore III (i.e., BME-44, 2-Dodecyl-2-methyl-1,3-propanediyl bis[N-[5'-nitro(benzo-15-crown-5)-4'-yl]carbamate]), sodium/Sodium Ionophore IV (i.e., 2,3:11,12-Didecalino-16-crown-5 2,6,13,16,19 Pentaoxapentacyclo[18.4.4.4$^{7.12}$.0$^{1.20}$.0$^{7.12}$]dotriacontane), sodium/Sodium Ionophore V (i.e., 4-Octadecanoyloxymethyl-N,N,N',N'-tetracyclohexyl-1,2-phenylenedioxydiacetamide), sodium/Sodium Ionophore VI (i.e., Bis[(12-crown-4)methyl]dodecylmethylmalonate Dodecylmethylmalonic acid bis[(12-crown-4)methyl ester]), sodium/Sodium Ionophore X (4-tert-Butylcalix[4]arene-tetraacetic acid tetraethylester), calcium/Calcium Ionophore III (i.e., Calimycin), and calcium/Calcium ionophore IV (i.e., N,N-Dicyclohexyl-N', N'-dioctadecyl-diglycolic diamide). For target anions, illustrative target ion/ionophore pairings include chloride/Chloride Ionophore III (i.e., 3,6-Didodecyloxy-4,5-dimethyl-o-phenylene-bis(mercury chloride) and nitrite/Nitrite Ionophore I (i.e., Cyanoaqua-cobyrinic acid heptakis(2-phenylethyl ester)).

In various embodiments, ion-detecting sensors may be constructed to directly detect the presence of particular ions. As illustrated in the tables below, it is known in the art that certain diseases affect particular ion channels in a cell. Accordingly, assays for those ions utilizing the present invention may furnish a diagnostic tool to determine the presence of particular diseases. Accordingly, the scope of the present invention should be understood to also include the application of the heretofore-described subject matter to measure the ions set forth in the following tables, as well as their application to diagnose the presence of the associated diseases also appearing in the following tables.

| Channel | Gene | Channel-forming unit/ligand | OMIM | Disease |
|---|---|---|---|---|
| Cation channels: | | | | |
| CHRNA1/ACHRA | CHRNA1 | α, ACh | 100690 | Myasthenia congenita |
| CHRNA4 | CHRNA4 | α, ACh | 118504 | Autosomal dominant nocturnal frontal lobe epilepsy |
| CHRNB2 | CHRNB2 | β, ACh | 118507 | Autosomal dominant nocturnal frontal lobe epilepsy |
| Polycystin-2 | PKD2 | α | 173910 | Autosomal dominant polycystic kidney disease (ADPKD) |
| CNGA3 | CNGA3 | α, cGMP | 60053 | Achromatopsia 2 (color blindness) |
| CNGB1 | CNGB1 | β, cGMP | 600724 | Autosomal recessive retinitis pigmentosa |
| CNGB3 | CNGB3 | β, cGMP | 605080 | Achromatopsia 3 |

-continued

| Channel | Gene | Channel-forming unit/ligand | OMIM | Disease |
|---|---|---|---|---|
| Sodium channels: | | | | |
| Na. 1.1 | SCN1A | α | 182389 | Generalized epilepsy with febrile seizures (GEFS+) |
| Na. 1.2 | SCN2A | α | 182390 | Generalized epilepsy with febrile and afebrile seizures) |
| Na. 1.4 | SCN4A | α | 603967 | Paramyotonia congenital, potassium aggressive myotonia, hyperkalemic periodic paralysis |
| Na. 1.5 | SCN5a | α | 600163 | Long-QT syndrome, progressive familial heart block type 1, Brugada syndrome (idiopathic ventricular arrhythmia) |
| SCNIB | SCNIB | β | 600235 | Generalized epilepsy with febrile seizures (GEFS+) |
| ENACα | SCNNIA | α | 600228 | Pseudohypoaldosteronism type 1 (PHA1) |
| ENaCβ | SCNN1B | β | 600760 | PHA1, Liddle syndrome (dominant hypertension |
| ENaCγ | SCNN1G | γ | 600761 | PHA1, Liddle syndrome |
| Potassium channels: | | | | |
| K, 1.1. | KCNA1 | α | 176260 | Episodic ataxia with myokymia |
| KCNQI/K, LQT1 | KCNQ1 | α | 192500 | Autosomal dominant long-QT syndrome (Romano-Ward) Autosomal recessive long-QT syndrome with deafness (Jervell-Lange-Nielsen) |
| KCNQ2 | KCNQ2 | α | 602235 | BFNC (epilepsy), also with myokymia |
| KCNQ3 | KCNQ3 | α | 602232 | BFNC (epilepsy) |
| KCNQ4 | KCNQ4 | α | 603537 | DFNA2 (dominant hearing loss) |
| HERG/KCNH2 | KCNH2 | α | 152427 | Long-QT syndrome |
| Kir1. 1/ROMK | KCNJ1 | α | 600359 | Bartter syndrome (renal salt loss, hypokalemic alkalosis) |
| Kir2. 1/IRK/KCNJ2 | KCNJ2 | α | 600681 | Long-QT syndrome with dysmorphic features (Andersen syndrome) |
| Kir6.2/KATATP$_{ATP}$ | KCNJ11 | α | 600937 | Persistent hyperinsulinemic hypoglycemia of infancy (PHHI) |
| SURI | SURI | β | 600509 | PHHI |
| KCNE1/Mink/ISK | KCNE1 | β | 176261 | Autosomal dominant long-QT syndrome (Romano-Ward) Autosomal recessive long-QT syndrome with deafness (Jervell-Lange-Nielson) |
| KCNE2/MiRP1 | KCNE2 | β | 603796 | Long-QT syndrome |
| KCNE3/MiRP2 | KCNE3 | β | 604433 | Periodic paralysis |
| Calcium channels: | | | | |
| Ca. 1.1 | CACNA1S | α | 114208 | Hypokalemic periodic paralysis, malignant hyperthermia |
| Ca, 1.4 | CACNA1F | α | 300110 | X-linked congenital stationary night blindness |
| Ca, 2.1 | CACNA1A | α | 601011 | Familial hemiplegic migraine, episodic staxia, spinocerebella ataxia type 6 |
| RyRI | RYRI | α | 180901 | Malignant hyperthermia, central core disease |
| RyR2 | RYR2 | α | 180902 | Catecholaminergic polymorphic ventricular tachycardia, arrhythmogenic right ventricular dysplasia type 2 |
| Chloride channels: | | | | |
| CFTR | ABCC7 | α | 602421 | Cystic fibrosis, congenital bilateral asplasia of vas deference |
| CIC-1 | CLCN1 | α | 118425 | Autosomal recessive (Becker) or dominant (Thomsen myotonia |
| CIC-5 | CLCN5 | α | 300008 | Dent's disease (X-linked proteinuria and kidney stones) |

| Channel | Gene | Channel-forming unit/ligand | OMIM | Disease |
|---|---|---|---|---|
| ClC-7 | CLCN7 | α | 602727 | Osteopetrosis (recessive or dominant) |
| ClC-Kb | CLCNKB | α | 602023 | Bartter syndrome type III |
| Barttin | BSND | β | 606412 | Bartter syndrome type IV (associated with sensorineural deafness) |
| GLRA1 | GLRA1 | α, glycine | 138491 | Hyperekplexin (startle disease) |
| GABAα1 | GABRA1 | α GABA | 137160 | Juvenile myoclonus epilepsy |
| GABAγ2 | GABRG2 | γ, GABA | 137164 | Epilepsy |
| Gap junction channels: | | | | |
| Cx26 | GJB2 | | 121011 | DFNB3 (autosomal dominant hearing loss) DFNB1 (autosomal recessive hearing loss) |
| Cx30 | GJB4 | | 605425 | DFNA3 |
| Cx31 | GJB3 | | 603324 | DFNA2 |
| Cx32 | GJB1 | | 304040 | CMTX (X-linked Charcot-Mari-Tooth neuropathy) |
| AChR α7 | | | | Inflammation |
| ClC7 | | | | Osteoporosis |
| Ether-a-go-go (eag, erg, elk) | | | | Cancer |
| Gardos channel | | | | Sickle cell anemia |
| P2X7 | | | | Immune disorders |
| TRPC6 | | | | Asthma, COPD |
| TRPM1 | | | | Melanoma |
| TRPM2 | | | | Asthma |
| TRPM4 | | | | Immune disorders |
| TRPM7 | | | | Stroke |
| TRPM8 | | | | Prostate cancer |
| TRPV1 | | | | Urinary incontinence, pain |

The third column classifies channel proteins into α, β, and γ subunits, where α subunits are always directly involved in pore formation, Several β subunits are only accessory (i.e., do not form pores), as is the case, for example, with SCN1B and barttin. Others (e.g. of ENaC and GABA receptors) participate in pore formation. For ligand-gated channels, the ligand is given. Note that GABA and glycine act from the extracellular side, whereas cGMP is an intracellular messenger.

| Gene | Accession ID | Gene Locus | Sodium Channel Type/Disease | Tissue Expression |
|---|---|---|---|---|
| SCN1A | GDB: 118870 S71446 | 2q24 | SCN1, vg type 1, α-subunit (280 KDa) | Brain |
| SCN1B | GDB: 127281 U12188-12104 L16242, L10338 | 19q13.1 | Hs.89634, vg type 1 $\beta_1$ subunit (38 KDa) | Brain, heart, skeletal muscle |
| SCN2A1 | GDB: 120367 | 2q23 | SCN2A, HBSC1, vg type II, $\alpha_1$-subunit (280 KDa) | Brain, peripheral nerve |
| SCN2A2 | CDB: 133727 | 2q23-24.1 | HBSCH, vg type II, $\alpha_2$-subunit vg type II, $\beta_2$-subunit (33 KDa) | Brain |
| SCN2B | GDB: 118871 AF019498 | | | |
| SCN3A | GDB: 132151 S69887 | 2q24-31 | vg type III, α-subunit (280 kDa) | Brain |
| SCN4A | GDB: 125181 L04216-L04236 | 17q23.1-25.3 | SkM1, vg type IV α-subunit (260 kDa), hyperkalemic periodic paralysis, paramyotonia congentia, potasssturn-aggravated myotonia | Skeletal muscle |
| SCN4B | GDB: 125182 | 3q21 | vg type IV, β-subunit, | Heart, fetal skeletal muscle |
| SCN5A | GDB: 132152 | | SkM2, hH1, vg type V, α-subunit, long Q-T syndrome 3 | |

| Gene | Accession ID | Gene Locus | | Tissue Expression |
|---|---|---|---|---|
| SCN6A | GDB: 132153 | 2q21-23 | Hs99945, vg type VI, α-subunit | Heart, uterus, fetal and denervated skeletal muscle |
| SCN7A | GDB: 228137 | 12q13 | vg type VII, α-subunit | Brain, spinal cord |
| SCN8A | GDB: 631695 | | vg type VIII, α-subunit, motor end-plate disease + ataxia in mice | |
| SCN9A | GDB: 3750013 | | vg type IX, α-subunit neuroendocrine type | Thyroid and adrenal gland |
| SCN10A | GDB: 750014 | 1pter-p36.3 | hPN3, vg type X | Sensory neurons, dorsal root ganglia |
| SCNN1A | GDB: 366596 Z92978 | 12pt3 | SCNN1, nvg type 1 α-subunit of ENaC | Kidney, lung, colon |
| SCNN1B | GDB: 434471 | 16p12.2-p12.1 | nvg 1 β-subunit, Liddle's syndrome, pseudohypoaldosterontsm I | Kidney, lung, colon |
| SCNN1D | GDB: 6053678 | 1p36.3-p36.2 | DnaCh, nvg 1 δ-subunit | Kidney, lung, colon |
| SCNN1G | GDB: 568769 X87160 U53835-53853 | 16p122-p12.1 | nvg 1 γ-subunit, Liddle's syndrome, pseudohypoaldosterontsm I Calcium Channel Type/Disease | Kidney, lung, colon |
| CACNA1A CACNL1A4 | GDB: 126432 Z80114-Z80155, X99697, U79666 | 19p13 19p13.1 | P/Q type $α_{1A}$-subunit, eqisodic ataxia 2, familial hemiplegic migraine, spinocerebellar ataxia 6; tottering, leaner, and rolling mice | Brain (cortex, bulbus, olfacorius, hippocampus, cerebellum, brain stem), motoneurons, kidney |
| CACNA1B CACNL1A5 | GDB: 580689 M94172, M94173 | 9q34 | CACNN, N-type $α_{1A}$-subunit | Central, peripheral nervous system |
| CACNA1C CACNL1A1 | GDB: 126094 L29636, L29634, L29629 | 12p13 12p13.3 | CCHL1A1, L-type $α_{1A}$-subunit | Heart, fibroblasts, lung, smooth muscle (2 splice variants) |
| CACNA1D CACNL1A2 | GDB: 128872 | 3p14.3 3p21.3.2? | CCHL1A2, L-type $α_{1D}$-subunit | Brain, pancreas, neuroendocrine |
| CACNA1E CACNL1A6 | GDB: 434408 | 1q25-31 | R-type $α_{1C}$-subunit | Brain, skeletal muscle (end plate) |
| CACNA1F | GDB: 6053864 | Xp11.23-11.22 | $α_{1F}$-Subunit | Retina |
| CACN1AG | AF27964 | 17q22 | T-type $α_{1G}$-subunit | Brain |
| CACNA1S CACNL1A8 | GDB: 126431 Z22672, L33798 U30666-U30707 | 1q31-32 | L-type $α_{1B}$-subunit (5% 212, 95% 190 kDa), malignant hyperthermia 5, hypokalemic periodic paralysis | Skeletal muscle (brain, kidney) |
| CACNA2 CACNL2A | GDB: 132010 Z28613, Z28609 Z28605, Z28602 Z28699, M76559 | 7q21-22 | CACNA2, CACNA2D1, $α_g$ 8-subunit (175 kDa), MHS3 | $α_{2A}$; skeletal muscle, heart, brain, ileum; $α_{2B}$; brain; $α_{2CVD}$ aorta |
| CACNB1 CACNLB1 | GDB: 132012 GDB: 1073281 U86952-U86961 M76560, L06111 GDB: 193328 | 17q21-22 | $β_1$-Subunit (524 aa, 54 kDa) | $β_1$A/M; skeletal muscle $β_1$B/C; brain, heart, spleen |
| CACNB2 CACNLB2 | GDB: 132014 Q08289 | 10p12 | MYSB, $β_2$-subunit | $β_2$-A/B/E; brain, heart, lung, aorta |

-continued

| Gene | Accession ID | Gene Locus | | Tissue Expression |
|---|---|---|---|---|
| CACNB3 CACNLB3 | GDB: 341023 L27584 | 12q13 | β₂-subunit (482 aa) | Brain, heart, lung, spleen, skeletal and smooth muscle, aorta, trachea, ovary, colon |
| CACNB4 | GDB: 6028693 | 2q22-23 | β₂-subunit, lethargic mice | Brain, kidney |
| CACNG CACNLG | GDB: 132015 L07738 | 17q24 | γ-Subunit (222 aa, 30 kDa) | Skeletal muscle, lung |
| CACNG2 | | | γ2-Subunit, stargazin, absence epilepsy stargazer, waggler mice | Brain |
| RYR1 | GDB: 120359 | 19q13.1 | Ryanodine receptor 1, Ca release channel, 3 splice variants, malignant hyperthermia 1, central core disease | Skeletal muscle, testis, brain, submaxillary and adrenal glands, spleen |
| RYR2 | GDB: 125278 | 1pter-qter 1q42.1-43 | RYR2, calcium release channel | Heart, smooth muscle |
| RYR3 | GDB: 138451 | 15q14 15q14-15 | RYR3, calcium release channel | Brain, neonatal skeletal muscle, adult diaphragm |
| | | | Potassium Channel Type/Disease | |
| KCNA1 | GDB: 127903 LO2750 | 12p13 | RBK1, HUK1, MBK1, AEMK, Kv1.1, Shaker homolog 1, Shaker, episodic ataxia 1 (with myokymia) | Brain, nerve, heart, skeletal muscle, retina, pancreatic islet |
| KCNA1B | | 3q26.1 | Kvβ1.1, Kvβ1.3 (splice product), β-subunit | |
| KCNA2 | GDB: 128062 X17622 | 12pter-qter | HK4, Kv1.2, Shaker homolog 2 | Brain, nerve, heart, pancreatic islet |
| KCNA2B | | 1p36.3 | Kvβ1.2, β-subunit | |
| KCNA8 | GDB: 128079 L23499 | 1p13.3 | Hs.1750, MK3, HLK3, HPCN3, Kv1.3, Shaker homolog 3 | Skeletal muscle, lymphocytes (brain, lung, thymus, spleen) |
| KCNA4 | GDB: 126730 M60450 M55514 | 11p14 | Hs.89647, Hs.1854, HK1, HPCN2, Kv1.4, Shaker homolog 4 | Brain, nerve, heart, fetal skeletal muscle, pancreatic islet |
| KCNA4L | GDB: 386059 | 11q14 | Shaker homolog type 4-like | |
| KCNA5 | GDB: 127904 M83254 M60451 | 12p13.3-13.2 12p13 12p13.33-12.31 | Hs.89509, HK2, HPCNI, Kv1.5 Shaker homolog 5 | Brain, heart, kidney, lung, skeletal muscle, pancreatic islet |
| KCNA6 | GDB: 128080 X17622 | 12p13 | HBK2, Kv1.6, Shaker homolog 6 | Brain, pancreatic islet |
| KCNA7 | GDB: 127905 | 19q13.3 | HAK6, Kv1.7 Shaker homolog 7 | |
| KCNA8 | | | see KCNQ1 | |
| KCNA9 | | | see KCNQ1 | |
| KCNA10 | GDB: 5885822 | | Shaker homolog type 10, cGMP activated | |
| KCNB1 | GDB: 128081 | 20q13.2 | Kv2.1, Shab homolog 1 | Brain, heart, kidney, retina, skeletal muscle |
| KCNB2 | | | Kv2.2, Shab homolog 2 | Brain, heart, retina |
| KCNC1 | GDB: 128082 S56770 M96747 | 11p15.1 | Kv3.1, Shaw homolog 1 | Brain, skeletal muscle, spleen, lymphocytes |
| KCNC2 | GDB: 127906 | 19q13.3-13.4 | Kv3.2, Shaw homolog 2 | Brain |
| KCNC3 | GDB: 127907 | 19q13.3 | Kv3.3, Shaw homolog 3 | Brain, liver |
| KCNC4 | GDB: 127908 | 1p21 | Kv3.4, HKSHIIIC, Shaw homolog 4 | Brain, skeletal muscle |
| KCND1 | GDB: 128083 | | Kv4.1, Shal homolog 1 | Brain |
| KCND2 | GDB: 134771 | | RK5, Kv4.2, Shal homolog 2 | Brain, heart, aorta |
| KCND3 | GDB: 134772 | | Kv4.3, KSHIVB, Shal homolog 3 | |

-continued

| Gene | Accession ID | Gene Locus | | Tissue Expression |
|---|---|---|---|---|
| KCNE1 | GDB: 127909 | 21q22.1-22.2 | MinK, ISK, vg Isk homolog 1 (129 aa), long Q-T syndrome 5 | Kidney, submandibular gland, uterus, heart, cochlea, retina |
| KCNMA1 | GDB: 386031 U09383-4 U02632 | 10pter-qter 7q32.1 | SLO, Hs.62679, α-subunit member 1, α-subunit of maxiK or BK channel | Fetal skeletal muscle |
| KCNMB1 | GDB: 6099615 U42600 | 5q34 | hSLO-β, β-subunit member 1 (191 aa), β-subunit of max IK or BK channel | Smooth, fetal skeletal muscle, brain (hippocampus, corpus callosum) |
| KCNN1 | U69883 | | SK(Ca)1, small-conductance Ca-activated K channel, apamin-insensitive | Brain, heart |
| KCNN2 | | | SK(Ca)2, apamin sensitive | Brain, adrenal gland |
| KCNN3 | Y08263 AA285078 | 1q? | SK(Ca)3, small-conductance Ca-activated K channel, intermediate apamin sensitivity | Brain, heart, (human embryonic) skeletal muscle, liver |
| KCNN4 | AF022150 AF022797 AF033021 AF000972 | 19q13.2 | IK1, intermediate-conductance Ca-activated K channel, KCa4, SK4, Gantos channel | T lymphocytes, colon, smooth muscles, prostata, red blood cells, neurons |
| KCNQ1 | GDB: 741244 U40990 | 11p15.5 | KCNA9, (KV)LQT1, KQT-like subfamily member 1, long Q-T syndrome 1 | Heart, cochlea, kidney, lung, placenta, colon |
| KCNQ2 | GDB: 9787229, Y15065, AF033348 | 20q13.3 | KQT-like subfamily member 2 (872 aa) | Brain |
| KCNQ3 | GDB: 9787230 AF033347 | 8q24.22-24.3 | KQT-like subfamily member 3 (825 aa) | Brain |
| HERG | GDB: 407638 | 7q35-36 | HERG, similar to ether-a-go go (eag), Ikr, long Q-T syndrome 2 | Brain, heart |
| KCNJ1 | GDB: 204206 U65406, U12541 | 11q24 | ROMK1, Kir1.1, Hs.463, Bartter/hyperprostaglandin E syndrome | Kidney, pancreatic islets |
| KCNJ2 | GDB: 278964 U12507 | 17pter-qter | IRK1, Kir2.1, Hs.1547 | Muscle, neural tissue, heart |
| KCNJ3 | GDB: 278325 U50964 | 2q24.1 | GIRK1, Kir3.1 | Heart, cerebellum |
| KCNJ4 | GDB: 374080 Z97056 | 22q13.1 | HIR, HIRK1, HIRK2, Kir2.3 | Heart, skeletal muscle, brain |
| KCNJ5 | GDB: 547948 | 11q24 | CIR. KATP1, GIRK4, Kir3.4 | Heart, pancreas |
| KCNJ6 | GDB: 547949 U24660 | 21q22.1 | KCNJ7, GIRK2, KATP2, BIR1, Kir3.2, ataxia, weaver mice | Cerebellum, pancreatic islet |
| KCNJ8 | GDB: 633096 | 12p11.23] | Kir6.1, uKATP, ubiquitous $K_{ATP}$ α-subunit | Brain, heart, skeletal, smooth muscle, others |
| KCNJ10 | GDB: 3750203 | 1q22-23] | Kir1.2, Kir4.1 | Glia |
| KCNJ11 | GDB: 7009893 | [11p15.1] | Kir6.2, BIR, K(ATP) α-subunit, hyperinsulinemic hypoglycemia | Pancreatic islets |
| KCNJ12 | GDB: 4583927 | [17p11.1] | Kir2.2 | |
| KCNJ15 | GDB: 6275865 | [21q22.2] | Kir4.2 | |
| KCNJN1 | GDB: 6108062 | [ ] | Kir2.2v, subfamily inhibitor 1 | |
| SUR1 | GDB: 591970 | [11p15.1] | SUR(1), sulfonylurea receptor, K(ATP) β-subunit, hyperinsulinemic hypoglycemia | Pancreatic islets |

-continued

| Gene | Accession ID | Gene Locus | | Tissue Expression |
|---|---|---|---|---|
| SUR2 | | 12p12.1] | SUR2, SUR2A, B, sulfonylurea receptor 2 (1545-aa), β-subunit of K(ATP) | 2A: heart, 2B: brain, liver, skeletal, smooth muscle, urinary bladder |
| KCNK1 | GDB: 6045446 | 1q42-43 | DPK, TWIK1 | Kidney |
| KCNK2 | | 1q41 | TREK1 | Brain |
| KCNK3 | GDB: 9773281 | 2p23 | TASK | Kidney |

| Therapeutic Target | Enzyme Family | Assay |
|---|---|---|
| Alzheimer's | CMGC | ERK2 (P42mapk) |
| Alzheimer's | Phospholipase | PLA2 |
| Alzheimer's | Cyclooxygenases | COX2 |
| Alzheimer's | CaMK | MARKI |
| Alzheimer's | CaMK | MARK2 |
| Alzheimer's | AGC | PKCalpha |
| Alzheimer's | AGC | PKCgamma |
| Alzheimer's | AGC | PKCgamma |
| Alzheimer's | Cysteine proteases | caspase-3 |
| Alzheimer's | Cysteine proteases | caspase-6 |
| Alzheimer's | Aspartic proteases | BACE-1 (beta-secretase) |
| Alzheimer's | Aspartic proteases | cathepsin D |
| Alzheimer's | Aspartic proteases | cathepsin E |
| Alzheimer's | Metalloproteases | ACE |
| Alzheimer's | Metalloproteases | ACE |
| Alzheimer's | Metalloproteases | TACE |
| Alzheimer's | NO synthases | constitutive NOS (cerebellar) |
| Alzheimer's | Monoamine &neurotransmitter synthesis & metabolism | acetylcholinesterase |
| Alzheimer's | Monoamine &neurotransmitter synthesis & metabolism | COMT (catechol-O-methyl transferase) |
| Alzheimer's | Monoamine &neurotransmitter synthesis & metabolism | MAO-A |
| Alzheimer's | Monoamine &neurotransmitter synthesis & metabolism | MAO-B |
| Alzheimer's | Monoamine &neurotransmitter synthesis & metabolism | tyrosine hydroxylase |
| Alzheimer's | Phospholipase C | PLC |
| Alzheimer's | Miscellaneous enzymes | xanthine oxidase/ superoxide 02-scavenging |
| Dependence/Addiction | AGC | PKA |
| Dependence/Addiction | AGC | PKCalpha |
| Dependence/Addiction | AGC | PKCbeta 1 |
| Dependence/Addiction | AGC | PKCbeta 2 |
| Dependence/Addiction | AGC | PKCdelta |
| Dependence/Addiction | Monoamine &neurotransmitter synthesis & metabolism | GABA transaminase |
| Dependence/Addiction | Cyclases | adenylyl cyclase (stimulated) |
| Dependence/Addiction | Phospholipase C | PLC |
| Dependence/Addiction | ATPase | ATPase (Na$^+$/K$^+$) |
| Inflammation/Arthritis/Allergy | RTK | EGFR kinase |
| Inflammation/Arthritis/Allergy | RTK | FLT-1 kinase (VEGFR1) |
| Inflammation/Arthritis/Allergy | RTK | KDR kinase (VEGFR2) |
| Inflammation/Arthritis/Allergy | CTK | Fyn kinase |
| Inflammation/Arthritis/Allergy | CTK | HCK |
| Inflammation/Arthritis/Allergy | CTK | Lek kinase |
| Inflammation/Arthritis/Allergy | CTK | Lyn kinase |
| Inflammation/Arthritis/Allergy | CTK | ZAP70 kinase |
| Inflammation/Arthritis/Allergy | CMGC | ERK2 (P42mapk) |
| Inflammation/Arthritis/Allergy | CMGC | JNK 1 |
| Inflammation/Arthritis/Allergy | CMGC | JNK 2 |
| Inflammation/Arthritis/Allergy | CMGC | P38alpha kinase |
| Inflammation/Arthritis/Allergy | Phospholipase | PLA2 |
| Inflammation/Arthritis/Allergy | Cyclooxygenases | COX1 |
| Inflammation/Arthritis/Allergy | Cyclooxygenases | COX2 |
| Inflammation/Arthritis/Allergy | TXA2 synthetase | TXA2 synthetase |

-continued

| Therapeutic Target | Enzyme Family | Assay |
|---|---|---|
| Inflammation/Arthritis/Allergy | CaMK | MAPKAPK2 |
| Inflammation/Arthritis/Allergy | AGC | PKA |
| Inflammation/Arthritis/Allergy | Lipoxygenases | 12-lipoxygenase |
| Inflammation/Arthritis/Allergy | Lipoxygenases | 15-lipoxygenase |
| Inflammation/Arthritis/Allergy | Serine proteases | elastase |
| Inflammation/Arthritis/Allergy | Serine proteases | cathepsin G |
| Inflammation/Arthritis/Allergy | Serine proteases | kallikrein |
| Inflammation/Arthritis/Allergy | Serine proteases | tryptase |
| Inflammation/Arthritis/Allergy | Cysteine proteases | caspase-1 |
| Inflammation/Arthritis/Allergy | Cysteine proteases | caspase-4 |
| Inflammation/Arthritis/Allergy | Cysteine proteases | caspase-5 |
| Inflammation/Arthritis/Allergy | Cysteine proteases | cathepsin B |
| Inflammation/Arthritis/Allergy | Cysteine proteases | cathepsin X |
| Inflammation/Arthritis/Allergy | Aspartic proteases | cathepsin E |
| Inflammation/Arthritis/Allergy | Metalloproteases | MMP-1 |
| Inflammation/Arthritis/Allergy | Metalloproteases | MMP-2 |
| Inflammation/Arthritis/Allergy | Metalloproteases | MMP-3 |
| Inflammation/Arthritis/Allergy | Metalloproteases | MMP-7 |
| Inflammation/Arthritis/Allergy | Metalloproteases | MMP-8 |
| Inflammation/Arthritis/Allergy | Metalloproteases | MMP-9 |
| Inflammation/Arthritis/Allergy | Metalloproteases | MMP-13 |
| Inflammation/Arthritis/Allergy | Metalloproteases | MT1-MMP (MMP-14) |
| Inflammation/Arthritis/Allergy | Metalloproteases | TACE |
| Inflammation/Arthritis/Allergy | Phosphatases | phosphatase CD45 |
| Inflammation/Arthritis/Allergy | Phosphodiesterases | PDE2 |
| Inflammation/Arthritis/Allergy | Phosphodiesterases | PDE4 |
| Inflammation/Arthritis/Allergy | Phosphodiesterases | acid sphingomyelinase |
| Inflammation/Arthritis/Allergy | Monoamine & neurotransmitter synthesis & metabolism | HNMT (histamine N-methyltransferase) |
| Inflammation/Arthritis/Allergy | Miscellaneous enzymes | myeloperoxidase |
| Inflammation/Arthritis/Allergy | Miscellaneous enzymes | xanthine oxidase/ superoxide 02-scavenging |
| Neuroprotection | RTK | TRKB |
| Neuroprotection | CMGC | CDK5 |
| Neuroprotection | CMGC | DYRKla |
| Neuroprotection | CMGC | ERK1 |
| Neuroprotection | CMGC | ERK2 (P42mapk) |
| Neuroprotection | MCGC | JCK 3 |
| Inflammation/Arthritis/Allergy | Metalloproteases | MMP-13 |
| Inflammation/Arthritis/Allergy | Metalloproteases | MT1-MMP (MMP-14) |
| Inflammation/Arthritis/Allergy | Metalloproteases | TACE |
| Inflammation/Arthritis/Allergy | Phosphatases | phosphatase CD45 |
| Inflammation/Arthritis/Allergy | Phosphodiesterases | PDE2 |
| Inflammation/Arthritis/Allergy | Phosphodiesterases | PDE4 |
| Inflammation/Arthritis/Allergy | Phosphodiesterases | acid sphingomyelinase |
| Inflammation/Arthritis/Allergy | Monoamine & neurotransmitter synthesis & metabolism | HNMT (histamine N-methyltransferase) |
| Inflammation/Arthritis/Allergy | Miscellaneous enzymes | myeloperoxidase |
| Inflammation/Arthritis/Allergy | Miscellaneous enzymes | xanthine oxidase/ superoxide 02-scavenging |
| Neuroprotection | RTK | TRKB |
| Neuroprotection | CMGC | CDK5 |
| Neuroprotection | CMGC | DYRKla |
| Neuroprotection | CMGC | ERK1 |
| Neuroprotection | CMGC | ERK2 (P42mapk) |
| Neuroprotection | MCGC | JCK 3 |
| Neuroprotection | Cyclooxygenases | COXI |
| Neuroprotection | Cyclooxygenases | COX2 |
| Neuroprotection | CaMK | CaMK2alpha |
| Neuroprotection | AGC | PKA |
| Neuroprotection | Cysteine proteases | caspase-3 |
| Neuroprotection | Phosphodiesterases | PDEI |
| Neuroprotection | Phosphodiesterases | PDE6 |
| Neuroprotection | NO synthases | constitutive NOS (endothelial) |
| Neuroprotection | NO synthases | constitutive NOS (cerebellar) |
| Neuroprotection | Monoamine & neurotransmitter syntheses & metabolism | acetylcholinesterase |
| Neuroprotection | Monoamine & neurotransmitter syntheses & metabolism | COMT (catechol-O-methyl transferase) |
| Neuroprotection | Monoamine & neurotransmitter syntheses & metabolism | GABA transaminase |
| Neuroprotection | Monoamine & neurotransmitter syntheses & metabolism | HNMT (histamine N-methyltransferase) |

-continued

| Therapeutic Target | Enzyme Family | Assay |
|---|---|---|
| Neuroprotection | Monoamine & neurotransmitter syntheses & metabolism | MAO-A |
| Neuroprotection | Monoamine & neurotransmitter syntheses & metabolism | MAO-A |
| Neuroprotection | Monoamine & neurotransmitter syntheses & metabolism | PNMT (phenylethanoiamine-N-methyl transferase) |
| Neuroprotection | Monoamine & neurotransmitter syntheses & metabolism | tyrosine hydroxylase |
| Neuroprotection | Cyclases | guanylyl cyclase (basal) |
| Neuroprotection | Cyclases | guanylyl cyclase (stimulated) |
| Neuroprotection | ATPase | ATPase (Na+/K+) |
| Neuroprotection | Miscellaneous enzymes | xanthine oxidase/superoxide 02-scavenging |
| Parkinson | CMGC | JNK 1 |
| Parkinson | Phospholipase | PLA2 |
| Parkinson | Cyclooxygenases | COX2 |
| Parkinson | Cysteine proteases | caspase-3 |
| Parkinson | NO synthases | constitutive NOS (cerebellar) |
| Parkinson | Monoamine & neurotransmitter syntheses & metabolism | acetylcholinesterase |
| Parkinson | Monoamine & neurotransmitter syntheses & metabolism | COMT (catechol-O-methyl transferase |
| Parkinson | Monoamine & neurotransmitter syntheses & metabolism | MAO-A |
| Parkinson | Monoamine & neurotransmitter syntheses & metabolism | MAO-B |
| Cancer | RTK | Axl kinase |
| Cancer | RTK | c-kit kinase |
| Cancer | RTK | c-kit kinase |
| Cancer | RTK | EGFR kinase |
| Cancer | RTK | EphA1 kinase |
| Cancer | RTK | EphA3 kinase |
| Cancer | RTK | EphA4 kinase |
| Cancer | RTK | EphB2 kinase |
| Cancer | RTK | FGFR1 kinase |
| Cancer | RTK | FGFR2 kinase |
| Cancer | RTK | FGFR3 kinase |
| Cancer | RTK | FGFR4 kinase |
| Cancer | RTK | FLT-1 kinase (VEGFR1) |
| Cancer | RTK | FLT-3 kinase |
| Cancer | RTK | FLT-4 kinase (VEGFR3) |
| Cancer | RTK | Fms/CSFR kinase |
| Cancer | RTK | HER2/ErbB2 kinase |
| Cancer | RTK | HER4/ErbB4 kinase |
| Cancer | RTK | KDR kinase (VEGFR2) |
| Cancer | RTK | PDGFRalpha kinase |
| Cancer | RTK | PDGFRbeta kinase |
| Cancer | RTK | Ret kinase |
| Cancer | RTK | TIE2 kinase |
| Cancer | RTK | TRKA |
| Cancer | CTK | Abl kinase |
| Cancer | CTK | BLK |
| Cancer | CTK | BMX (Bk) kinase |
| Cancer | CTK | BRK |
| Cancer | CTK | BTK |
| Cancer | CTK | CSK |
| Cancer | CTK | FAK |
| Cancer | CTK | Fes kinase |
| Cancer | CTK | Fyn kinase |
| Cancer | CTK | JAK2 |
| Cancer | CTK | JAK3 |
| Cancer | CTK | Lck kinase |
| Cancer | CTK | PYK2 |
| Cancer | CTK | Src kinase |
| Cancer | CTK | Syk |
| Cancer | CTK | Yes kinase |
| Cancer | CMGC | CDC2/CDK1 (cycB) |
| Cancer | CMGC | CDK2 (cycE) |

| Therapeutic Target | Enzyme Family | Assay |
|---|---|---|
| Cancer | CMGC | CDK4 (cycD1) |
| Cancer | CMGC | CDK5 |
| Cancer | CMGC | CK2 (casein kinase 2) |
| Cancer | CMGC | DYRK1a |
| Cancer | CMGC | ERK1 |
| Cancer | CMGC | ERK2 (P42mapk) |
| Cancer | CMGC | HIPK2 |
| Cancer | CMGC | IKKalpha |
| Cancer | CMGC | IKKbeta |
| Cancer | CMGC | JNK 1 |
| Cancer | CMGC | JNK 2 |
| Cancer | CMGC | NEK1 |
| Cancer | CMGC | NEK2 |
| Cancer | CMGC | NEK4 |
| Cancer | CMGC | p38alpha kinase |
| Cancer | CMGC | p38beta 2 kinase (SAPK2b2) |
| Cancer | CMGC | p38delta kinase |
| Cancer | CMGC | p38gamma kinase |
| Cancer | Cyclooxygenases | COX2 |
| Cancer | CaMK | CaMK1delta |
| Cancer | CaMK | CaMK |
| Cancer | CaMK | CHK1 |
| Cancer | CaMK | CHK2 |
| Cancer | CaMK | DAPK1 |
| Cancer | CaMK | DAPK2 |
| Cancer | CaMK | MAPKAPK2 |
| Cancer | CaMK | MAPKAPK3 |
| Cancer | CaMK | MAPKAPK5 (PRAKO |
| Cancer | CaMK | MAARK1 |
| Cancer | CaMK | MARK2 |
| Cancer | CaMK | MARK4 |
| Cancer | CaMK | Pim 1 kinase |
| Cancer | CaMK | Pim2 kinase |
| Cancer | AGC | Akt1/PKBalpha |
| Cancer | AGC | Akt2/PKBbeta |
| Cancer | AGC | Akt3/PKBgamma |
| Cancer | AGC | AurA/Aur2 kinase |
| Cancer | AGC | AurB/Aur1 kinase |
| Cancer | AGC | AurC/Aur3 kinase |
| Cancer | AGC | P70S6Ke |
| Cancer | AGC | PDK1 |
| Cancer | AGC | PKA |
| Cancer | AGC | PKCalpha |
| Cancer | AGC | PKCbeta 1 |
| Cancer | AGC | PKCbeta 2 |
| Cancer | AGC | PKCdelta |
| Cancer | AGC | PKCgamma |
| Cancer | AGC | PKG2 |
| Cancer | AGC | ROCK1 |
| Cancer | AGC | ROCK2 |
| Cancer | AGC | RSK2 |
| Cancer | AGC | SGKI |
| Cancer | Lipoxygenases | 12-lipoxygenase |
| Cancer | TKL | RAF-1 kinase |
| Cancer | STE | MEK1/MAP2KI |
| Cancer | STE | MKK4/JNK1 |
| Cancer | STE | MKK6 |
| Cancer | STE | PAK1 |
| Cancer | STE | PAK2 |
| Cancer | Serine proteases | elastase |
| Cancer | Serine proteases | cathepsin G |
| Cancer | Cysteine proteases | caspase-2 |
| Cancer | Cysteine proteases | caspase-3 |
| Cancer | Cysteine proteases | caspase-8 |
| Cancer | Cysteine proteases | caspase-9 |
| Cancer | Cysteine proteases | cathepin B |
| Cancer | Cysteine proteases | cathepsin H |
| Cancer | Cysteine proteases | cathepsin L |
| Cancer | Cysteine proteases | cathepsin X |
| Cancer | Aspartic proteases | cathepsin D |
| Cancer | Aspartic proteases | cathepsin E |
| Cancer | Metalloproteases | MMP-1 |
| Cancer | Metalloproteases | MMP-2 |
| Cancer | Metalloproteases | MMP-3 |
| Cancer | Metalloproteases | MMP-7 |
| Cancer | Metalloproteases | MMP-8 |

| Therapeutic Target | Enzyme Family | Assay |
| --- | --- | --- |
| Cancer | Metalloproteases | MMP-9 |
| Cancer | Metalloproteases | MMP-12 |
| Cancer | Metalloproteases | MMP-13 |
| Cancer | Metalloproteases | MT1-MMP (MMP-14) |
| Cancer | Metalloproteases | TACE |
| Cancer' | Metalloproteases | MMP-1 |
| Cancer | Phosphatases | phosphatase 1B |
| Cancer | Phosphatases | phosphatase 2B |
| Cancer | Phosphodiesterases | PDE2 |
| Cancer | Phosphodiesterases | PDE4 |
| Cancer | Phosphodiesterases | PDE5 |
| Cancer | Phosphodiesterases | acid spingomyelinase |
| Cancer | NO synthases | constitutive NOS (endothelial) |
| Cancer | NO synthases | constitutive NOS (cerebellar) |
| Cancer | Cyclases | adenylyl cyclase (basal) |
| Cancer | Cyclases | adenylyl cyclase (stimulated) |
| Cancer | Phospholipase C | PLC |
| Cancer | Miscellaneous enzymes | myeloperoxidase |
| Cancer | Miscellaneous enzymes | xanthine oxidase/superoxide 02-scavenging |
| Diabetes | RTK | Ax1 kinase |
| Diabetes | RTK | EGFR kinase |
| Diabetes | RTK | IGFIR kinase |
| Diabetes | CMGC | ERK2 (P42mapk) |
| Diabetes | CMGC | Jnk1 |
| Diabetes | Cyclooxygenases | COX2 |
| Diabetes | TXA2 synthetase | TXA2 synthetase |
| Diabetes | CaMK | AMPKalpha |
| Diabetes | AGC | Akt1/PKBalpha |
| Diabetes | AGC | Akt2/PKBbeta |
| Diabetes | AGC | Akt3/PKBgamma |
| Diabetes | AGC | PDK1 |
| Diabetes | AGC | PKA |
| Diabetes | AGC | PKCalpha |
| Diabetes | AGC | PKCbeta I |
| Diabetes | AGC | PKCbeta 2 |
| Diabetes | AGC | PKCgamma |
| Diabetes | AGC | SGK2 |
| Diabetes | Metalloproteases | ACE |
| Diabetes | Metalloproteases | MMP-1 |
| Diabetes | Metalloproteases | MMP-2 |
| Diabetes | Metalloproteases | MMP-3 |
| Diabetes | Metalloproteases | MMP-7 |
| Diabetes | Metalloproteases | MMP-8 |
| Diabetes | Metalloproteases | MMP-9 |
| Diabetes | Metalloproteases | MT1-MMP (MMP-14) |
| Diabetes | Metalloproteases | TACE |
| Diabetes | Phosphodiesterases | PDE3 |
| Diabetes | Phosphodiesterases | PDE4 |
| Diabetes | Phosphodiesterases | PDE5 |
| Diabetes | NO synthases | constitutive NOS (endothelial) |
| Diabetes | Monoamine & neurotransmitter synthesis & metabolism | acetylcholinesterase |
| Diabetes | Monoamine & neurotransmitter synthesis & metabolism | GABA transaminase |
| Diabetes | Monoamine & neurotransmitter synthesis & metabolism | MAO-B |
| Diabetes | Cyclases | adenylyl cyclase (basal) |
| Diabetes | Miscellaneous enzymes | acetylCoA synthetase |
| Diabetes | Miscellaneous enzymes | HMG-CoA reductase |
| Diabetes | Miscellaneous enzymes | xanthine oxidase/superoxide 02-scavenging |
| Metabolic Diseases | Cyclooxygenases | COX2 |
| Metabolic Diseases | AGC | PICA |
| Metabolic Diseases | Metalloproteases | ACE |
| Metabolic Diseases | Phosphodiesterases | PDE3 |
| Metabolic Diseases | Phosphodiesterases | PDE4 |
| Metabolic Diseases | NO synthases | constitutive NOS (endothelial) |

-continued

| Therapeutic Target | Enzyme Family | Assay |
|---|---|---|
| Metabolic Diseases | Miscellaneous enzymes | acetylCoA synthetase |
| Metabolic Diseases | Miscellaneous enzymes | HMG-CoA reductase |
| Metabolic Diseases | Miscellaneous enzymes | xanthine oxidase/superoxide 02-scavenging |
| Obesity | CTK | PYK2 |
| Obesity | CMGC | JNK1 |
| Obesity | CaMK | AMPJakoga |
| Obesity | AGC | PKA |
| Obesity | Metalloproteases | ACE |
| Obesity | Metalloproteases | ACE |
| Obesity | Phosphatases | phosphatase IB |
| Obesity | Phosphodiesterases | PDE2 |
| Obesity | Phosphodiesterases | PDE3 |
| Obesity | Monoamine & neurotransmitter synthesis & metabolism | acetylcholinesterase |
| Obesity | ATPase | ATPase (Na+/K+) |
| Obesity | Miscellaneous enzymes | HMG-CoA reductase |
| Reproduction | Phospholipase | PLA2 |
| Reproduction | Cyclooxygenases | COX1 |
| Reproduction | Cyclooxygenases | COX2 |
| Reproduction | Phosphodiesterases | PDE5 |
| Reproduction | NO synthases | constitutive NOS (endothelial) |
| Reproduction | Cyclases | guanylyl cyclase (stimulated) |
| Cystic Fibrosis | Phospholipase | PLA2 |
| Cystic Fibrosis | TXA2 synthetase | TXA2 synthetase |
| Cystic Fibrosis | AGC | PKA |
| Cystic Fibrosis | AGC | PKCbeta 1 |
| Cystic Fibrosis | AGC | PKCbeta 2 |
| Cystic Fibrosis | Serine proteases | elastase |
| Cystic Fibrosis | Serine proteases | cathepsin G |
| Cystic Fibrosis | Metalloproteases | MMP-2 |
| Cystic Fibrosis | Phosphodiesterases | PDE3 |
| Cystic Fibrosis | Phosphodiesterases | PDE5 |
| Cystic Fibrosis | Cyclases | adenylyl cyclase (stimulated) |
| Cystic Fibrosis | Phospholipase C | PLC |
| Cystic Fibrosis | Miscellaneous enzymes | myeloperoxidase |
| Immunosuppression Profile | RTK | EGFR kinase |
| Immunosuppression Profile | CTK | JAK3 |
| Immunosuppression Profile | CMGC | ERK2 (P42mapk) |
| Immunosuppression Profile | Cyclooxygenases | COX1 |
| Immunosuppression Profile | Cyclooxygenases | COX2 |
| Immunosuppression Profile | Serine proteases | elastase |
| Immunosuppression Profile | Serine proteases | cathepsin G |
| Immunosuppression Profile | Serine proteases | tryptase |
| Immunosuppression Profile | Cysteine proteases | cathepsin B |
| Immunosuppression Profile | Metalloproteases | ECE-1 |
| Immunosuppression Profile | Metalloproteases | ECE-1 |
| Immunosuppression Profile | Metalloproteases | MMP-1 |
| Immunosuppression Profile | Metalloproteases | MMP-2 |
| Immunosuppression Profile | Metalloproteases | MMP-9 |
| Immunosuppression Profile | Phosphatases | phosphatase CD45 |
| Immunosuppression Profile | Phosphodiesterases | PDE4 |
| Immunosuppression Profile | Phosphodiesterases | acid spingomyelinase |
| Immunosuppression Profile | Cyclases | adenylyl cyclase (basal) |
| Immunosuppression Profile | Cyclases | adenylyl cyclase (stimulated) |
| Migraine | Cyclooxygenases | COX2 |
| Migraine | NO synthases | constitutive NOS (cerebellar) |
| Migraine | Monoamine & neurotransmitter synthesis & metabolism | GABA transaminase |
| Migraine | Cyclases | guanylyl cyclase (stimulated) |
| Pain | CMGC | ERK2 (42mapk) |
| Pain | Phospholipase | PLA2 |
| Pain | Cyclooxygenases | COXI |
| Pain | Cyclooxygenases | COX2 |
| Pain | AGC | PICA |
| Pain | Serine proteases | elastase |
| Pain | Metalloproteases | MMP-1 |
| Pain | Metalloproteases | MMP-2 |
| Immunosuppression Profile | Serine proteases | elastase |

-continued

| Therapeutic Target | Enzyme Family | Assay |
| --- | --- | --- |
| Immunosuppression Profile | Serine proteases | cathepsin G |
| Immunosuppression Profile | Serine proteases | tryptase |
| Immunosuppression Profile | Cysteine proteases | cathepsin B |
| Immunosuppression Profile | Metalloproteases | ECE-1 |
| Immunosuppression Profile | Metalloproteases | ECE-1 |
| Immunosuppression Profile | Metalloproteases | MMP-1 |
| Immunosuppression Profile | Metalloproteases | MMP-2 |
| Immunosuppression Profile | Metalloproteases | MMP-9 |
| Immunosuppression Profile | Phosphatases | Phosphatase CD45 |
| Immunosuppression Profile | Phosphodiesterases | PDE4 |
| Immunosuppression Profile | Phosphodiesterases | acid spingomyelinase |
| Immunosuppression Profile | Cyclases | adenylyl cyclase (basal) |
| Immunosuppression Profile | Cyclases | adenylyl cyclase (stimulated) |
| Migraine | Cyclooxygenases | COX2 |
| Migraine | NO synthases | constitutive NOS (cerebellar) |
| Migraine | Monoamine & neurotransmitter synthesis & metabolism | GABA transaminase |
| Migraine | Cyclases | guanylyl cyclase (stimulated) |
| Pain | CMGC | ERK2 (42mapk) |
| Pain | Phospholipase | PLA2 |
| Pain | Cyclooxygenases | COXI |
| Pain | Cyclooxygenases | COX2 |
| Pain | AGC | PICA |
| Pain | Serine proteases | elastase |
| Pain | Metalloproteases | MMP-1 |
| Pain | Metalloproteases | MMP-2 |
| Pain | Metalloproteases | MMP-3 |
| Pain | Metalloproteases | MMP-7 |
| Pain | Phosphodiesterases | PDE4 |
| Pain | NO synthases | constitutive NOS (endothelial) |
| Pain | NO synthases | constitutive NOS (cerebellar) |
| Pain | Monoamine & neurotransmitter synthesis & metabolism | GABA transaminase |
| Pain | Monoamine & neurotransmitter synthesis & metabolism | MAO-A |
| Pain | Monoamine & neurotransmitter synthesis & metabolism | MAO-B |
| Pain | Monoamine & neurotransmitter synthesis & metabolism | tyrosine hydroxylase |
| Pain | Miscellaneous enzymes | xanthine oxidase/superoxide 02-scavenging |

Sensor materials (including ion-detecting sensors and glucose-detecting sensors) as discussed herein can be sized and shaped in any suitable configuration that can be achieved using the polymer. For example, in certain embodiments, the nanosensors are non-spherical, such as a disk or a cube, or even sculpted or molded into a utilitarian or aesthetic shape. A sensor emulsion can be spun, sprayed, or evaporated onto any surface to create a porous sensor membrane. In certain embodiments, the sensor film can be of a size suitable for the application, such as the coating of a glass slide, the bottoms of wells of a 96-well plate, or even a beverage dispenser, such as a pitcher, tank, or bottle. Films formed from microspheres tend to expose a greater surface area of sensor to a given sample, yielding improved performance characteristics.

The film of the sensor can be produced in various ways. In one implementation, as described above, a predetermined amount of the sensor mixture (e.g., the combined polymer phase, ionophore, quantum dots/dye, additive, and chromoionophore) is dissolved in a solvent, such as THF. The solution is then deposited, sprayed, or spun onto a surface. The solvent evaporates, leaving the sensor film on the surface.

In another implementation, the film is formed from a deposition of sensor microspheres. To produce the microspheres, a sensor emulsion is formed by injecting a sensor suspension dissolved in THF (e.g., 16 mL THF/100 mg PVC) into a pH buffered solution. The sensor suspension includes approximately 60 mg of DOS, 30 mg of PVC, and up to approximately 5 mg of chromoionophore, additive, and ionophore. The emulsion is then submerged in a sonicating water bath. Typically, 50 µL of the sensor suspension/THF solution is injected into 1,000-1,500 µL of buffered solution. The resulting emulsion contains a mixture of spherical sensor particles ranging in size from 200 nm to 20 pm in diameter. In certain embodiments, the nanosensors range in size from about 5 nm to about 300 nm in diameter, such as about 20 nm to about 200 nm in diameter, e.g., about 100 nm. In certain embodiments, the nanosensors that comprise only one quantum dot range in size from about 5 nm to about 50 nm in diameter, such as about 5 nm to about 25 nm in diameter, e.g., 20 nm. In certain embodiments wherein the particles are non-spherical, the diameter is measured at the widest dimension of the nanosensor. Particles of larger dimension are, of course, readily prepared.

In certain aspects, a film of the sensor material or particles is deposited on the surface of a support. In certain embodiments, the support is an instrument that can be placed in a solution such as a glass rod, a stirring bar, a straw, or glass beads. In certain embodiments, the support is a container in which the sample solution to be evaluated can be contained. In certain embodiments, the surface of the support is partially coated with the sensor particles while in other embodiments, the support surface is entirely coated with the sensor particles. In certain embodiments, the sensors are incorporated within the support and the support is sculpted into a desired shape such as a stir bar, a film, or a bead.

In certain embodiments, iCVD or piCVD may be used to coat sensors or sensor particles with a polymer or copolymer coating. In certain embodiments, the polymer or copolymer coatings may comprise biocompatible polymer.

In certain embodiments, the invention includes methods for detecting the presence of an analyte in a medium, comprising contacting a sensor particle of the invention with a medium, exposing the quantum dot to light energy that causes the quantum dot to emit photons and using a detector to detect the photons and determining the presence or absence of analyte based on the detected photons. In certain embodiments, the analyte is an ion, while in other embodiments, the analyte is a chelatable analyte, such as glucose. In certain embodiments, the light energy is selected from ultraviolet, infrared, near infrared or visible radiation. In certain embodiments, the light energy is ultraviolet. In certain embodiments, the medium comprises water, blood, plasma, urine, or cytoplasm. In certain embodiments, the method of detecting analyte, e.g. ions or glucose, with a sensor particle of the invention is performed in vitro.

In certain embodiments, the sensors are placed in contact with cells in biological samples such as tissues outside of the host specimen. In certain embodiments, the sensors are introduced to cells within a host specimen such as a plant or animal. The nanosensor particles may be introduced into the cells in any suitable manner. In one method, the particles are introduced into a buffer liquid deposited in the biological sample holder. A voltage source then generates a voltage sufficiently strong to electroporate the cells, thereby allowing the nanosensor particles to enter directly into the cells. In another approach, the surfaces of the nanosensor particles are first coated with a substance such as a surface modifier, a targeting moiety, an internalizing moiety or any combination thereof, which assist the particles in crossing through lipophilic membranes. The nanosensor particles contact the cells which bring the particles into their interior in vesicles via endocytosis, pinocytosis, phagocytosis, or similar biological processes. In certain embodiments, the internalizing moiety of the nanosensor particle breaks down the vesicle membrane, releasing the nanosensor particle into the cell cytoplasm. In still other approaches, the particles may be introduced into cells using a glass needle or through ballistic bombardment.

To determine compartmentalization of nanosensors within the cells TEM and fluorescence staining can be used. TEM can be used to determine location of the nanosensor in a cell, to provide a good understanding of nanosensor transport in the cell and serve as a validation of the co-localization staining. The second method, co-localization staining, can be used to determine endosomal release.

Dyes suitable for performing co-localization studies include: FM1-43, FM4-64, Fluorescein, Transferrin, and Lysotracker Red. FM1-43 is a lipophilic dye that readily stains cell membranes. Previous studies have shown the effectiveness of FM1-43 to stain endosomes. Its fluorescence emission is typically greatly increased upon incorporation into a hydrophobic environment. FM1-43 will typically stain the plasma membrane of a cell and remain associated with the lipid bilayer as it forms an endosome. Dye that is not taken into the cell and remains on the plasma membrane can be easily removed by gentle washing. FM4-64 is an analog of FM1-43 and behaves in a very similar fashion. It is more hydrophobic then FM1-43 and therefore may be more suitable for endocytosis studies. FM4-64 has been well characterized as an endosomal stain. The long wavelength emission of FM4-64 may be advantageous when using sensors of different spectral properties similar to the other fluorescent stains being utilized.

In some embodiments, the sensor is attached to the exterior of a cell rather than introduced into the interior. If, for example, the activity of an ion channel is to be studied, an ion-detecting sensor may be attached to the cell surface or placed in close proximity to the cell surface in a location where ion concentrations are in flux, such as adjacent to an ion channel. The sensor may be positioned adjacent to the ion channel of a cell, for example, by covalently linking one or more antibodies that selectively bind the ion channel of interest to a sensor particle as described above. The antibody-linked sensor particles may be added to a cell suspension to bind to the ion channel. This approach can be used to link sensors to any feature on the exterior of the cell membrane to which antibodies selectively bind. Alternatively, the sensors may be attached to the cell membrane by other suitable coupling chemistries, e.g., biotin-(strept)avidin complexing or polysaccharide binding. See the thesis "High Throughput Optical Sensor Arrays for Drug Screening" by Daniel I. Harjes (2006), available from the Massachusetts Institute of Technology and incorporated herein by reference.

In certain embodiments, cells or tissues are contacted with both nanosensor particles and a sensor film. In certain embodiments, the quantum dots used in the sensor film differ from the quantum dots used in the nanosensor particles. In particular, the different quantum dots desirably have distinguishable fluorescence characteristics such that an analysis module analyzing the output of a light sensor monitoring the sensor arrangement can differentiate between the output of the sensor film and the nanosensor particles. As a result, the analysis module can differentiate between intracellular analyte concentration and extracellular analyte concentration. In an exemplary embodiment, the sensor film comprises quantum dots of a selected fluorescence wavelength, e.g., 560 nm, and the nanosensor particles comprise quantum dots of a selected fluorescence wavelength, e.g., 655 nm. In addition, an ion-detecting sensor film may include ionophores different from those included in ion-detecting sensor particles, e.g., nanosensor particles comprising sodium ionophores and sensor films comprising potassium ionophores. Thus, the sensor arrangement can monitor the concentrations of two different target ions.

In still another embodiment, the sensor film is coated onto the inner surface of a biological sample holder. And in another approach, to accommodate multiwell plates, such as the 96-well plate format often used in assays, one embodiment of the present invention utilizes round glass coverslips coated with the sensor film along with the cells to be monitored. In certain embodiments, larger multiwell plates such as 384- and 1536-well plates are applied with a layer of sensor film disposed on a surface of some or all of the wells. In these embodiments, each well contains a single sensor type to track a specific species of interest; the various sensor types may differ in the ionophore employed and utilize quantum dots with fluorescence wavelengths that are the same or similar. The compound of interest is then added directly to the well.

The multiwell plate is then placed in a fluorometer and the fluorescence intensity is monitored with time.

In a typical implementation, a plurality of biological sample holders holding biological samples is provided. Biological samples introduced into the holders may include cells suspended in a buffer solution, but alternatively cells may be adhered to the walls of the biological sample holders. Next, sensors are introduced into biological sample holders and/or are introduced into the cells themselves. Alternatively, the sensors can coat the walls of the biological sample holders. As described above, nanosensor particles can be introduced either by electroporating the cells via electrodes positioned in the biological sample holders or by the chemistry applied to the nanosensor particles breaching vesicle membranes within the cells. Similarly, the sensors can be introduced into the cells using pico-injection, bead loading, a gene gun, or through liposomal delivery techniques known in the art.

An agent, such as a therapeutic, toxin, biological macromolecule (such as a nucleic acid, an antibody, a protein or portion thereof, e.g., a peptide), small molecule (of 2000 amu or less, 1000 amu or less or 500 amu or less), protein, virus, bacteria, chemical compound, mixture of chemical compounds, or an extract made from biological materials such as bacteria, plants, fungi, or animal (particularly mammalian) cells or tissues, or other biologically active agent may be introduced into one or more of the biological sample holders. In one particular implementation using an array of biological sample holders, no agent is introduced into a first row of biological sample holders to preserve a control. A first agent is introduced into a second row of biological sample holders. Additional agents are added to additional rows of the array of biological sample holders. The fluorescence of the sensors introduced into the biological sample holders may be monitored. The monitoring preferably begins prior to introduction of the agents and continues thereafter. Changes in analyte concentration resulting from the introduced agents are then determined. By comparing the changes in analyte concentration after adding an agent, one can determine the effect of the agent on the cells being tested.

In certain embodiments, ion-detecting sensors are used to detect ions in water or other aqueous solutions. In certain embodiments, the support deposited with the sensor particles is used to detect the presence of ions in an aqueous solution. In certain exemplary embodiments, the sensors are used to detect ions in water, e.g., tap water or ground water, to determine the levels of toxic ions in solution or to determine the hardness of the aqueous solution. In certain exemplary embodiments, the sensors are added to manufacturing solutions to measure ions during production of, e.g., the mass production of soda, ion-restoring beverages or other ionic drinks. In certain embodiments, the sensors are used in the laboratory to monitor the ion content of a reaction mixture or stock solution.

Other exemplary embodiments and implementations are disclosed in PCT Publication No. WO2008/063151A2 and U.S. patent application Ser. No. 11/888,663, hereby incorporated by reference in their entirety.

The sensors of the invention can be used to monitor the effects of pharmaceutical agents on biological systems such as the cardiovascular system or the circulatory system. Action potentials generated by cardiac or neural cells in culture are defined by a flux of sodium and potassium into and out of the cell. In certain embodiments, ion-detecting sensors of the invention measure this ion flux in cardiac cells accurately and spatially in a high throughput manner.

In certain aspects, the sensors are used in the drug discovery process. In certain such embodiments, the sensors are used to measure the efficacy of a therapy. For example, ion-selective sensors may be employed to monitor the effect of ion channel-modulating drugs. In alternative embodiments, sensors are used to screen for cytotoxic substances by, for example, determining ionic flux in cardiac cells in response to a cytotoxic agent and using these values as a comparison for testing novel therapeutic agents.

In certain aspects, the invention provides a method for detecting an analyte in an animal using any of the sensors or sensor particles of the invention. In certain embodiments, the invention provides a method for detecting the presence of an analyte in an animal, comprising the steps of: contacting a sensor particle of the invention with an animal cell or tissue, wherein the sensor particle comprises at least one quantum dot and/or fluorescent dye; a polymer matrix comprising a polymer matrix including moieties that couple to an analyte and a chromophore associated with the polymer matrix that binds to the moieties in the absence of the analyte; exposing the particles to light energy that causes the quantum dot and/or fluorescent dye to emit photons; using a detector to detect the photons; and determining the presence or absence of coupled analyte based on the detected photons. In certain embodiments, the particle is implanted within the dermis or epidermis of an animal. In certain embodiments, the analyte is an ion. In certain embodiments, the analyte is a chelatable analyte. In certain embodiments, the chelatable analyte is glucose.

In certain aspects, the sensors of the invention are implanted into small animals to monitor biological responses to new therapeutic agents. In certain embodiments, the implantable sensors are used to study the mechanism of disease in small animals. In certain such embodiments, the animals, such as rats or mice, are, for example, infected with a disease and the biological functions are monitored by detecting the signal of the implanted optical sensors. In such embodiments, the animal is placed within a monitoring element, e.g., a fluorescent monitoring cell similar to a monitoring element used to take X-rays of small animals, wherein the quantum dots of the sensors are excited, e.g., with UV light, and fluorescence emitted from the sensors within the animal may be detected.

In certain embodiment, the method for detecting an analyte in an animal comprises implanting the particle below the surface of the epidermis or dermis of the animal. The particle may be implanted intracellularly, while in other embodiments, the sensors are implanted extracellularly. When implanted in tissues, the composition may be taken into a cell or remain external to a cell. The particle may be implanted between about 0.05 mm and about 4 mm below the surface of the epidermis or dermis of the animal. In certain embodiments, the particle is injected or surgically inserted within the dermis or epidermis of an animal. In certain embodiments, the particle is injected within the dermis or epidermis of the animal. In certain embodiments, the particle is injected in a solution. In certain embodiments, a particle solution comprises multiple particles. The particle solution may comprise particles with an average particle size between 10 nm and 10 microns. In certain embodiments, the particle solution comprises particles with an average particle size between 10 microns and 500 microns such as between 50 microns and 200 microns. In certain embodiments, the amount of signal decrease over time due to fouling and leaching for the implanted particle sensor is minimal.

In certain embodiments, the implanted particle produces an optical change upon contact with a chelatable analyte. In certain embodiments, the optical change is the appearance of a color upon chelation of the moieties of the particle with the chelatable analyte, For example, in certain embodiments, when a colorless particle comes into contact with the chelatable analyte glucose, the chelatable particle turns red. In certain embodiments, wherein the particle is implanted in the dermis or epidermis, the color change can be seen from the surface of the skin. In certain other embodiments, the sensor turns yellow, green, blue, purple or orange.

In certain embodiments, the particle emits photons when contacted by a chelatable analyte which can be detected spectrophotometrically. The particle may emit photons immediately upon making contact with the analyte. In certain embodiments, the particle may emit photons after a brief time such as 1-5 seconds upon making contact with the analyte. In an exemplary embodiment, when a particle comprising a quantum dot contacts glucose, the particle emits photons which can be detected with a spectrophotometer. In certain embodiments, the number of photons detected can be correlated with the amount of analyte present in a medium, e.g., blood. In certain embodiments, where the particle is implanted in the dermis or epidermis, the photons can be detected through the skin. In certain embodiments, the detector is a hand held unit that can be held near the skin to detect photons emitted from the sensor.

The epidermis may vary in thickness depending upon its location and the animal, but is generally up to about 1 mm thick in a human. When implanted in the epidermis, it is preferred that the particle is placed or implanted of from about 0.05 mm, about 0.06 mm, about 0.07 mm, about 0.08 mm, about 0.09 mm, about 0.10 mm, about 0.12 mm, about 0.14 mm, about 0.16 mm, about 0.18 mm, about 0.2 mm, about 0.22 mm, about 0.24 mm, about 0.26 mm, about 0.28 mm, about 0.30 mm, about 0.32 mm, about 0.34 mm, about 0.36 mm, about 0.38 mm, about 0.40 mm, about 0.42 mm, about 0.44 mm, about 0.46 mm, about 0.48 mm, about 0.50 mm, about 0.52 mm, about 0.54 mm, about 0.56 mm, about 0.58 mm, about 0.60 mm, about 0.62 mm, about 0.64 mm, about 0.66 mm, about 0.68 mm, about 0.70 mm, about 0.72 mm, about 0.74 mm, about 0.76 mm, about 0.78 mm, about 0.80 mm, about 0.82 mm, about 0.84 mm, about 0.86 mm, about 0.88 mm, about 0.90 mm, about 0.92 mm, about 0.94 mm, about 0.96 mm, or about 0.98 mm to about 1 mm below the outer surface of the epidermis of an animal. In another preferred aspect, the particle is implanted between about 0.1 mm and about 0.15 mm below the surface of the epidermis of the animal. Preferred animals include sheep, goats, cats, dogs, birds, cows, horses or pigs. A particularly preferred animal is a human.

When implanted in the epidermis of an animal, the particle may exist only days or weeks before the cells containing or surrounding the particle are shed from the animal. In certain embodiments, the particle would remain in the position in which it was implanted for 1-4 weeks. In certain embodiments, the particle will exist up to about 2 weeks before removal through natural replacement of epidermal layers.

In another embodiment, the particle is implanted in the dermis or dermal layers of an animal. The dermis may very in thickness depending upon its location and the animal, but is generally from about 1 mm to about 4 mm thick in a human. The dermis is located beneath the epidermis, often generally beginning about 1 mm beneath the epidermis, often generally beginning about 1 mm beneath the outer surface of the epidermis. The dermis does not actively shed, so that a particle may exist semi-permanently or permanently in an animal, i.e., remain in the dermis for months or years. Depending on the thickness of the epidermis and dermis, in certain embodiments, the particle may be implanted or placed in the dermis of from about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6 mm, about 4.7 mm, about 4.8 mm, or about 4.9 mm to about 5.0 mm beneath the outer surface of the epidermis. In certain preferred embodiments, the particle would be implanted of from about 1 mm to about 5 mm beneath the surface of the epidermis, with about 2 mm to about 3 mm being particularly preferred.

In certain embodiments, the particle sensor is coupled with an optical readout (e.g., placed over the implantation site). In certain embodiments utilizing a glucose-sensitive sensor, a small insulin pump may be coupled to the optical readout device. The insulin pump may be configured such that the insulin pump is activated to deliver insulin if the optical readout detects a level of glucose above a predetermined value.

The invention now being generally described, it will be more readily understood by reference to the following examples which are included merely for purposes of illustration of certain aspects and embodiments of the present invention, and are not intended to limit the invention in any way.

EXAMPLES

Figure 18:
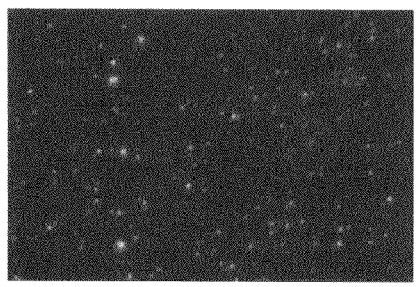
FIG. 18. Wide field fluorescence microscopic image of a suspension of sensor particles.

Nano-Scale Polymer-Coated Quantum Dots: Commercially available quantum dots (Evident Technologies, Troy, N.Y.) were dispersed in a polymeric matrix. In order to make the dispersion homogeneous, a ligand exchange was performed to add a decane-thiol to the surface of the quantum dot. The alkylated surface proved more miscible with the lipophilic polymer matrix. After a homogeneous distribution was obtained, nanoscale sensors were produced by sonicating the polymeric matrix dissolved in THF, containing all of the sensing elements including quantum dots, in an aqueous solution of PEG-lipid surface modifier. The resulting nanosensor solution was filtered to remove larger pieces of polymer. The resulting sensor suspension fluoresced brightly when viewed in a wide-field fluorescence microscope (FIG. 18).

Figure 19:
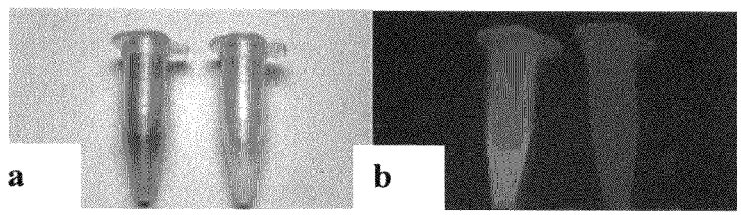
FIG. 19. Nanometer-sized sensor particles demonstrating the inner filter effect wherein: (a) the absorbance changes from purple to yellow depending on the binding state of the chromophore; (b) the same samples under UV excitation wherein the sample that was visually purple does not absorb the 525 nm emission of the quantum dots and fluoresces brightly, while the yellow sample absorbs the fluorescence emission of the quantum dot and has minimal emission.

Inner-Filter Effect: Nanometer-sized glucose-sensitive quantum dots (GSQDs) in solution are shown in FIG. 19. The absorbance changes from purple to yellow are easily seen by eye in FIG. 19 (left). The same samples of nanosensors under UV excitation are shown in FIG. 19 (right). The sample that was visually purple does not absorb the 525 nm emission of the quantum dots and fluoresces brightly. The yellow GSQD absorbs the fluorescence emission of the quantum dot and has minimal emission.

Figure 20:
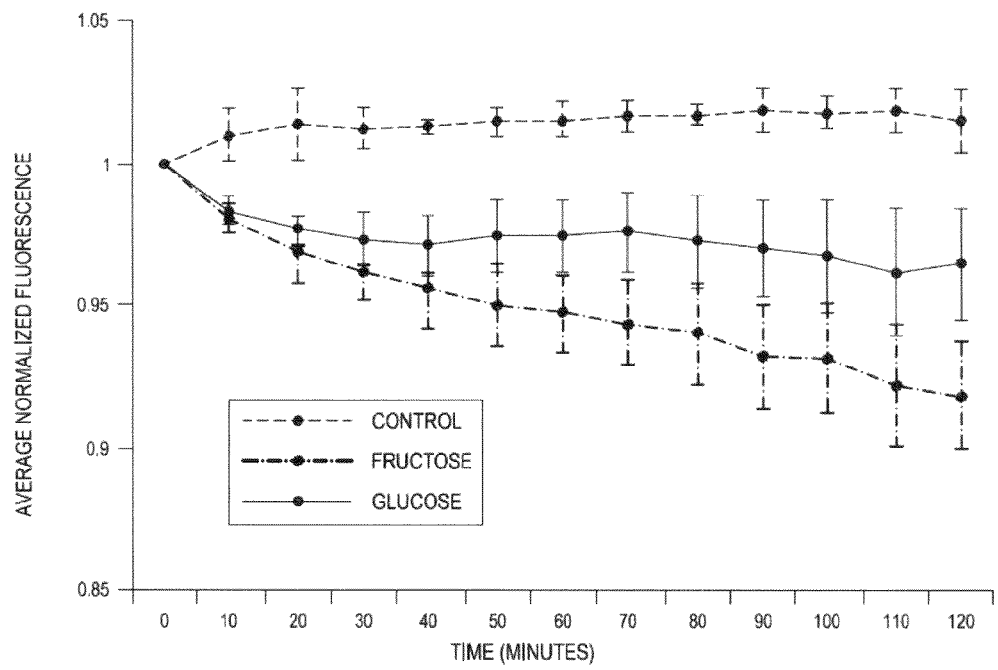
FIG. 20. Evaluating response to glucose, the sensor particles containing the essential sensing components, alizarin, pyrene boronic acid and additive, was immobilized to the bottom of a micro-well for calibration. Response to glucose and fructose was measured, the average±SEM is shown, where n=6 and n=8 for control and monosaccharides, respectively.

Response to Glucose: A polymer matrix containing the sensing components alizarin, pyrene boronic acid and additive, was immobilized to the bottom of a micro-well for calibration. Response to glucose and fructose was measured, the average±SEM is shown in FIG. 20, n=6 and 8 for control and monosaccharides, respectively.

Figure 10:
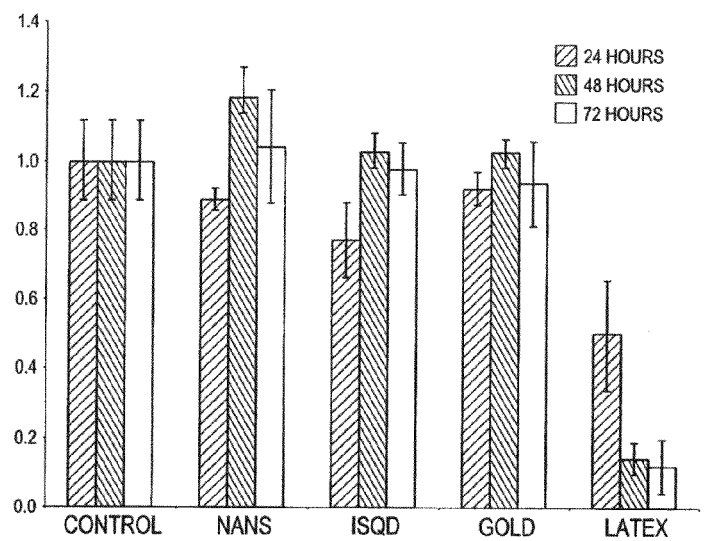
FIG. 10. Biocompatibility of nanosensors in HEK cells. HEK cells were incubated with either control (water), nanosensors without quantum dots (nans), quantum dot nanosensors (ISQD), 100 nm gold nanoparticles, or 20 nm latex beads (a negative control) and viability (y-axis) was evaluated.
Figure 11:
FIG. 11. Confocal image of nanosensors without quantum dots loaded into an HEK 293 cell.
Figure 12:
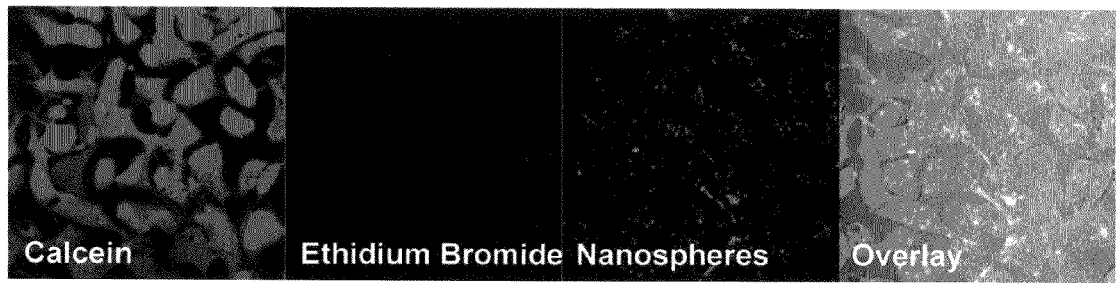
FIG. 12. A LIVE/DEAD assay wherein nanosensors with quantum dots were loaded into HEK 293 cells overnight and then stained. The green indicates healthy cells, while the red stains the nuclei of dead cells. No difference in the ratio of live to dead cells was noted between nanosensor loaded cells and control (no nanosensors).
Figure 13:
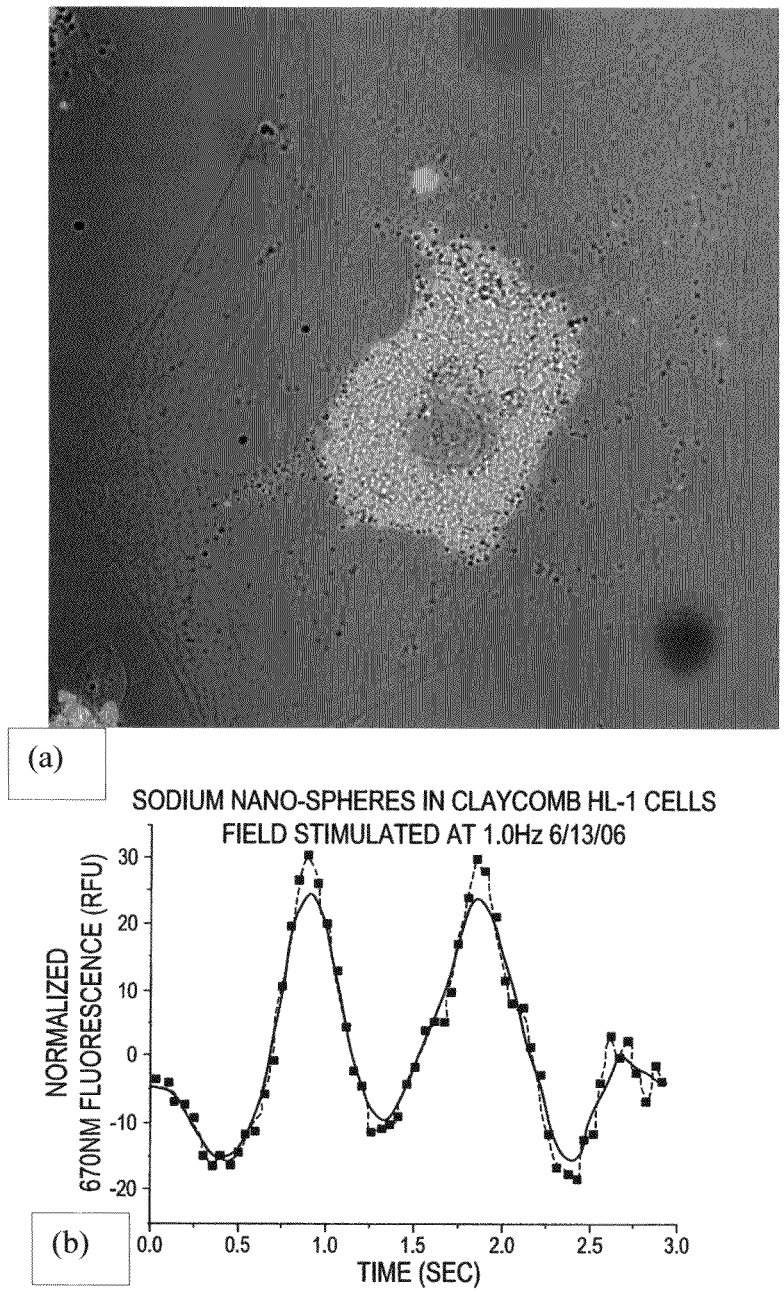
FIG. 13. (a) fluorescence image of an isolated neonatal rat ventricular myocyte loaded with sodium-selective nanosensors. (b) the fluorescence collected from a nanosensor in a cardiac cell during stimulation.

Biocompatibility: In vitro biocompatibility studies produced no indications of cellular injury thus far. For instance, LIVE-DEAD assays showed no differences from controls in the amount of cell death. In addition, the degree of cytotoxicity was determined by incubating the nanosensors overnight with HEK 293 cells and measuring the degree of cellular injury with an MTT assay. These results were compared to other nanoparticles and are shown in FIG. 10. The ion-sensitive quantum dot (ISQD) nanosensors show no cellular toxicity compared to controls over the course of 72 hours after incubation. This result is also seen for 100 nm diameter gold nanoparticles.

Initiated Chemical Vapor Deposition (iCVD): iCVD films of pHEMA may be deposited in a process disclosed in Gleason et al., PCT WO 2007/145657 A2, hereby incorporated by reference in its entirety.

Figure 21:
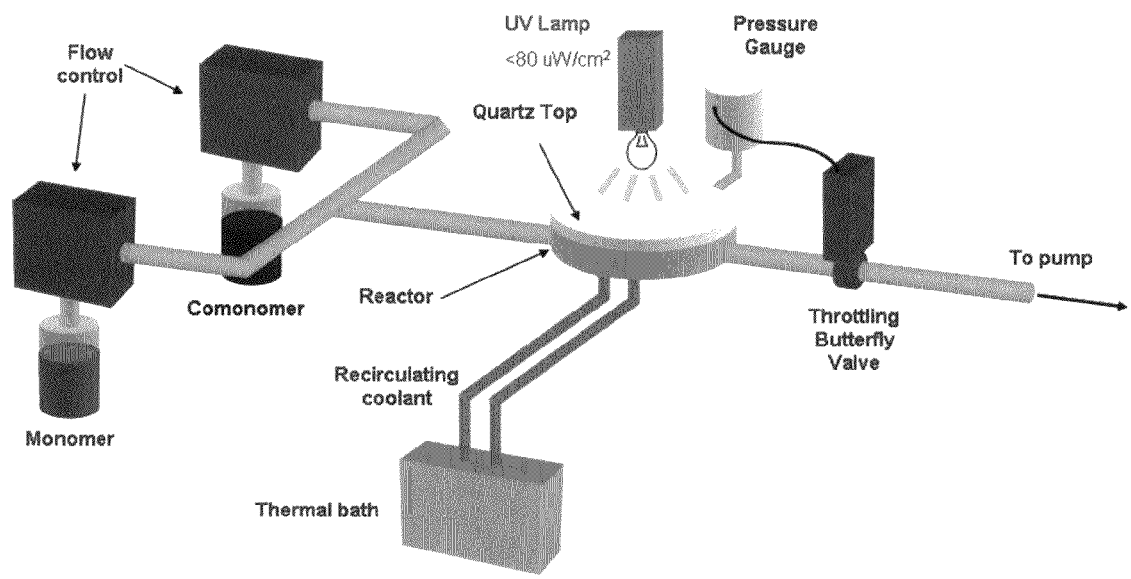
FIG. 21. An exemplary embodiment of a piCVD reactor used for coating samples.

Photoinitiated Chemical Vapor Deposition (piCVD): piCVD films of pHEMA were deposited on surfaces in a reactor similar to the reactor disclosed in Gleason et al, PCT WO 2007/145657 A2 for iCVD deposition. A low-power ultraviolet lamp (Model UVG-54, UVP) emitting ultraviolet light at 254 nm wavelength was mounted 9.0 cm above the reactor, with a 2.5 cm thick quartz viewport allowing the light to enter the reactor. The substrate stage was located 3.3 cm into the reactor. Thus, the total distance from the substrate to light source was 14.8 cm. The light intensity at this distance was 50 μW/cm$^2$. A laser interferometer allowed for real time tracking of the deposited film thickness and termination of growth at the desired film thickness. FIG. 21 depicts an exemplary piCVD reactor system.

HEMA monomer (99+%, Aldrich) was used as-received without any additional purification. The liquid monomer was vaporized in a stainless-steel jar and its vapor was metered into the reactor at 2 sccm, i.e., 2 standard cubic centimeters per minute, through a mass-flow controller (Model 1152, MKS). No separate photoinitiator was used. The chamber pressure was maintained by a throttling butterfly valve (Model 653V, MKS) and the substrate temperature ($T_S$) was controlled via backside contact of the deposition stage with temperature-controlled water lines. Two experimental series were conducted for this study: one investigating the effect of mean free path of the vapor (experimental series A) and the other investigating the effect of substrate temperature (experimental series B). The experimental conditions are summarized in the table below. All films were deposited on flat silicon wafers.

| Experimental Condition | $T_s$ (° C.) | Pressure (mtorr) | HEMA (sccm) | Flowrate $P_M/P_M^{sat}$ |
|---|---|---|---|---|
| A1 | 30 | 100 | 2.5 | 0.42 |
| A2 | 30 | 100 | 2.0 | 0.42 |
| A3 | 30 | 100 | 1.5 | 0.42 |
| A4 | 30 | 100 | 1.0 | 0.42 |
| B1 | 20 | 100 | 2.0 | 0.94 |
| B2 | 25 | 100 | 2.0 | 0.63 |
| B3 | 30 | 100 | 2.0 | 0.42 |
| B4 | 40 | 100 | 2.0 | 0.20 |

Note:
$P_M/P_M^{sat}$ is the partial pressure of the monomer divided by its saturation pressure evaluated at the stage temperature.

Additionally, experimental condition B2 was also used to deposit films on large silica microspheres of diameter 50-100 μm (Polysciences) and small, monodisperse spheres of nominal diameter 5.0 μm (Bangslab). The large microspheres were placed in a petri dish in the vacuum chamber, manually agitated after every 100 nm of deposition to prevent particle agglomeration. The small particles were diluted in tetrahydrofuran, dispersed onto a silicon wafer, dried overnight, and then placed in the reactor for deposition. This experimental condition was also used to deposit 100 nm of film onto a flat optode sensor, whose preparation has been described elsewhere. The as prepared optode was coated without further modification. The responses of the coated and uncoated optodes were characterized via fluorometry.

Swelling Characterization. The film swelling capacity was determined via spectroscopic ellipsometeric (M-2000, J. A. Woollam) measurements of thickness. The wafer was cut into 2.5 cm×8 cm strips prior to measuring thickness. Dry film thicknesses were determined by spectroscopic ellipsometry at an incident angle of 75°. The data were fit to a Cauchy-Urbach isotropic model (WVASE 32, J. A. Woollam). The films were then mounted in a liquid cell (J. A. Woollam) and the cell was injected with pH 7.4 phosphate buffer solution (cellgro, Mediatech). Ellipsometric data were then collected 1, 3, 5, 10, and 30 minutes following injection of the buffer solution. In all cases, the film reached its equilibrium film thickness (within 1 nm) after 5 minutes. The water content of the swollen film was determined by dividing the increase in film thickness by the total thickness of the swollen film. This method of determining equilibrium swollen water content has been previously shown to closely match the more complex effective medium approximation. To test the stability of the polymer films and reversibility of the swelling response, the films were rinsed in deionized water, dried in a vacuum oven for 30 minutes, and the dry and swollen thicknesses were obtained again.

Interaction with Proteins. X-ray photoelectron spectroscopy (XPS) was used to quantify the degree of non-specific protein adhesion on the p(HEMA) films. A 1 wt % protein solution was prepared by dissolving 200 mg of bovine serum albumin (Fraction V, Sigma Aldrich) in 19.8 mL phosphate buffer solution. Three pieces of sample B2 and three pieces of a bare silicon wafer were incubated in the protein solution for three hours at 37° C. Samples were then rinsed with approximately 5 mL buffer solution to remove any non-bound protein and dried gently under nitrogen. The surface nitrogen content of each sample was then quantified by XPS (Kratos AXIS Ultra) survey scans.

Particle Characterization. After coating with pHEMA, the large microspheres were freeze-fractured and the particle cross-section was imaged via scanning electron microscopy (SEM, JEOL-5910). For the small microspheres, both uncoated and coated particles were imaged (JEOL-6320FV) and their diameters measured via built-in image processing in the SEM software (JEOL Orion).

Figure 22:
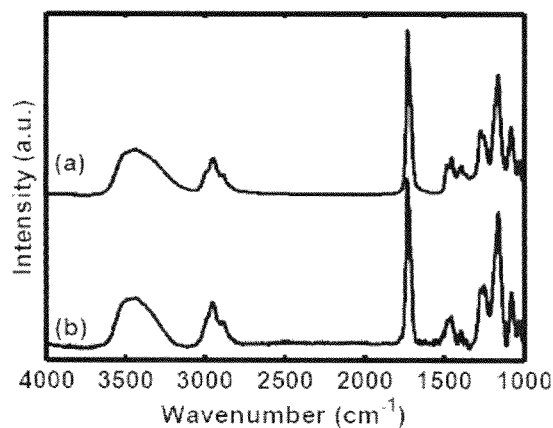
FIG. 22. FTIR spectra of (a) standard pHEMA and (b) piCVD pHEMA.

Chemical Structure. FIG. 22 compares a typical FTIR spectrum of piCVD pHEMA to a polymer standard. The absence of peaks in due to unsaturated carbon at 1640-1660 cm$^{-1}$ or 3000-3100 cm$^{-1}$ indicates that monomer polymerized through its vinyl moiety to form polymer. Both the piCVD and standard polymer exhibit a broad peak at 3200-3600 cm$^{-1}$, corresponding to the hydroxyl group, and a sharp peak at 1725-1730 cm$^{-1}$, corresponding to carbonyl stretching. The spectra therefore demonstrate that the piCVD of HEMA monomer proceeds through a free-radical mechanism while retaining the side-group functionality. Because HEMA is the only species introduced into the reactor during synthesis, the polymerization is likely initiated by the excitation of HEMA monomer. Indeed, at UV wavelengths below 267 nm, carbonyl species are known to decompose into radical species, which in turn can initiate a free-radical polymerization. Despite this, the similarity between the piCVD film and the polymer standard indicates that the vast majority of the pendant hydroxyl and carbonyl groups are retained.

Figure 23:
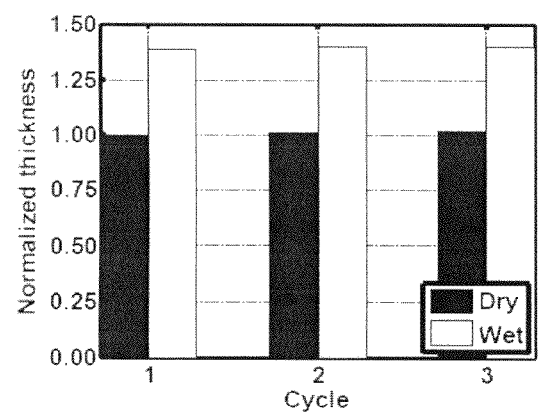
FIG. 23. Typical reversible swelling response of piCVD pHEMA in buffer solution for multiple swell/dry cycles.

Film Structure and Swelling Properties. To function as a protective overlayer for biosensor, a thin film preferably allows for the passage of small analytes from the medium to the sensor. It is therefore preferable that the film swell when in contact with a biological medium while remaining adhered to the sensor substrate. All the films synthesized in this study exhibited a rapid, reversible swelling response while maintaining adhesion to the substrate. As characterized by in situ spectroscopic ellipsometry, the films reached their equilibrium swollen water content within 5 min of submersion in pH 7.4 buffer solution. Upon rinsing in deionized water and drying under vacuum, the films returned to their original thickness. When submerged again, the films rapidly returned to their swollen state. FIG. 23 shows a typical response to several of these swell/dry cycles. The recovery of the original thickness after each swell/dry cycle indicates that polymer does not leach out of the film when submerged in buffer solution, an important property for any material with potential for biological or physiological use. It also indicates that the crosslinking within the film is not due exclusively to physical entanglements; purely physical crosslinking would result in the loss of film in the swelling and washing steps.

Figure 24:
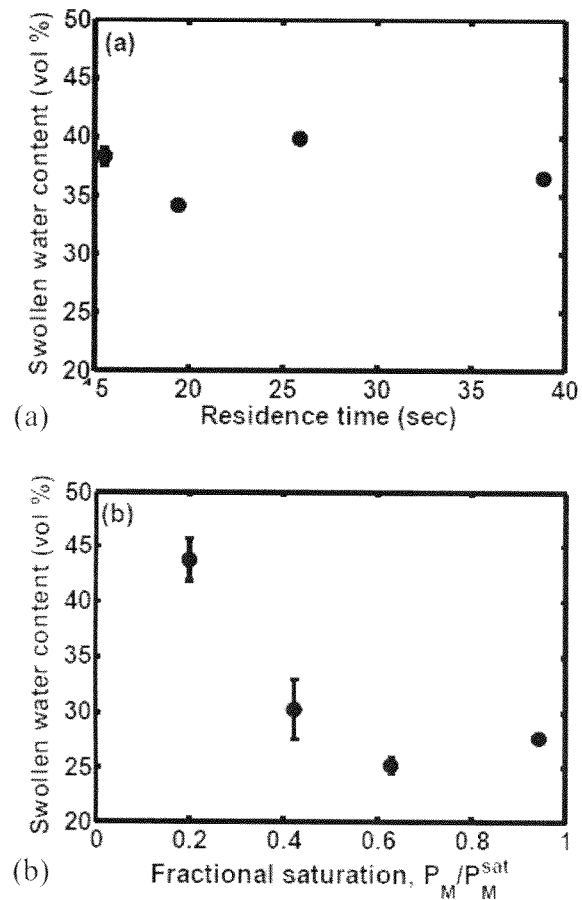
FIG. 24. Equilibrium swollen water content as a function of (a) vapor residence time and (b) fractional saturation of monomer during deposition.

In order to control the swellability of these films, it is preferable to understand whether the polymerization is initiated in the vapor phase or on the substrate surface. FIG. 24a (top) shows the swellability as a function of vapor residence time in the reactor (experimental series A). The residence time was determined by dividing the chamber volume (5467 mL) by the vapor flowrate. Changing the residence time alters UV exposure time for gaseous monomer molecules as they pass through the reactor. The relative independence of film swellability on irradiation time suggests that the polymerization is not a vapor phase process (FIG. 24a). These results suggest that irradiation chemistry at the surface is the dominant initiation mechanism for film deposition. To test this hypothesis, the surface concentration of monomer was systematically varied while holding residence time fixed (experimental series B). This was accomplished by varying the ratio of the partial pressure of the monomer to its saturation pressure at the stage temperature, $P_M/P_M^{sat}$. This ratio will be referred to as the fractional saturation of the monomer and has previously been shown to control the concentration of monomer at the substrate. The saturation pressure is evaluated using the Clapeyron equation. FIG. 24b displays a strong dependence of swellability on $P_M/P_M^{sat}$, consistent with a polymerization mechanism which is primarily a surface process. Changing $P_M/P_M^{sat}$, and therefore the surface concentration of monomer during synthesis, allows for the control of the swelling properties.

The moderate degree of swelling and the reversibility of the swelling response suggest that the films are highly crosslinked. The origin of the crosslinking is unclear since no separate crosslinker was introduced into the reactor. However, if the pendant carbonyl group can be decomposed into radicals under UV irradiation as suggested earlier, then each pendant group on the polymer chain can potentially act as a crosslinker. Furthermore, HEMA monomer may undergo transesterification or etherification to produce dimethacrylates, which are commonly used as crosslinking agents. Finally, physical crosslinking via chain entanglement is also a possibility, although purely physical crosslinking is unlikely given the stability of the film over several swell/dry cycles. Understanding the degree of crosslinking, regardless of the nature of the crosslinks themselves, is preferable for understanding how these films can potentially be used as a protective overlayer for sensors in a biological environment. Non-specific protein adhesion can potentially damage the device, so the film preferably may be crosslinked enough prevent transport of proteins from the medium to the device surface. At the same time, the analyte preferably may be able to permeate the film.

Figure 25:
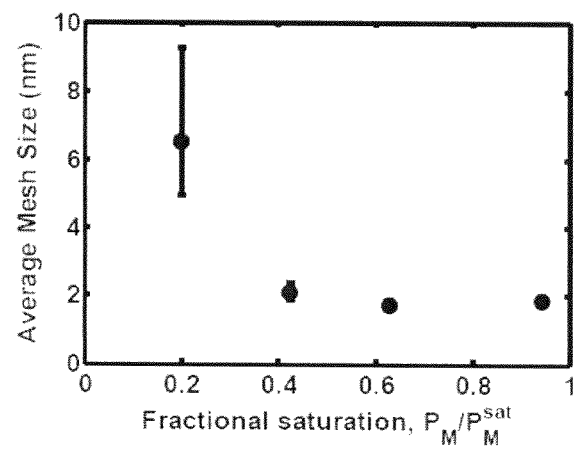
FIG. 25. Average mesh size of swollen films.

The crosslinking is intimately related to the swollen water content of the film; for highly crosslinked networks, the swollen water content and the average molecular weight between crosslinks satisfy the following equation:

$$\frac{1}{\overline{M}_C} = \frac{2}{\overline{M}_n} - \frac{\frac{\overline{v}}{V_1}[\ln(1-v_{2,s}) + v_{2,s} + \chi(v_{2,s})^2]\left[1 - \frac{M_r}{2\overline{M}_C}(v_{2,s})^{2/3}\right]^3}{\left((v_{2,s})^{1/3} - \frac{1}{2}v_{2,s}\right)\left(1 + \frac{M_r}{2\overline{M}_C}(v_{2,s})^{1/3}\right)^2} \quad (1)$$

where $\overline{M}_C$ is the average molecular weight between crosslinks, $v$ is the specific volume of pHEMA, $\chi$ is the Flory-Huggins interaction parameter, $V_1$ is the molar volume of water, $M_r$ is the molecular weight of the HEMA repeat unit, and $v_{2,s}$ is the ratio of the thickness of the dry polymer to the thickness of the swollen polymer. This theory is developed for linear polymer chains of number-average molecular weight $\overline{M}_n$ that undergo crosslinking by the introduction of a crosslinking agent. Measuring $\overline{M}_n$ for the piCVD films is difficult because the crosslinking occurs in situ and without a separate chemical species. Commonly, $\overline{M}_n$ is assumed to be large enough that the term in which it appears can be neglected. This assumption provides an upper bound on $\overline{M}_C$. The molecular weight between crosslinks can in turn be used to compute the average mesh size in the swollen film. It should be noted that the crosslink density as calculated by (1) is an effective value that does not distinguish between physical entanglements and chemical crosslinking. FIG. 25 shows the average mesh size for films B1-B4 as computed by (1). Each of these mesh sizes is large enough to allow for the passage of small molecule analytes such as metal cations (e.g., sodium or potassium) or sugars (e.g., glucose). However, these mesh sizes are too small to allow for the permeation of large biomolecules such as proteins. For example, albumin is a 3.8 nm×15.0 nm ellipsoid molecule and fibrinogen is a 9 nm×45 nm ellipsoid.

Figure 26:
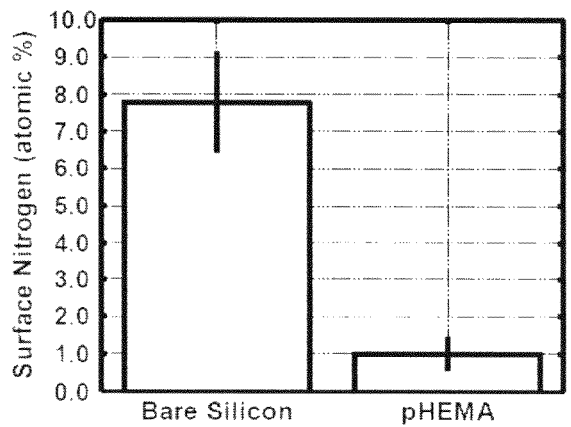
FIG. 26. Surface nitrogen content of bare silicon and pHEMA after incubation in a 1 wt % protein solution for three hours at 37° C.

Protein Adhesion. While the films are capable of protecting device surfaces from contact with proteins, the films themselves should also resist protein adhesion. XPS characterization of the piCVD films following incubation in a protein solution (BSA) provided a convenient proxy for measuring the degree of protein adhesion. As the p(HEMA) film does not contain any nitrogen, any nitrogen detected by the highly surface-sensitive XPS must be due to surface-bound proteins. FIG. 26 compares the nitrogen content of a p(HEMA) surface incubated in a solution of bovine serum albumin (BSA) with a control silicon surface. The p(HEMA) film exhibits an eight-fold decrease in surface nitrogen signal over bare silicon, corresponding to a reduction of surface bound proteins.

Figure 27:
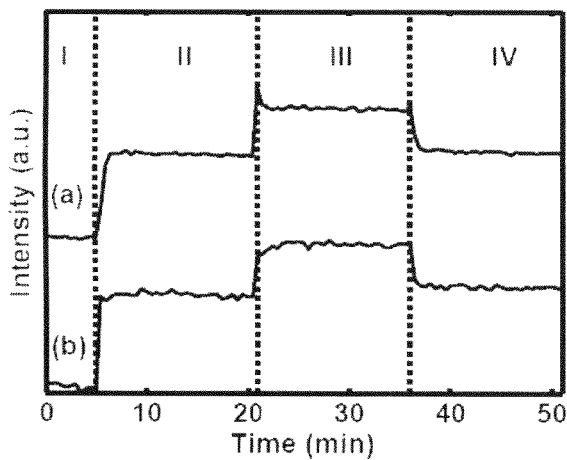
FIG. 27. Response curves of (a) uncoated optode and (b) optode coated with 100 nm piCVD pHEMA when submerged in pH 7.4 buffer containing I—0 Na+ ions, II—140 mM Na+ ions, III—340 mM Na+ ions, and IV—140 mM Na+ ions.

Sensor and Particle Coating. To demonstrate the gentle nature of the piCVD process, a sodium-sensing optode was coated with 100 nm of pHEMA. The optode is a chromoionophore and ionophore in a polymer matrix cast as a film (<10 µm thickness) on a 1 cm diameter glass coverslip. The responses of both an uncoated optode and a coated optode to varying levels of sodium ion concentration are shown in FIGS. 27a and 27b, respectively. It is evident that the piCVD process does not damage the optode functionality.

The coated optode also shows little or no degradation in response time when compared to the uncoated optode. The response of the device is governed by the diffusion of sodium ion through optode matrix, which is several microns thick. The nanoscale thickness of the overlaying pHEMA film does not add significantly to the distance that the ion must diffuse. Additionally, the fact that the sodium ion diffuses through the film is consistent with the calculated mesh size. Small molecule analytes, such as ions, have no difficulty diffusing through a film with a mesh size on the order of several nanometers.

Figure 28:
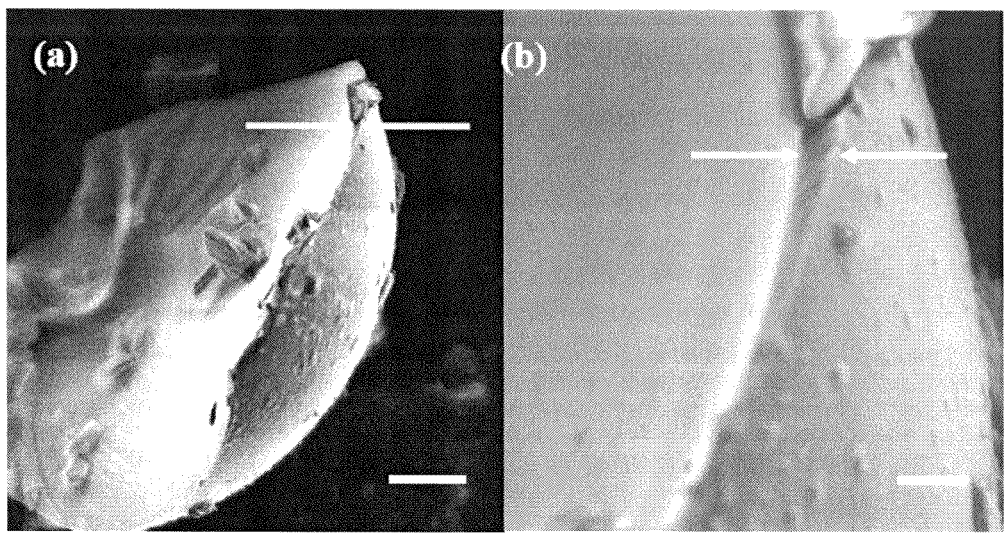
FIG. 28. SEM cross-section of a silica microsphere coated with piCVD pHEMA at (a) 1600× magnification (scale bar=10 μm) and (b) 5500× magnification (scale bar=2 μm). The arrows indicate the polymer layer.
Figure 29:
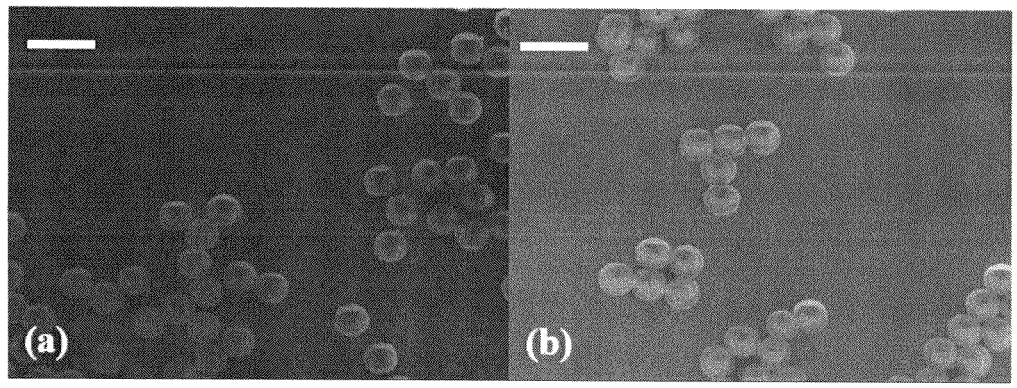
FIG. 29. SEM images of (a) uncoated silica microspheres and (b) silica microspheres coated with piCVD pHEMA. Both images were obtained at 1600× magnification and the scale bars represent 10 p.m.

Because piCVD is a dry process, the geometries that can be coated with pHEMA are not limited to planar surfaces. Indeed, many sensors of physiologically relevant analytes are being miniaturized as microparticles to take advantage of high surface areas and reductions in response time. As a dry process, piCVD can conformally coat microgeometries while avoiding the effects of solvent tension, which tends to result in particle agglomeration. FIG. 28 shows a cross section of a ~50 µm microsphere coated with approximately 1 µm of pHEMA. The coating is continuous and conformal around the outside of the particle. FIG. 29 compares SEM images of uncoated and coated monodisperse microparticles. The uncoated microspheres have an average diameter of 5.06±0.04 µm and the coated microspheres have an average diameter of 5.39±0.04 µm, indicating that the particles were coated with approximately 165 nm of hydrogel.

Those skilled in the art will recognize, or be able to ascertain using no more than routine experimentation, many equivalents to the specific embodiments of the invention described herein. Such equivalents are intended to be encompassed by the following claims.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

The invention claimed is:

1. A method for manufacturing a sensor for detecting an analyte, the method comprising:
   forming a polymer matrix;
   adding a fluorescence source and a chromophore into the polymer matrix, wherein the chromophore binds to the moieties in the absence of the analyte;
   forming a sensor particle from the polymer matrix; and
   applying a surface coating to the sensor particle, wherein the surface coating creates a continuous coating of the sensor particle and the surface coating is penetrable by the analyte and at least partially covalently bound to the surface of the sensor particle.

2. The method of claim 1, wherein applying the surface coating further comprises applying the surface coating using a solventless surface polymerization process.

3. The method of claim 2, wherein the solventless surface polymerization process is one of chemical vapor deposition and photoinitiated chemical vapor deposition.

4. The method of claim 3, wherein the chemical vapor deposition occurs in a vacuum with a pressure between about 100 mtorr and about 500 mtorr.

5. The method of claim 3, wherein the chemical vapor deposition occurs at a temperature between about 20° C. and about 100° C.

6. The method of claim 3, further comprising applying the surface coating during the chemical vapor deposition process at a rate between about 0.1 standard cubic centimeters per minute and about 3.0 standard cubic centimeters per minute.

7. The method of claim 1, wherein applying the surface coating to the sensor particle further comprises applying the surface coating to a thickness of between about 1 nm to about 100 µm.

8. The method of claim 1, further comprising selecting the surface coating such that the surface coating is substantially impermeable to the fluorescence source.

9. The method of claim 1, wherein the surface coating comprises one or more hydroxyethylmethacrylate monomers.

10. The method of claim 1, wherein the surface coating comprises a biocompatible polymer.

11. The method of claims 10, wherein the biocompatible polymer comprises Poly(2-hydroxyethyl methacrylate) (pHEMA).

12. The method of claim 1, wherein the polymer matrix comprises polyvinyl chloride (PVC).

13. The method of claim 1, wherein forming the polymer matrix comprises combining moieties with a polymer by mixing the moieties and the polymer into a tetrahydrofuran solution, and sonicating the solution.

14. The method of claim 1, wherein the sensor particle has a diameter between about 5 nm and about 300 nm.

15. The method of claim 1, wherein the analyte is glucose or fructose.

16. The method of claim 1, wherein the polymer matrix comprises one of boronic acid and boronic esters mixed with a polymer.

17. The method of claim 1, wherein the fluorescence source is one or more fluorescent dyes.

18. The method of claim 1, wherein the fluorescence source is quantum dots.

19. The method of claim 1, further comprising depositing a surface modifier on the surface coating, wherein the surface modifier is selected to promote delivery of the sensor into a cell.

20. The method of claim 19, wherein the surface modifier comprises an amine group.

* * * * *